United States Patent
Prétôt et al.

(10) Patent No.: US 7,928,242 B2
(45) Date of Patent: Apr. 19, 2011

(54) ELECTROLUMINESCENT METAL COMPLEXES WITH TRIAZOLES

(75) Inventors: Roger Prétôt, Basel (CH); Roman Kolly, Allschwil (CH); Thomas Schäfer, Liestal (CH); Paul Adriaan Van Der Schaaf, Hagenthal-le-Haut (FR)

(73) Assignee: BASF SE, Ludwigshafen (DE)

( * ) Notice: Subject to any disclaimer, the term of this patent is extended or adjusted under 35 U.S.C. 154(b) by 367 days.

(21) Appl. No.: 12/086,646

(22) PCT Filed: Dec. 18, 2006

(86) PCT No.: PCT/EP2006/069803
§ 371 (c)(1),
(2), (4) Date: Jun. 17, 2008

(87) PCT Pub. No.: WO2007/074093
PCT Pub. Date: Jul. 5, 2007

(65) Prior Publication Data
US 2009/0062560 A1    Mar. 5, 2009

(30) Foreign Application Priority Data
Dec. 28, 2005    (EP) ..................... 05113030

(51) Int. Cl.
C07F 15/00 (2006.01)
C07F 3/00 (2006.01)
B32B 9/00 (2006.01)
H01J 1/62 (2006.01)

(52) U.S. Cl. .................. 548/108; 428/690; 313/504

(58) Field of Classification Search .................. 548/108; 428/690; 313/504
See application file for complete search history.

(56) References Cited

U.S. PATENT DOCUMENTS

| | | | | |
|---|---|---|---|---|
| 3,197,475 A | * | 7/1965 | Carboni | 548/257 |
| 3,262,942 A | * | 7/1966 | Carboni | 548/258 |
| 3,281,414 A | * | 10/1966 | Mrozik et al. | 540/51 |
| 3,646,054 A | * | 2/1972 | Kirckmayr et al. | 548/256 |
| 3,757,011 A | * | 9/1973 | Fleck et al. | 548/257 |
| 3,839,352 A | * | 10/1974 | Kirchmayr et al. | 548/256 |
| 3,852,297 A | * | 12/1974 | Moser et al. | 548/109 |
| 3,954,532 A | * | 5/1976 | Kompolthy et al. | 149/45 |
| 4,001,253 A | * | 1/1977 | Harnisch et al. | 546/71 |
| 4,022,799 A | * | 5/1977 | Harnisch et al. | 548/261 |
| 5,247,190 A | | 9/1993 | Friend et al. | 257/40 |
| 5,408,109 A | | 4/1995 | Heeger et al. | 257/40 |
| 5,552,678 A | | 9/1996 | Tang et al. | 315/169.3 |

| | | | |
|---|---|---|---|
| 2001/0019782 A1 | 9/2001 | Igarashi et al. | 428/690 |
| 2002/0055014 A1 | 5/2002 | Okada et al. | 428/690 |
| 2008/0015355 A1 | 1/2008 | Schafer et al. | 546/4 |

FOREIGN PATENT DOCUMENTS
EP   0 443 861   8/1991
WO   2006/000544   1/2006

OTHER PUBLICATIONS

Appl. Phys. Lett. 1999, 75, 4.
J. A. C. Allison et al., J. Heterocyclic Chem. 12 (1975) 1275-1277.
M. Nonoyama and C. Hayata, Transition Met. Chem. 3 (1978) 366-369.
W.-S. Huang et al. In Chem. Mater. 16 (2004) 2480-2488.
P. J. Steel, G. B. Caygill, Journal of Organometallic Chemistry 327 (1987) 101-114.
P. Djurovich et al.; Polymer Preprints vol. 41 No. 1, (2000) pp. 770-771.
S. Lefkopoulou et al. J. Heterocyclic Chem. vol. 23, pp. 443-445 (1986).
P. Catsoulacos, J. Heterocyclic Chem. vol. 22, pp. 1671-1673(1985).
K.B. Sukumaran et al., Tetrahedron, vol. 30, pp. 445-450 (1974).

* cited by examiner

*Primary Examiner* — Porfirio Nazario Gonzalez
(74) *Attorney, Agent, or Firm* — Shiela A. Loggins; Qi Zhuo

(57) ABSTRACT

Disclosed are electroluminescent metal complexes with triazoles of the formula (I), where n1 is an integer of 1 to 3, m1 and m2 each are an integer 0, 1 or 2, $M^1$ is a metal with an atomic weight of greater than 40, $L^1$ is a monodentate ligand or a bidentate ligand, $L^2$ is a monodentate ligand, $Q^2$ stands for an organic bridging group completing, together with the bonding carbon atoms of the triazole ring, an annellated, carbocyclic or heterocyclic, non-aromatic ring, which optionally may be substituted, $Q^3$ represents a group of forming a condensed aromatic, or heteroaromatic ring, which can optionally be substituted, as well as new intermediates for the preparation of these complexes, electronic devices comprising the metal complexes and their use in electronic devices, especially organic light emitting diodes (OLEDs), as oxygen sensitive indicators, as phosphorescent indicators in bioassays, and as catalysts.

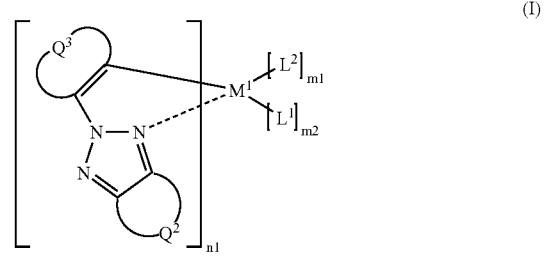

(I)

17 Claims, No Drawings

ELECTROLUMINESCENT METAL COMPLEXES WITH TRIAZOLES

This invention relates to electroluminescent metal complexes with triazoles, new intermediates for their preparation, electronic devices comprising the metal complexes and their use in electronic devices, especially organic light emitting diodes (OLEDs), as oxygen sensitive indicators, as phosphorescent indicators in bioassays, and as catalysts.

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, in U.S. Pat. No. 5,247,190, U.S. Pat. No. 5,408,109 and EP-A-443 861. Complexes of 8-hydroxyquinolate with trivalent metal ions, particularly aluminum, have been extensively used as electroluminescent components, as has been disclosed in, for example, U.S. Pat. No. 5,552,678.

Burrows and Thompson have reported that fac-tris(2-phenylpyridine) iridium can be used as the active component in organic light-emitting devices. (Appl. Phys. Lett. 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-C'.sup.2,N]iridium(III). (Polymer Preprints 2000, 41(1), 770.)

J. A. C. Allison et al., J. Heterocyclic Chem. 12 (1975) 1275-1277 discloses 2-phenyl-1,2,3-triazole chloro complexes of palladium and their use as catalysts in the synthesis of chlorinated phenyl triazines.

M. Nonoyama and C. Hayata, Transition Met. Chem. 3 (1978) 366-369 describe cyclometallations of 2-aryl-4,5-dimethyl-1,2,3-triazoles [H(C—N)] with palladium(II), platinum(II), rhodium(III) and iridium(II) chloride which results in [MCI(C—N)]$_2$ for M=Pd, or Pt and [MCI(C—N)$_2$]$_2$ species for M=Rh, or Ir. These complexes react with monodentate ligands, L, such as pyridine and tri-n-butylphosphine to give MCI(C—N)L and MCI(C—N)$_2$L complexes.

US20020055014 relates to a light-emitting device comprising a phosphorescent compound. Preferred phosphorescent compounds include compounds having a partial structure represented by the formula shown below

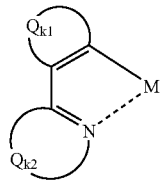

wherein M represents a transition metal; $Q_{k1}$ represents an atomic group necessary for forming a 5- or 6-membered aromatic ring; and $Q_{k2}$ represents an atomic group necessary for forming a 5- or 6-membered aromatic azole ring. The 5- or 6-membered aromatic azole ring completed by $Q_{k2}$ may include triazole, but does not include 1,2,3-triazole.

US20010019782 discloses a light-emitting material comprising a compound having a partial structure represented by the following formula

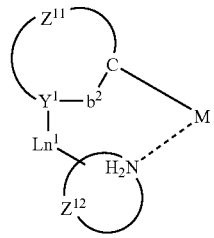

wherein $Z^{11}$ and $Z^{12}$ each represent a nonmetallic atom group required to form a 5- or 6-membered ring with at least one of carbon atom and nitrogen atom, said ring optionally having a substituent or forming a condensed ring with the other ring; $Ln^1$ represents a divalent group; $Y^1$ represents a nitrogen atom or carbon atom; and $b^2$ represents a single bond or double bond. Among the preferred examples of the 5- or 6-membered ring formed by $Z^{11}$ and $Z^{12}$ are 1,2,3-triazole rings, and 1,2,4-triazole rings. The divalent group $Ln^1$ does not comprise a single bond.

Phosphorescent bis-cyclometalated iridium complexes containing benzoimidazole-based ligands are described by W.-S. Huang et al. in Chem. Mater. 16 (2004) 2480-2488.

The $^1$H and $^{13}$C NMR of the following cyclopalladated metal complex are described in P. J. Steel, G. B. Caygill, Journal of Organometallic Chemistry 327 (1987) 101-114:

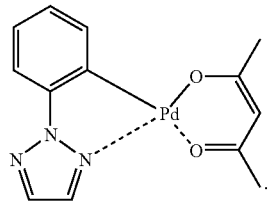

However, there is a continuing need for electroluminescent compounds having improved efficiency.

Accordingly, the present invention is directed to compounds (i.e. metal complexes) of the formula

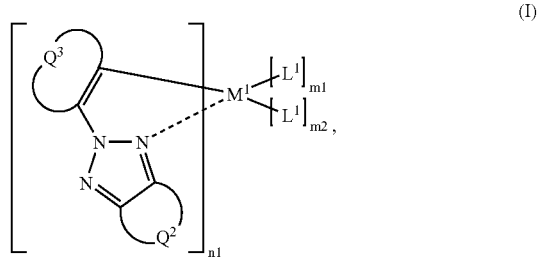

(I)

wherein
n1 is an integer of 1 to 3,
m1 and m2 are an integer 0, 1 or 2,
$M^1$ is a metal with an atomic weight of greater than 40,
$L^1$ is a monodentate ligand or a bidentate ligand,
$L^2$ is a monodentate ligand,
$Q^2$ stands for an organic bridging group completing, together with the bonding carbon atoms of the triazole ring, an annellated, carbocyclic or heterocyclic, non-aromatic ring, which optionally may be substituted,
$Q^3$ represents a group of forming a condensed aromatic, or heteroaromatic ring, which can optionally be substituted,
and further to a process for their preparation, electronic devices comprising the metal complexes and their use in electronic devices, especially organic light emitting diodes (OLEDs), as oxygen sensitive indicators, as phosphorescent indicators in bioassays, and as catalysts.

The present invention is directed to metal complexes comprising at least one ligand derived from a triazole annellated via its carbon atoms to a non-aromatic carbocyclic or heterocyclic ring, especially a 2,4,5,6,7-pentahydro-benzotriazole. The pentahydro-benzotriazole compound in the context of the present invention means a (carbocyclic) benzotriazole or a hetero-benzotriazole.

Examples for the moiety of the formula

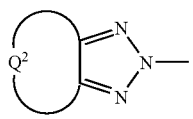

of the triazole ligand, as contained in the above formula I, include the following ones:

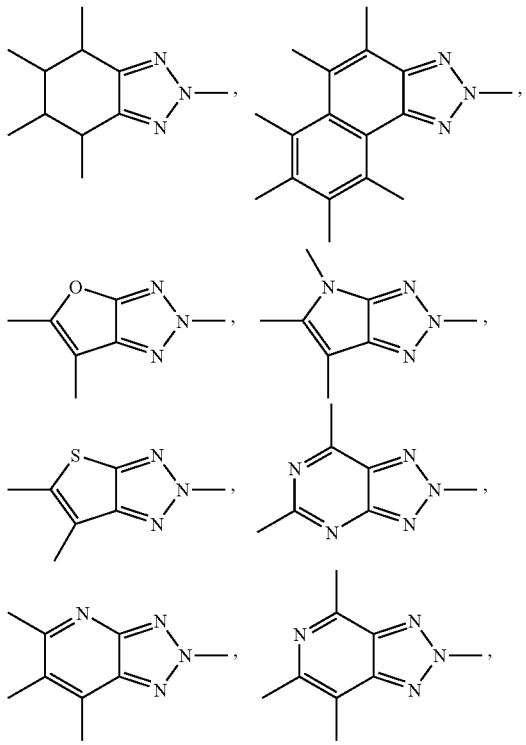

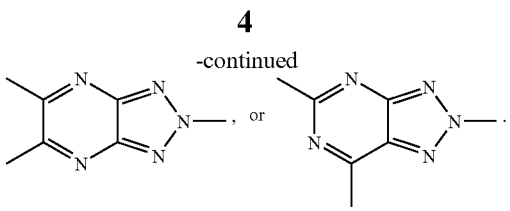

It is understood that the open valences in the moiety represent a covalent bond that is not limited in its substitution. According to the present invention the metal complex comprise at least one of the above triazole ligands, i.e. it may comprise two or three or more thereof. Thus, each open line in the above formulae indicates the position of a bond to another part of the same ligand (including substituents), or further hydrogen atoms.

For example,

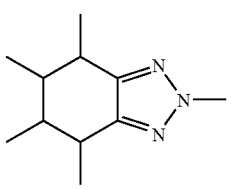

inter alia includes
4-phenylamino-6,6-dimethyl-4,5,6,7-tetrahydro-benzotriazol-2-yl,
4-oxo-6,6-dimethyl-4,5,6,7-tetrahydro-benzotriazol-2-yl,
4-hydroxyimino-4,5,6,7-tetrahydro-benzotriazol-2-yl,
5-fluoro-4,5,6,7-tetrahydro-benzotriazol-2-yl,
5-trifluoromethyl-4,5,6,7-tetrahydro-benzotriazol-2-yl.

Some examples for suitable triazole ligands include those of the formulae:

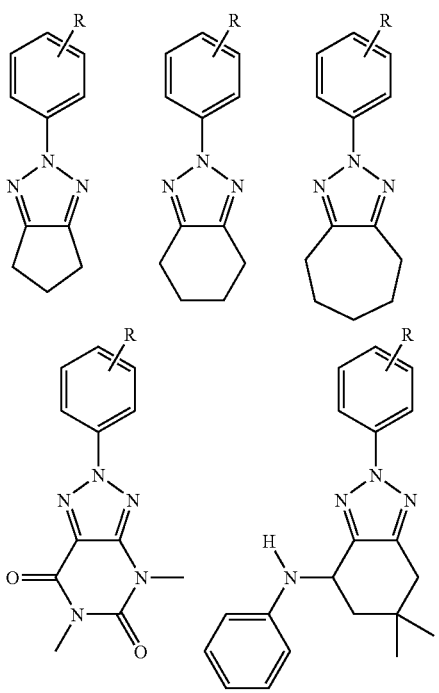

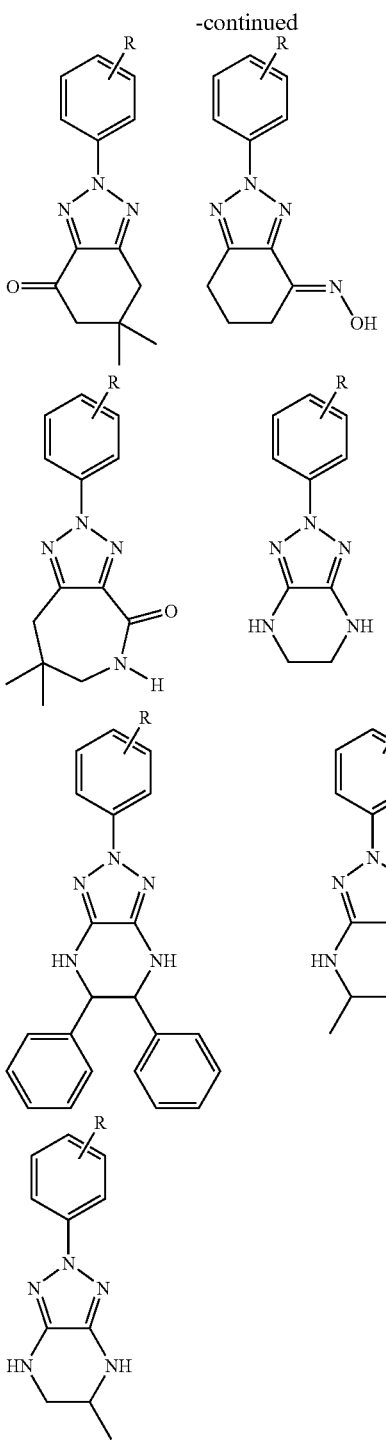

wherein R is selected from hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

Suitable triazole ligands may be prepared, for example, by hydrogenation of their unsaturated precursors (see below formula containing unsaturated ring $Q^1$), following methods known in the art. The preparation of heterocyclic derivatives such as triazolopiperazines is described in, or may follow, the procedures described for example by Sato et al., *J. Organic Chemistry* 1978, 43, 341.

Analogues of the present triazole ligands containing ring $Q^1$ (formula:

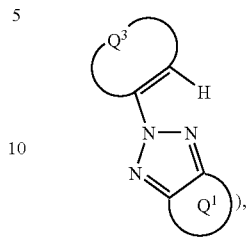

wherein $Q^1$ corresponds to $Q^2$ in the present ligand except that it is unsaturated (i.e. contains the maximum possible number of ethylenic double bonds in the ring system, as, for example, in the case of benzotriazole), are often known or can be produced according to known procedures (see, for example, WO03/105538, WO05/054212 as well as the references cited therein).

Some further procedures for the preparation of a triazole annealed via its carbon atoms to a non-aromatic ring, and useful as a triazole ligand within the present invention, are described in WO05/093007 and in Abdel Hamid et al., Egypt. Organic Preparations and Procedures International (1993), 25(5), 569-75 (CAN 120:217442).

Some of the triazole ligands useful within the present invention are novel compounds. The invention therefore also pertains to a compound of the formula

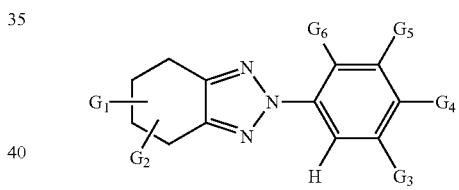

wherein $G_1$ and $G_2$, independently, are hydrogen, CN, halogen, $C_1$-$C_{12}$alkyl, $C_1$-$C_{12}$haloalkyl, $C_1$-$C_{12}$alkoxy, $C_1$-$C_{12}$alkylthio, $C_5$-$C_{12}$cycloalkyl, $C_5$-$C_{12}$cycloalkoxy, $C_5$-$C_{12}$cycloalkylthio, $C_6$-$C_{12}$aryl, $C_2$-$C_{10}$heteroaryl, $C_7$-$C_{15}$arylalkyl, $C_6$-$C_{12}$aryloxy, $C_6$-$C_{12}$arylamino;

or $G_1$ and $G_2$, bonding to vicinal atoms, together are a group of formula

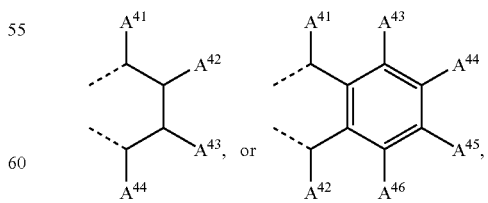

wherein $A^{41}$, $A^{42}$, $A^{43}$, $A^{44}$, $A^{45}$, $A^{46}$ and $A^{47}$ are independently of each other H, halogen, CN, $C_1$-$C_{12}$alkyl, $C_1$-$C_{12}$haloalkyl, $C_1$-$C_{12}$alkoxy, $C_1$-$C_{12}$alkylthio, $C_6$-$C_{12}$aryl; especially

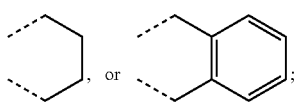

or $G_1$ and $G_2$, bonding to the same carbon atom, together are =O or =NR$^{25}$ or =N—OR$^{25}$ or =N—OH; where R$^{25}$ is $C_1$-$C_{12}$alkyl or cyclohexyl;

$G_3$, $G_4$, $G_5$ and $G_6$ independently are selected from hydrogen, $C_4$-$C_{18}$alkyl, $C_1$-$C_8$ perfluoroalkyl, fluoro;

and at least one of $G_3$, $G_4$, $G_5$ and $G_6$ is different from hydrogen;

especially one of $G_3$, $G_4$, $G_5$ and $G_6$ being CF$_3$ or F, the others being hydrogen or F.

Specific examples of

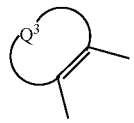

are given below in the definition of $Y^1$, $Y^2$ and $Y^3$.

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, Ma$_3$b$_3$, having octahedral geometry, in which the three "a" groups are all adjacent, i.e. at the corners of one triangular face of the octahedron. The term "meridional" is intended to mean one isomer of a complex, Ma$_3$b$_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to," when used to refer to layers in a device, does not necessarily mean that one layer is immediately next to another layer. The term "photoactive" refers to any material that exhibits electroluminescence and/or photosensitivity.

The metal is generally a metal M$^1$ with an atomic weight of greater than 40,

Preferably the metal M$^1$ is selected from the group consisting of Fe, Ru, Ni, Co, Ir, Pt, Pd, Rh, Re, Os, Tl, Pb, Bi, In, Sn, Sb, Te, Ag and Au.

More preferably the metal is selected from Ir, Rh and Re as well as Pt and Pd, wherein Ir is most preferred.

The ligand is preferably a monoanionic bidentate ligand. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).

Examples of bidentate ligands, L$^1$ or L', are

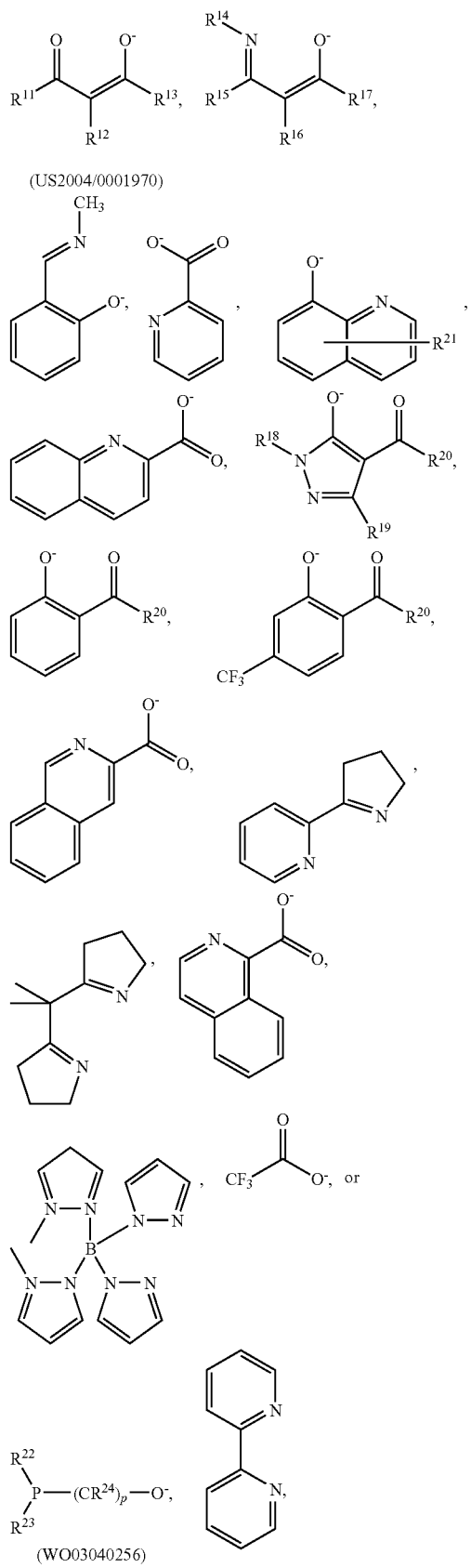

-continued

[structure: 1,2-bis(diphenylphosphino)ethane]

[structure: BINAP-type with R⁴⁶ groups]

[structure: benzothiazole with CF₃ and tert-butyl]

[structure: bis(trifluoromethylsulfonyl)imide]

O=P(Ph)(Ph)—N—P(Ph)(Ph)=O, or S=P(Ph)(Ph)—N—P(Ph)(Ph)=S, wherein $R^{11}$ and $R^{15}$ are independently of each other hydrogen, $C_1$-$C_8$alkyl, $C_6$-$C_{18}$aryl, $C_2$-$C_{10}$heteroaryl, or $C_1$-$C_8$ perfluoroalkyl, $R^{12}$ and $R^{16}$ are independently of each other hydrogen, or $C_1$-$C_8$alkyl, and $R^{13}$ and $R^{17}$ are independently of each other hydrogen, $C_1$-$C_8$alkyl, $C_6$-$C_{18}$aryl, $C_2$-$C_{10}$heteroaryl, $C_1$-$C_8$ perfluoroalkyl, or $C_1$-$C_8$alkoxy, and $R^{14}$ is $C_1$-$C_8$alkyl, $C_6$-$C_{10}$aryl, or $C_7$-$C_{11}$aralkyl, $R^{18}$ is $C_6$-$C_{10}$aryl, $R^{19}$ is $C_1$-$C_8$alkyl, $R^{20}$ is $C_1$-$C_8$alkyl, or $C_6$-$C_{10}$aryl, $R^{21}$ is hydrogen, $C_1$-$C_8$alkyl, or $C_1$-$C_8$alkoxy, which may be partially or fully fluorinated, $R^{22}$ and $R^{23}$ are independently of each other $C_n(H+F)_{2n+1}$, or $C_6(H+F)_5$, $R^{24}$ can be the same or different at each occurrence and is selected from H, or $C_n(H+F)_{2n+1}$, p is 2, or 3, and $R^{46}$ is $C_1$-$C_8$alkyl, $C_6$-$C_{18}$aryl, or $C_6$-$C_{18}$aryl, which is substituted by $C_1$-$C_8$alkyl.

Examples of suitable phosphino alkoxide ligands

[structure: $R^{22}R^{23}$P—$(CR^{24})_p$—O]

(WO03040256)

are listed below:
3-(diphenylphosphino)-1-oxypropane [dppO]
1,1-bis(trifluoromethyl)-2-(diphenylphosphino)-ethoxide [tfmdpeO].

Examples of particularly suitable compounds HL,

[structure: R¹¹C(O)CH(R¹²)C(O)R¹³]

from which the ligands L are derived, include

[structure: 2,4-pentanedione]

(2,4-pentanedionate [acac]),

[structure: 2,2-dimethyl-3,5-hexanedione]

[structure]

[structure: 2-methyl-3,5-hexanedione]

[structure: 2,2,6,6-tetramethyl-3,5-heptanedione]

(2,2,6,6-tetramethyl-3,5-heptanedionate [TMH]),

[structure: trifluoromethyl pivaloylmethane]

[structure: benzoyl pivaloylmethane]

[structure: 1,3-diphenyl-1,3-propanedione]

(1,3-diphenyl-1,3-propanedionate [DI])

[structure: trifluoro thienyl butanedione]

(4,4,4-trifluoro-1-(2-thienyl)-1,3-butanedionate [TTFA]),

[structure: trifluoro furyl butanedione]

[structure: heptafluoro octanedione]

(7,7-dimethyl-1,1,1,2,2,3,3-heptafluoro-4,6-octanedionate [FOD]),

[structure: heptafluoro pentanedione]

(1,1,1,3,5,5,5-heptafluoro-2,4-pentanedionate [F7acac]),

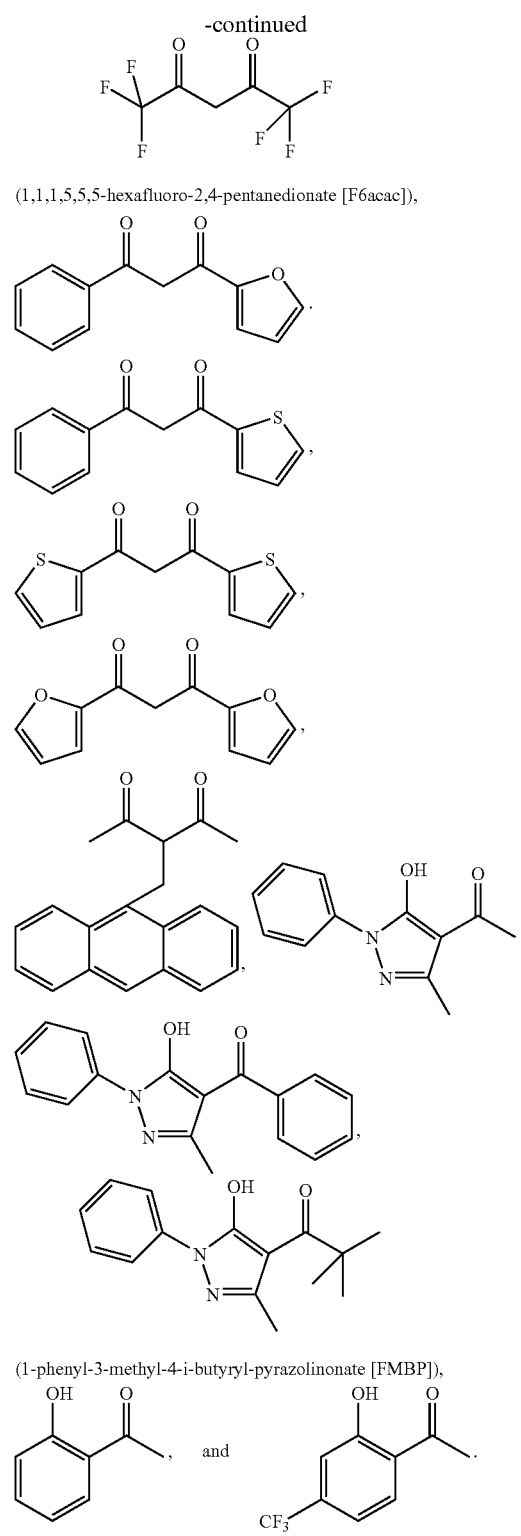

The hydroxyquinoline parent compounds, HL, can be substituted with groups such as alkyl or alkoxy groups which may be partially or fully fluorinated. In general, these compounds are commercially available. Examples of suitable hydroxyquinolinate ligands, L, include:
8-hydroxyquinolinate [8hq]
2-methyl-8-hydroxyquinolinate [Me-8hq]
O-hydroxybenzoquinolinate [10-hbq]

In a further embodiment the present invention the bidentate ligand, $L^1$, or $L'$, is a ligand of formula

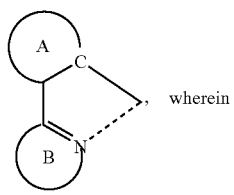 wherein the ring A,

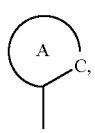

represents an optionally substituted aryl group which can optionally contain heteroatoms,
the ring B,

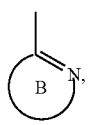

represents an optionally substituted nitrogen containing aryl group, which can optionally contain further heteroatoms, or the ring A may be taken with the ring B binding to the ring A to form a ring.

The preferred ring A includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like such as $C_1$-$C_{24}$haloalkyl.

In said embodiment the bidentate ligand

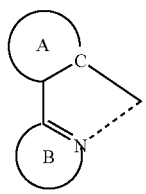

is preferably a group of formula

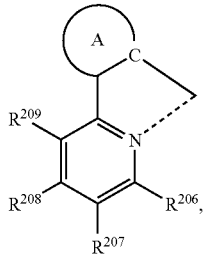

wherein $R^{206}$, $R^{207}$, $R^{208}$, and $R^{209}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{206}$, $R^{207}$, $R^{208}$, and $R^{209}$ may be substituted.

An example of a preferred class of bidentate ligands, $L^1$, $L'$ or $L''$, are compounds of the formula

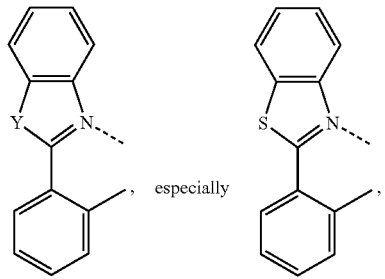

, especially wherein Y is S, O, $NR^{200}$, wherein $R^{200}$ is hydrogen, cyano, $C_1$-$C_4$alkyl, $C_2$-$C_4$alkenyl, optionally substituted $C_6$-$C_{10}$aryl, especially phenyl, —$(CH_2)_r$—Ar, wherein Ar is an optionally substituted $C_6$-$C_{10}$aryl, especially

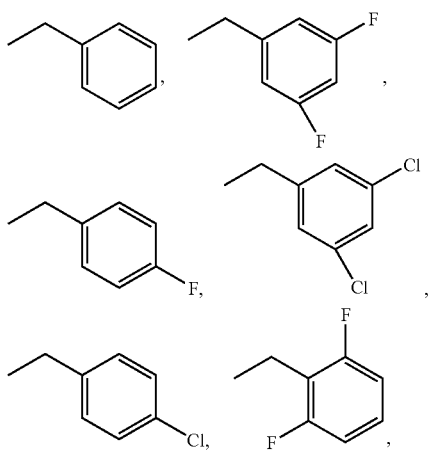

a group —$(CH_2)_{r'}X^{20}$, wherein r' is an integer of 1 to 5, $X^{20}$ is halogen, especially F, or Cl; hydroxy, cyano, —O—$C_1$-$C_4$alkyl, di($C_1$-$C_4$alkyl)amino, amino, or cyano; a group —$(CH_2)_rOC(O)(CH_2)_{r''}$—$CH_3$, wherein r is 1, or 2, and r'' is 0, or 1;

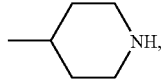

—NH-Ph, —C(O)$CH_3$, —$CH_2$—O—$(CH_2)_2$—Si$(CH_3)_3$, or

.

Another preferred class of bidentate ligands, $L^1$, $L'$ or $L''$, is a compound of formula

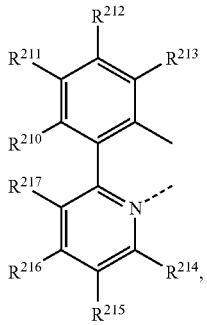

wherein $R^{214}$ is hydrogen, halogen, especially F, or Cl; nitro, $C_1$-$C_4$alkyl, $C_1$-$C_4$ perfluoroalkyl, $C_1$-$C_4$alkoxy, or optionally substituted $C_6$-$C_{10}$aryl, especially phenyl, $R^{215}$ is hydrogen, halogen, especially F, or Cl; $C_1$-$C_4$alkyl, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$, $R^{216}$ is hydrogen, $C_1$-$C_4$alkyl, $C_1$-$C_4$ perfluoroalkyl, optionally substituted $C_6$-$C_{10}$aryl, especially phenyl, or optionally substituted $C_6$-$C_{10}$ perfluoroaryl, especially $C_6F_5$,
$R^{217}$ is hydrogen, halogen, especially F, or Cl; nitro, cyano, $C_1$-$C_4$alkyl, $C_1$-$C_4$ perfluoroalkyl, $C_1$-$C_4$alkoxy, or optionally substituted $C_6$-$C_{10}$aryl, especially phenyl,
$R^{210}$ is hydrogen,
$R^{211}$ is hydrogen, halogen, especially F, or Cl; nitro, cyano, $C_1$-$C_4$alkyl, $C_2$-$C_4$alkenyl, $C_1$-$C_4$ perfluoroalkyl, —O—$C_1$-$C_4$ perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$ perfluoroaryl, especially $C_6F_5$,
$R^{212}$ is hydrogen, halogen, especially F, or Cl; nitro, hydroxy, mercapto, amino, $C_1$-$C_4$alkyl, $C_2$-$C_4$alkenyl, $C_1$-$C_4$ perfluoroalkyl, $C_1$-$C_4$alkoxy, —O—$C_1$-$C_4$ perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=CH$CO_2X^{22}$, wherein $X^{22}$ is $C_1$-$C_4$alkyl; —CH(O), —$SO_2X^{23}$, —$SOX^{23}$, —NC(O)$X^{23}$, —$NSO_2X^{23}$, —$NHX^{23}$, —N$(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$ perfluoroaryl, especially $C_6F_5$, and $R^{213}$ is hydrogen, nitro, cyano, $C_1$-$C_4$alkyl, $C_2$-$C_4$alkenyl, $C_1$-$C_4$ perfluoroalkyl, —O—$C_1$-$C_4$ perfluoroalkyl, tri($C_1$-$C_4$alkyl)silanyl, or optionally substituted $C_6$-$C_{10}$aryl, especially phenyl.
Specific examples of bidentate ligands, $L^1$, $L'$ or $L''$, are the following compounds (X-1) to (X-47):
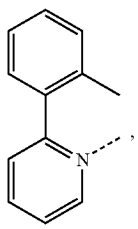
(X-1)
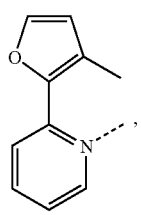
(X-2)
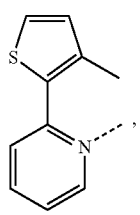
(X-3)
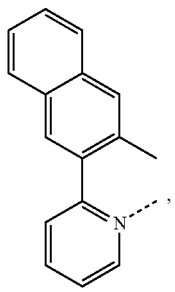
(X-4)
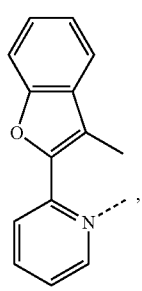
(X-5)
-continued
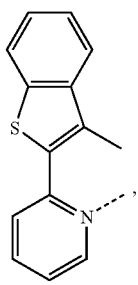
(X-6)
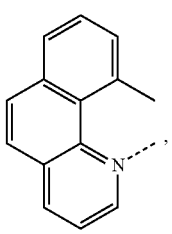
(X-7)
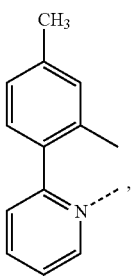
(X-8)
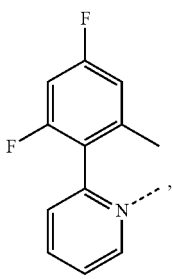
(X-9)
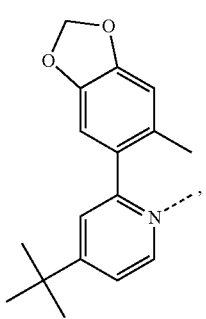
(X-10)

-continued
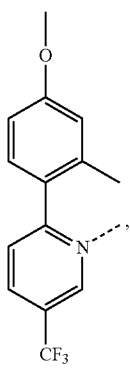
(X-11)
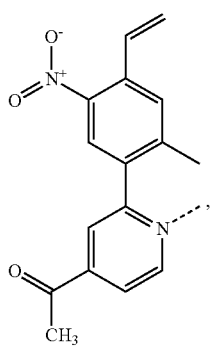
(X-12)
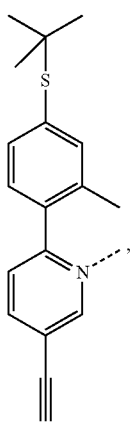
(X-13)
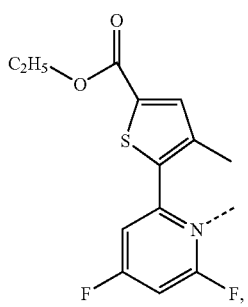
(X-14)
-continued
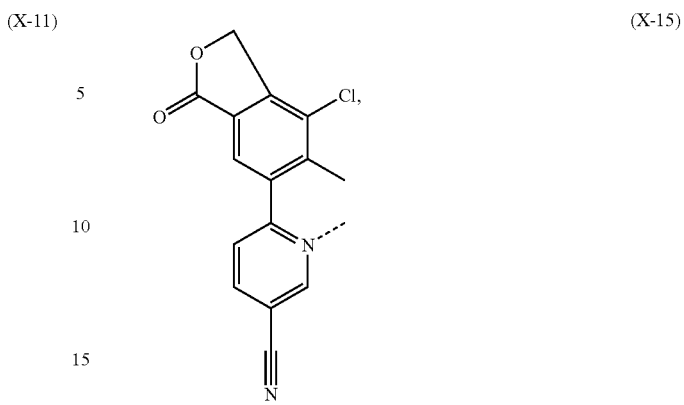
(X-15)
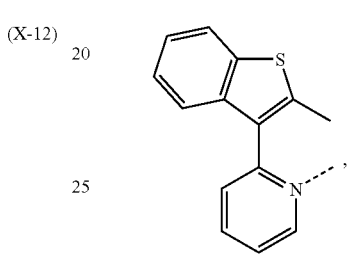
(X-16)
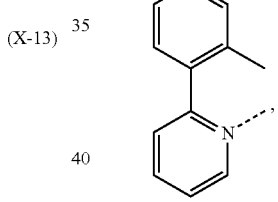
(X-17)
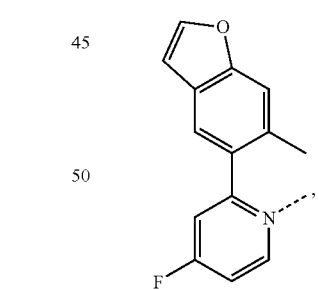
(X-18)
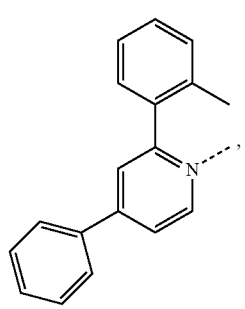
(X-19)

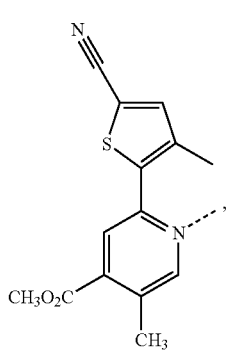
(X-20)
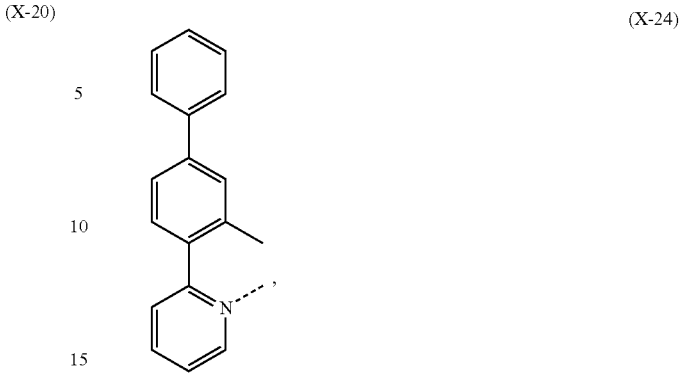
(X-24)
(X-25)
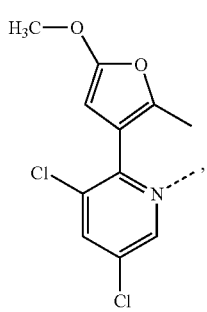
(X-21)
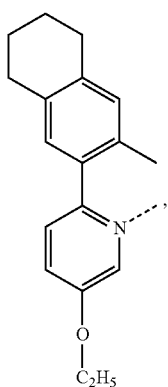
(X-22)
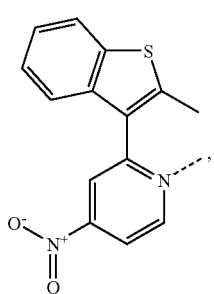
(X-23)
(X-26)
(X-27)
(X-28)

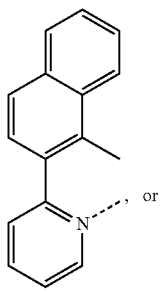
(X-29)
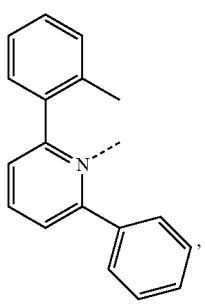
(X-30)
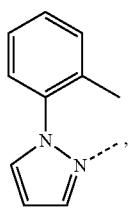
(X-31)
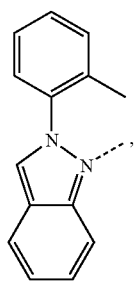
(X-32)
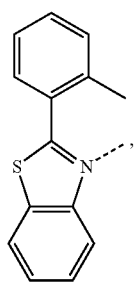
(X-33)
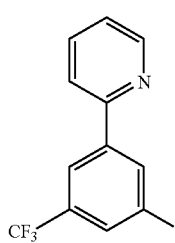
(X-34)
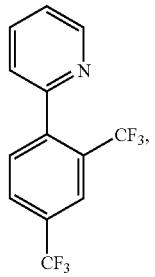
(X-35)
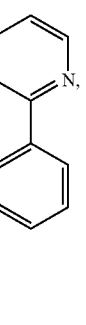
(X-36)
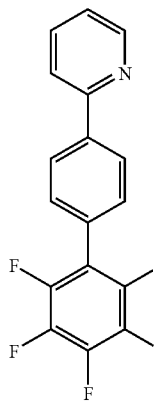
(X-37)
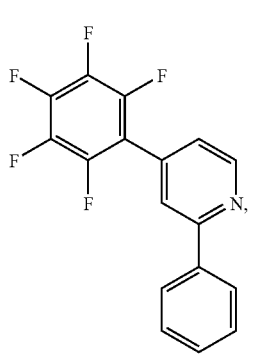
(X-37)

-continued
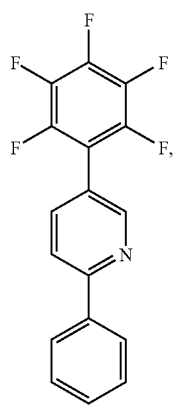
(X-38)
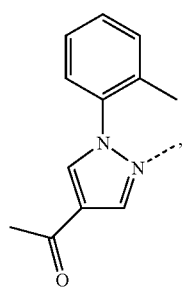
(X-39)
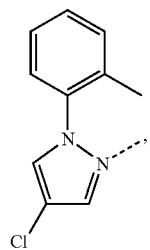
(X-40)
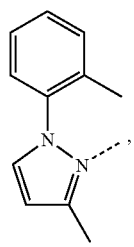
(X-41)
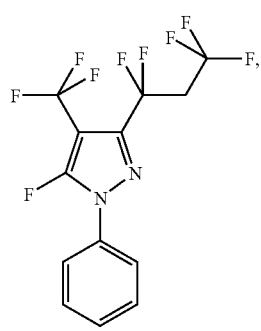
(X-42)
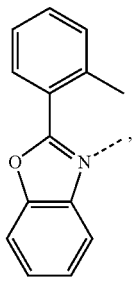
(X-43)
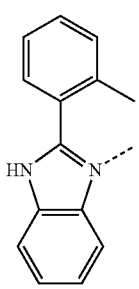
(X-44)
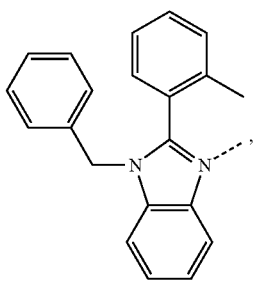
(X-45)
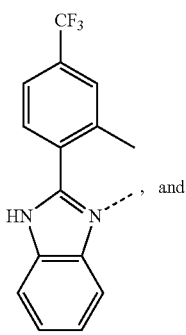
, and
(X-46)
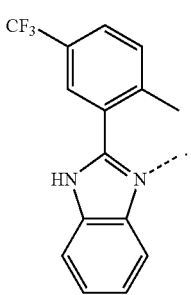
(X-47)

Another preferred class of bidentate ligands, $L^1$, L' are of the formula

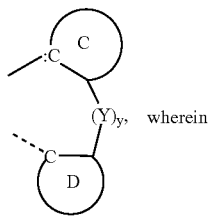

the group C,

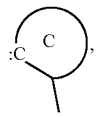

represents an acyclic carbene, or a cyclic carbene (ring C), which can optionally contain heteroatoms,
the ring D,

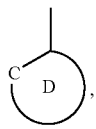

represents an optionally substituted aryl group which can optionally contain heteroatoms,
Y is —C(=O)—, or —C($X^1$)$_2$—, wherein $X^1$ is hydrogen, or $C_{1-4}$alkyl, especially hydrogen, and
y is 0, or 1, especially 0.
If the group

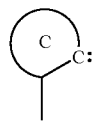

represents an acyclic nucleophilic carbene it is preferably a group of the following formula

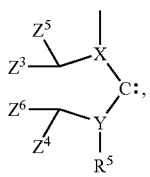

wherein X=Y=N, B, or P;

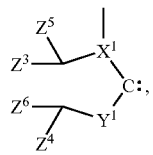

wherein $X^1$ is N, or P and $Y^1$ is S, or O; >$SiX^2X^3$, or >$CZ^5Z^3$, wherein $X^2$ and $X^3$ are independently of each other $C_1$-$C_4$alkyl and $R^5$, $Z^3$, $Z^4$, $Z^5$ and $Z^6$ are as defined below.
y is 0, or 1, especially 0. The ring D,

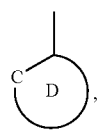

is preferably a group of formula

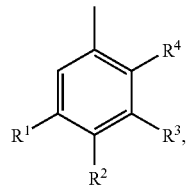

wherein $R^1$ to $R^4$ are substitutents and can be taken together to form a ring.

$R^1$, $R^2$, $R^3$ and $R^4$ are independently of each other hydrogen, halogen, especially F, or Cl; nitro, cyano, $C_1$-$C_4$alkyl, $C_1$-$C_4$ perfluoroalkyl, or $C_1$-$C_4$alkoxy, —S—$C_1$-$C_4$alkyl, —O—$C_1$-$C_4$ perfluoroalkyl, —$SO_2X^{22}$, —$CO_2H$, —$CO_2X^{22}$, wherein $X^{22}$ is $C_1$-$C_4$alkyl; $C_6H_4CF_3$, cyclohexyl, optionally substituted $C_6$-$C_{10}$aryl, especially phenyl, optionally substituted —O—$CH_2$—$C_6$-$C_{10}$aryl, especially benzyloxy, or optionally substituted —O—$C_6$-$C_{10}$aryl, especially phenoxy; $R^1$ is preferably hydrogen, halogen, especially F, or Cl; nitro, cyano, $C_1$-$C_4$alkyl, $C_1$-$C_4$ perfluoroalkyl, or $C_1$-$C_4$alkoxy.

$R^2$ is preferably hydrogen, nitro, cyano, $C_1$-$C_4$alkyl, $C_1$-$C_4$ perfluoroalkyl, $C_1$-$C_4$alkoxy, —S—$C_1$-$C_4$alkyl, —O—$C_1$-$C_4$ perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy.

$R^3$ is preferably hydrogen, nitro, cyano, $C_1$-$C_4$alkyl, $C_1$-$C_4$ perfluoroalkyl, $C_1$-$C_4$alkoxy, —S—$C_1$-$C_4$alkyl, or —O—$C_1$-$C_4$ perfluoroalkyl.

$R^4$ is preferably hydrogen.

Examples that specify the possibilities for the group designated above are as follows:

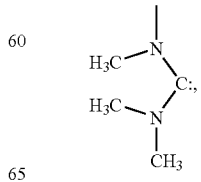 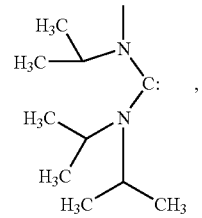

-continued

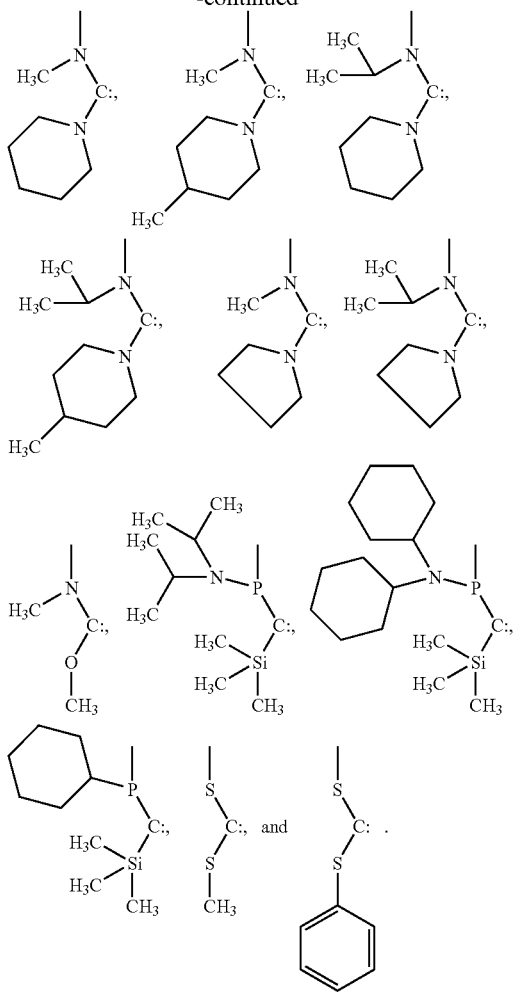

Cyclic carbenes,

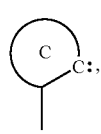
(ring C)

are preferred against acyclic carbenes. Examples of a ring C are as follows:

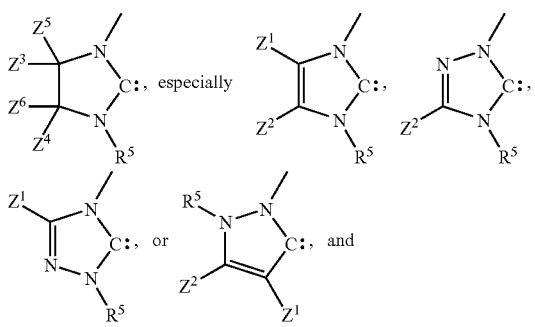

-continued

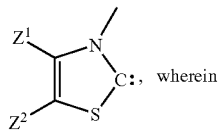, wherein $R^5$ is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy; and $Z^1$, $Z^2$, $Z^3$, $Z^4$, $Z^5$ and $Z^6$ are independently of each other selected from the group consisting of hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

In said embodiment the ligand (L¹)

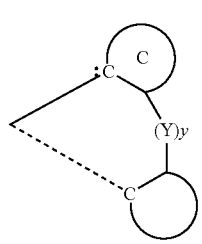

is preferably a group of formula

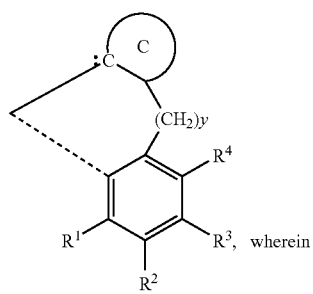, wherein $R^1$ to $R^4$ are substitutents and can be taken together to form a ring,
y is 0, or 1, especially 0,
the group C,

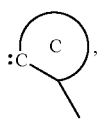

is a group (nucleophilic carbene) of the following formula

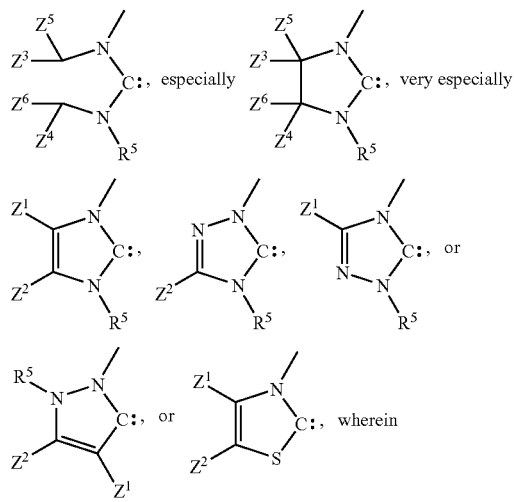

R$^5$ is a substitutent, especially hydrogen, C$_1$-C$_{24}$alkyl, C$_2$-C$_{24}$alkenyl, C$_2$-C$_{24}$alkynyl, C$_2$-C$_{24}$alkoxycarbonyl, aryl, C$_1$-C$_{24}$carboxylate, C$_1$-C$_{24}$alkoxy, C$_2$-C$_{24}$alkenyloxy, C$_2$-C$_{24}$alkynyloxy, or aryloxy, which can optionally be substituted with C$_1$-C$_8$alkyl, halogen, C$_1$-C$_8$alkoxy, or with a phenyl group, which can be substituted with halogen, C$_1$-C$_8$alkyl, or C$_1$-C$_8$alkoxy; and Z$^1$, Z$^2$, Z$^3$, Z$^4$, Z$^5$ and Z$^6$ are independently of each other selected from the group consisting of hydrogen, C$_1$-C$_{24}$alkyl, C$_2$-C$_{24}$alkenyl, C$_2$-C$_{24}$alkynyl, C$_2$-C$_{24}$alkoxycarbonyl, aryl, C$_1$-C$_{24}$carboxylate, C$_1$-C$_{24}$alkoxy, C$_2$-C$_{24}$alkenyloxy, C$_2$-C$_{24}$alkynyloxy, or aryloxy, wherein each of Z$^1$, Z$^2$, Z$^3$ and Z$^4$ optionally being substituted with C$_1$-C$_8$alkyl, halogen, C$_1$-C$_8$alkoxy, or with a phenyl group, which can optionally be substituted with halogen, C$_1$-C$_8$alkyl, or C$_1$-C$_8$alkoxy, or Z$^1$ and Z$^2$, if possible, form an aromatic or heteroaromatic ring, and/or Z$^3$, Z$^4$, Z$^5$ and Z$^6$, if possible, form an alkyl or heteroalkyl ring.

In a preferred embodiment of the present invention the compound has the formula:

w=0 or 1, x=0 or 1, y=0, 1 or 2, and z=0 or 1,

M$^2$ is Pt, Pd, Rh, Re, or Ir,

L' is a bidentate ligand or a monodentate ligand; with the proviso that: when L' is a monodentate ligand, y+z=2, and when L' is a bidentate ligand, z=0;

L" is a monodentate ligand; and

L$^a$, L$^b$ and L$^c$ are alike or different from each other and each of L$^a$, L$^b$ and L$^c$ has the structure (IIIa), (IIIb), or (IV) below:

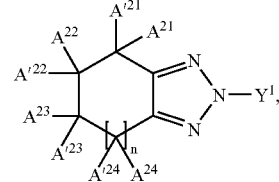

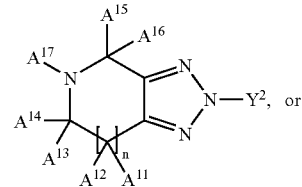

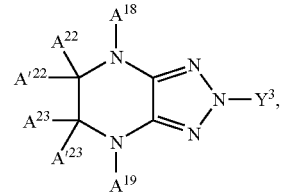

wherein n is 0, 1 or 2, especially 1;

A$^{12}$, A$^{14}$, A$^{16}$, A$^{21}$, A$^{22}$, A$^{23}$ and A$^{24}$ are independently of each other hydrogen, CN, halogen, C$_1$-C$_{24}$alkyl, C$_1$-C$_{24}$alkoxy, C$_1$-C$_{24}$alkylthio, C$_1$-C$_{24}$ perfluoroalkyl, C$_6$-C$_{18}$aryl, which is optionally substituted by G; —NR$^{25}$R$^{26}$, —CONR$^{25}$R$^{26}$, or —COOR$^{27}$, or C$_2$-C$_{10}$heteroaryl, which is optionally substituted by G; or C$_5$-C$_{12}$cycloalkyl, C$_5$-C$_{12}$cycloalkoxy, C$_5$-C$_{12}$cycloalkylthio, each of which is optionally substituted by G; especially a group of formula

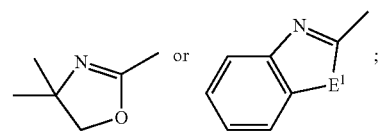

or 2 adjacent radicals A$^{12}$, A$^{14}$; or A$^{14}$, A$^{17}$; or A$^{17}$, A$^{16}$; or A$^{21}$, A$^{22}$; or A$^{22}$, A$^{23}$; or A$^{23}$, A$^{24}$; or A$^{18}$, A$^{22}$; or A$^{23}$, A$^{19}$, bonding to vicinal atoms, together are a group of formula

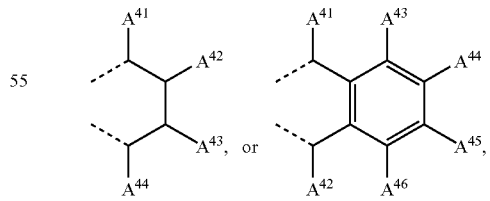

wherein A$^{41}$, A$^{42}$, A$^{43}$, A$^{44}$, A$^{45}$, A$^{46}$ and A$^{47}$ are independently of each other H, halogen, CN, C$_1$-C$_{24}$alkyl, C$_1$-C$_{24}$ perfluoroalkyl, C$_1$-C$_{24}$alkoxy, C$_1$-C$_{24}$alkylthio, C$_6$-C$_{18}$aryl, which may optionally be substituted by G, —NR$^{25}$R$^{26}$, —CONR$^{25}$R$^{26}$, or —COOR$^{27}$, or C$_2$-C$_{10}$heteroaryl; especially

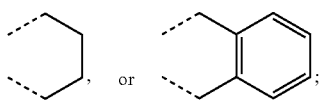

while each of $A^{11}$, $A^{13}$, $A^{15}$, $A'^{21}$, $A'^{22}$, $A'^{23}$ and $A'^{24}$ independently is hydrogen or $C_1$-$C_{24}$alkyl;

or 2 adjacent radicals $A^{11}$, $A^{12}$; $A^{13}$, $A^{14}$; $A^{15}$, $A^{16}$; $A'^{21}$, $A^{21}$; $A'^{22}$, $A^{22}$; $A'^{23}$, $A^{23}$; $A'^{24}$, $A^{24}$, bonding to the same carbon atom, together are =O or =NR$^{25}$ or =N—OR$^{25}$ or =N—OH;

$E^1$ is O, S, or NR$^{25}$, $R^{25}$ and $R^{26}$ are independently of each other $C_6$-$C_{18}$aryl, $C_7$-$C_{18}$aralkyl, or $C_1$-$C_{24}$alkyl or $C_5$-$C_{12}$cycloalkyl, $R^{27}$ is $C_1$-$C_{24}$alkyl, $C_6$-$C_{18}$aryl, or $C_7$-$C_{18}$aralkyl; and $Y^1$, $Y^2$ and $Y^3$ are independently of each other a group of formula

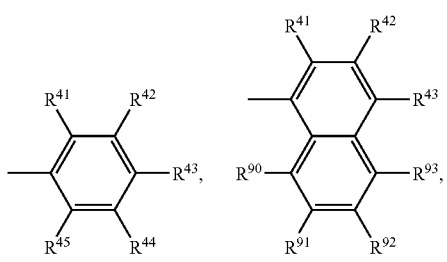

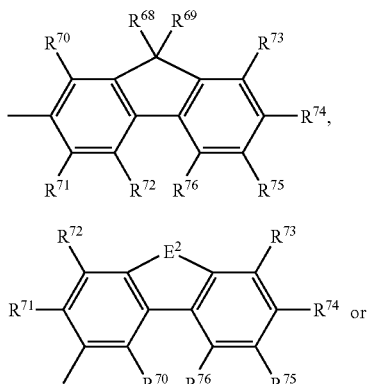

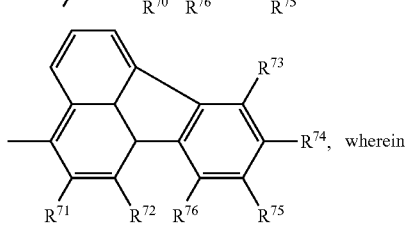

$R^{41}$ is the bond to $M^2$, $R^{71}$ is the bond to $M^2$, $R^{42}$ is hydrogen, or $C_1$-$C_{24}$alkyl, CN, $C_1$-$C_{24}$alkyl, which is substituted by F, halogen, especially F, $C_6$-$C_{18}$-aryl, $C_6$-$C_{18}$-aryl which is substituted by $C_1$-$C_{12}$alkyl, or $C_1$-$C_8$alkoxy, $R^{43}$ is hydrogen, CN, halogen, especially F, $C_1$-$C_{24}$alkyl, which is substituted by F, $C_6$-$C_{18}$aryl, $C_6$-$C_{18}$aryl which is substituted by $C_1$-$C_{12}$alkyl, or $C_1$-$C_8$alkoxy, —CONR$^{25}$R$^{26}$, —COOR$^{27}$,

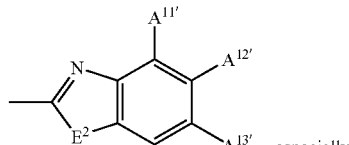, especially

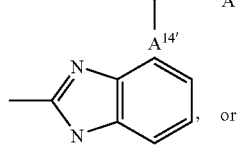, or

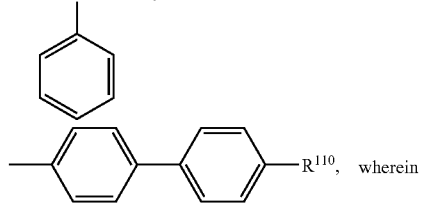, wherein $E^2$ is —S—, —O—, or —NR$^{25'}$—, wherein $R^{25'}$ is $C_1$-$C_{24}$alkyl, or $C_6$-$C_{10}$aryl, $R^{110}$ is H, CN, $C_1$-$C_{24}$alkyl, $C_1$-$C_{24}$alkoxy, $C_1$-$C_{24}$alkylthio, —NR$^{25}$R$^{26}$, —CONR$^{25}$R$^{26}$, or —COOR$^{27}$, or $R^{42}$ and $R^{43}$ are a group of formula

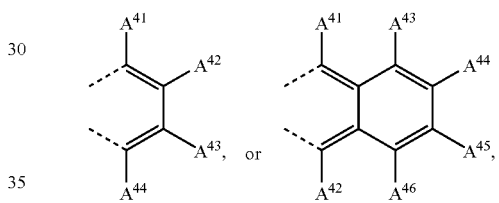

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —NR$^{25}$R$^{26}$, —CONR$^{25}$R$^{26}$, or —COOR$^{27}$, or $C_2$-$C_{10}$heteroaryl; especially

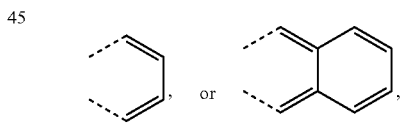

$R^{44}$ is hydrogen, CN or $C_1$-$C_{24}$alkyl, $C_1$-$C_{24}$alkyl, which is substituted by F, halogen, especially F, $C_6$-$C_{18}$-aryl, $C_6$-$C_{18}$-aryl which is substituted by $C_1$-$C_{12}$ alkyl, or $C_1$-$C_8$alkoxy, $R^{45}$ is hydrogen, CN or $C_1$-$C_{24}$alkyl, $C_1$-$C_{24}$alkyl, which is substituted by F, halogen, especially F, $C_6$-$C_{18}$-aryl, $C_6$-$C_{18}$-aryl which is substituted by $C_1$-$C_{12}$ alkyl, or $C_1$-$C_8$alkoxy, $A^{11'}$, $A^{12'}$, $A^{13'}$, and $A^{14'}$ are independently of each other H, halogen, CN, $C_1$-$C_{24}$alkyl, $C_1$-$C_{24}$alkoxy, $C_1$-$C_{24}$alkylthio, —NR$^{25}$R$^{26}$, —CONR$^{25}$R$^{26}$, or —COR$^{27}$, $R^{68}$ and $R^{69}$ are independently of each other $C_1$-$C_{24}$alkyl, especially $C_4$-$C_{12}$alkyl, especially hexyl, heptyl, 2-ethylhexyl, and octyl, which can be interrupted by one or two oxygen atoms, $R^{70}$, $R^{72}$, $R^{73}$, $R^{74}$, $R^{75}$, $R^{76}$, $R^{90}$, $R^{91}$, $R^{92}$, and $R^{93}$ are independently of each other H, halogen, especially F, CN, $C_1$-$C_{24}$alkyl, $C_6$-$C_{10}$aryl, $C_1$-$C_{24}$alkoxy, $C_1$-$C_{24}$alkylthio, —NR$^{25}$R$^{26}$, —CONR$^{25}$R$^{26}$, or —COOR$^{27}$, wherein $R^{25}$, $R^{26}$ and $R^{27}$ are as defined above and G is $C_1$-$C_{18}$alkyl, —$OR^{305}$, —$SR^{305}$, —$NR^{305}R^{306}$, —$CONR^{305}R^{306}$ or —CN, wherein $R^{305}$ and $R^{306}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl, or $C_1$-$C_{18}$alkyl which is interrupted by —O—; or $R^{305}$ and $R^{306}$ together form a five or six membered ring, in particular

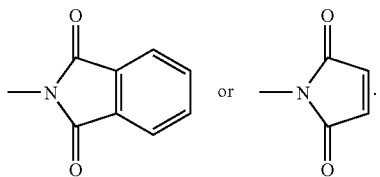

Preferred are those compounds, wherein the central metal atom (e.g. $M^1$, or $M^2$ or $M^3$; especially Ir) is six-fold coordinated by the ligands present in the complex, i.e.

the complex contains 1 bidentate ligand and 4 monodentate ligands, or the complex contains 2 bidentate ligands and 2 monodentate ligands, or, preferably, the complex contains 3 bidentate ligands and no monodentate ligand.

Also preferred are compounds, wherein the central metal atom (e.g. $M^1$, or $M^2$ or $M^3$; especially Pd, Pt) is 4-fold coordinated by the ligands present in the complex, i.e.

the complex contains 1 bidentate ligand and 2 monodentate ligands, or the complex contains 2 bidentate ligands and no monodentate ligand.

In said embodiment compounds are more preferred, wherein w=1, x=1, y=0, and z=0, and wherein w=1, x=0, y=1 and z=0, or those having the structure (Va), (Vb), (Vc), (Vd), (Ve), (Vf) or (Vg):

(Va)

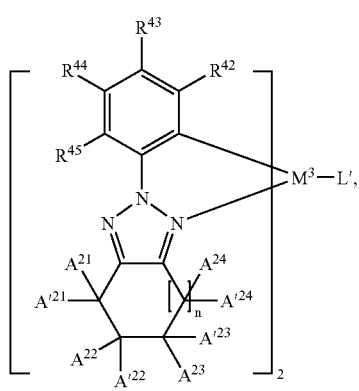

(Vb)

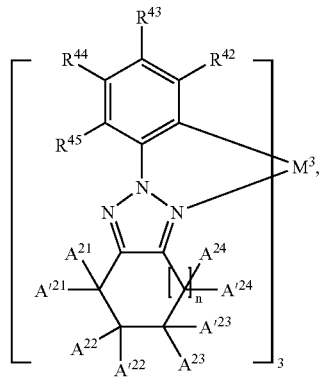

(Vc)

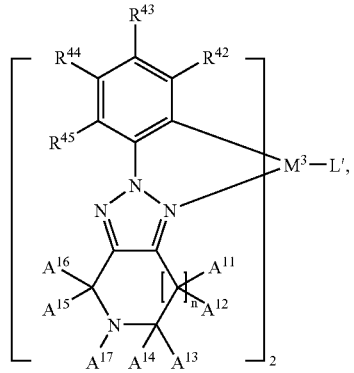

(Vd)

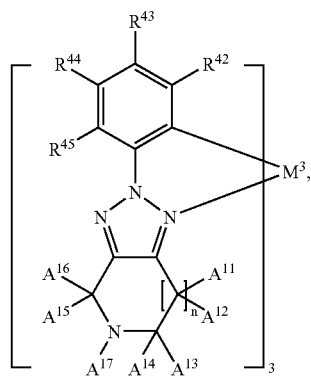

(Ve)

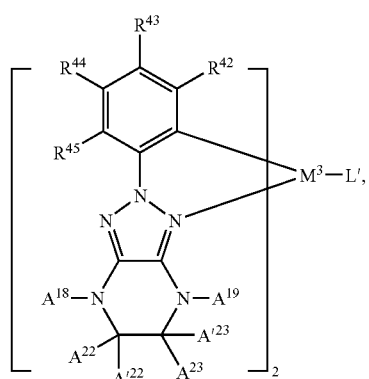

-continued

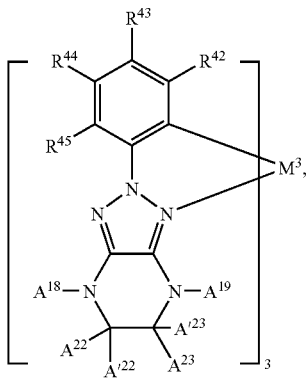

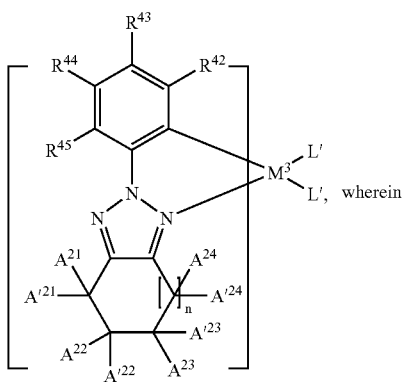

$M^3$ is Rh, or Re, especially Ir,
n is 0, 1 or 2, especially 1;
$A^{12}, A^{14}, A^{16}, A^{21}, A^{22}, A^{23}$ and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$ perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G; especially a group of formula

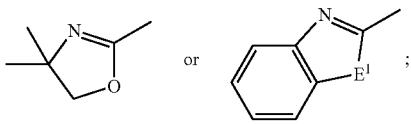

or 2 adjacent radicals $A^{12}, A^{14}$; or $A^{14}, A^{17}$; or $A^{17}, A^{16}$; or $A^{21}, A^{22}$; or $A^{22}, A^{23}$; or $A^{23}, A^{24}$; or $A^{18}, A^{22}$; or $A^{23}, A^{19}$, bonding to vicinal atoms, together are a group of formula

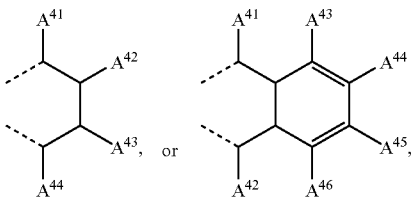

wherein $A^{41}, A^{42}, A^{43}, A^{44}, A^{45}, A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$, or —$COOR^{27}$, or $C_2$-$C_{10}$heteroaryl; especially

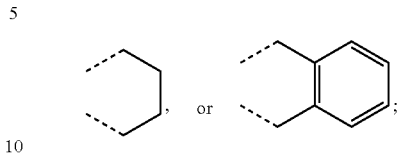

while each $A^{11}, A^{13}, A^{15}, A^{'21}, A^{'22}, A^{'23}$ and $A^{'24}$ independently is hydrogen or $C_1$-$C_{24}$alkyl;
or 2 adjacent radicals $A^{11}, A^{12}; A^{13}, A^{14}; A^{15}, A^{16}; A^{'21}, A^{21}; A^{'22}, A^{22}; A^{'23}, A^{23}; A^{'24}, A^{24}$, bonding to the same carbon atom, together are =O or =$NR^{25}$;
L' is a bidentate ligand selected from

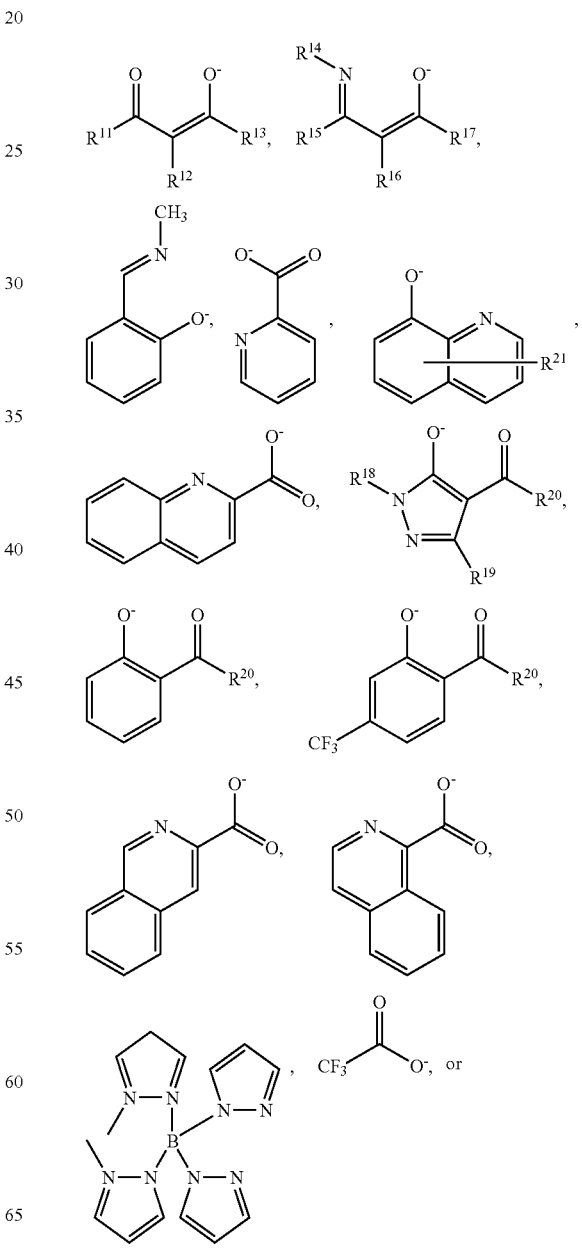

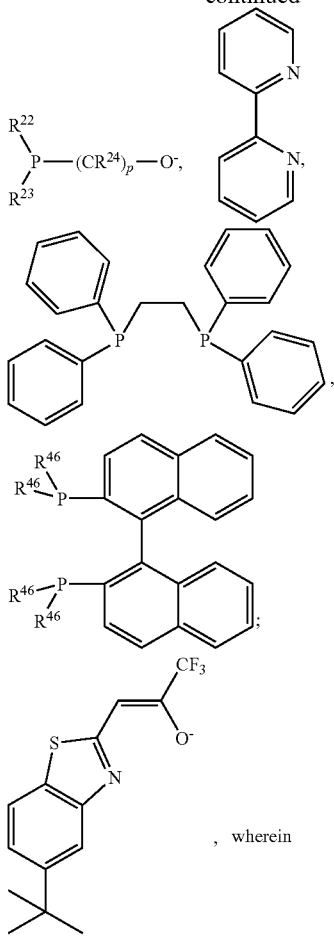
, wherein $R^{11}$ and $R^{15}$ are independently of each other hydrogen, $C_1$-$C_8$alkyl, $C_6$-$C_{18}$aryl, $C_2$-$C_{10}$heteroaryl, or $C_1$-$C_8$ perfluoroalkyl, $R^{12}$ and $R^{16}$ are independently of each other hydrogen, or $C_1$-$C_8$alkyl, and $R^{13}$ and $R^{17}$ are independently of each other hydrogen, $C_1$-$C_8$alkyl, $C_6$-$C_{18}$aryl, $C_2$-$C_{10}$heteroaryl, $C_1$-$C_8$ perfluoroalkyl, or $C_1$-$C_8$alkoxy, and $R^{14}$ is $C_1$-$C_8$alkyl, $C_6$-$C_{10}$aryl, or $C_7$-$C_{11}$aralkyl, $R^{18}$ is $C_6$-$C_{10}$aryl, $R^{19}$ is $C_1$-$C_8$alkyl, $R^{20}$ is $C_1$-$C_8$alkyl, or $C_6$-$C_{10}$aryl, $R^{21}$ is hydrogen, $C_1$-$C_8$alkyl, or $C_1$-$C_8$alkoxy, which may be partially or fully fluorinated, $R^{22}$ and $R^{23}$ are independently of each other $C_n(H+F)_{2n+1}$, or $C_6(H+F)_5$, $R^{24}$ can be the same or different at each occurrence and is selected from H, or $C_n(H+F)_{2n+1}$, p is 2, or 3

$R^{42}$ is H, F, $C_1$-$C_4$alkyl, $C_1$-$C_8$alkoxy, or $C_1$-$C_4$ perfluoroalkyl, $R^{43}$ is H, F, $C_1$-$C_4$alkyl, $C_1$-$C_4$ perfluoroalkyl, $C_1$-$C_8$alkoxy, or $C_6$-$C_{10}$aryl, $R^{44}$ is H, F, $C_1$-$C_{12}$alkyl, $C_7$-$C_{15}$phenylalkyl, $C_1$-$C_8$alkoxy, or $C_1$-$C_4$ perfluoroalkyl, $R^{45}$ is H, F, $C_1$-$C_4$alkyl, $C_1$-$C_8$alkoxy, or $C_1$-$C_4$ perfluoroalkyl, and $R^{46}$ is $C_1$-$C_8$alkyl, $C_6$-$C_{18}$aryl, $C_1$-$C_8$alkoxy, or $C_6$-$C_{18}$aryl, which is substituted by $C_1$-$C_8$alkyl, or the bidentate ligand L' is a ligand of formula (L'')

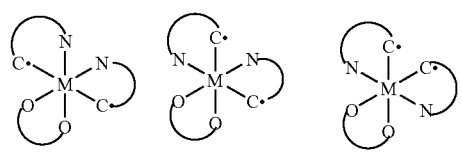

very especially a compound (X-1) to (X-47) as described above.

In some compounds of specific interest, $A^{11}$ and $A^{12}$ independently are hydrogen or $C_1$-$C_4$alkyl, especially hydrogen, $A^{13}$ is hydrogen, $A^{14}$ is hydrogen, $A^{15}$ is hydrogen and $A^{16}$ is hydrogen, or $A^{15}$ and $A^{16}$ together are oxo, $A^{17}$ is hydrogen or $C_1$-$C_4$alkyl, $A^{18}$ and $A^{19}$ independently are hydrogen or $C_1$-$C_4$alkyl, $A^{21}$ is hydrogen, $C_1$-$C_4$alkyl, phenyl, phenylamino and $A'^{21}$ is hydrogen or $C_1$-$C_4$alkyl, or $A^{21}$ and $A'^{21}$ together are oxo, hydroxyimino or $C_1$-$C_4$alkoxyimino, $A^{22}$ is hydrogen, $C_1$-$C_4$alkyl, phenylamino or $C_6$-$C_{10}$aryl, $A'^{22}$ is hydrogen, $A^{23}$ is hydrogen, $C_1$-$C_4$alkyl, phenylamino or $C_6$-$C_{10}$aryl, $A'^{23}$ is hydrogen or $C_1$-$C_4$alkyl, $A^{24}$ and $A'^{24}$ each is hydrogen, $R^{42}$ is H, F, $C_1$-$C_4$alkyl, $C_1$-$C_8$alkoxy, or $C_1$-$C_4$ perfluoroalkyl, $R^{43}$ is H, F, $C_1$-$C_4$alkyl, $C_1$-$C_4$ perfluoroalkyl, $C_1$-$C_8$alkoxy, or $C_6$-$C_{10}$aryl, $R^{44}$ is H, F, $C_1$-$C_{12}$alkyl, $C_7$-$C_{15}$phenylalkyl, $C_1$-$C_8$alkoxy, or $C_1$-$C_4$ perfluoroalkyl, $R^{45}$ is H, F, $C_1$-$C_4$alkyl, $C_1$-$C_8$alkoxy, or $C_1$-$C_4$ perfluoroalkyl.

In case of the metal complex $(L^a)_2ML'$ three isomers can exist (M being the central atom, e.g. Ir):

In some cases mixtures of isomers are obtained. Often the mixture can be used without isolating the individual isomers.

Some of the presently most preferred compounds are shown below, with symbols as previously defined or especially as listed:

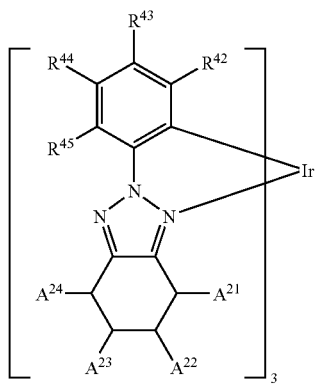

| Cpd. | R45 | R44 | R43 | R42 | A24 | A23 | A22 | A21 |
|---|---|---|---|---|---|---|---|---|
| A-1 | H | H | H | H | H | H | H | H |
| A-2 | F | H | H | H | H | H | H | H |
| A-3 | H | H | F | H | H | H | H | H |
| A-4 | H | F | F | H | H | H | H | H |
| A-5 | F | H | H | F | H | H | H | H |
| A-6 | H | H | CF3 | H | H | H | H | H |
| A-7 | H | CF3 | H | CF3 | H | H | H | H |
| A-8 | CF3 | H | H | H | H | H | H | H |
| A-9 | H | CH3 | H | CH3 | H | H | H | H |
| A-10 | H | H | CH3 | H | H | H | H | H |
| A-11 | H | H | Ph | H | H | H | H | H |
| A-12 | H | H | OMe | H | H | H | H | H |
| A-13 | CH3 | CH3 | H | H | H | H | H | H |
| A-14 | CH3 | H | CH3 | H | H | H | H | H |
| A-15 | H | H | Ph | H | H | H/Ph[1] | Ph/H[1] | H |
| A-16 | H | H | t-Bu | H | H | H | H | H |
| A-17 | H | [2] | H | H | H | H | H | H |

[1] mixture of isomers.
[2] 2,4,4-trimethylpent-2-yl.

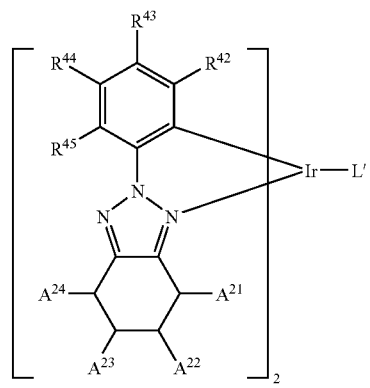

| Cpd. | L' | R45 | R44 | R43 | R42 | A24 | A23 | A22 | A21 |
|---|---|---|---|---|---|---|---|---|---|
| B-1 | A[2] | H | H | H | H | H | H | H | H |
| B-2 | A[2] | F | H | H | H | H | H | H | H |
| B-3 | A[2] | H | H | F | H | H | H | H | H |
| B-4 | A[2] | H | F | F | H | H | H | H | H |
| B-5 | A[2] | F | H | H | F | H | H | H | H |
| B-6 | A[2] | H | H | CF3 | H | H | H | H | H |
| B-7 | A[2] | H | CF3 | H | CF3 | H | H | H | H |
| B-8 | A[2] | CF3 | H | H | H | H | H | H | H |
| B-9 | A[2] | H | CH3 | H | CH3 | H | H | H | H |
| B-10 | A[2] | H | H | CH3 | H | H | H | H | H |
| B-11 | A[2] | H | H | Ph | H | H | H | H | H |
| B-12 | A[2] | H | H | OMe | H | H | H | H | H |
| B-13 | A[2] | CH3 | CH3 | H | H | H | H | H | H |
| B-14 | A[2] | CH3 | H | CH3 | H | H | H | H | H |
| B-15 | A[2] | H | H | Ph | H | H | H/Ph[1] | Ph/H[1] | H |
| B-16 | A[2] | H | H | t-Bu | H | H | H | H | H |
| B-17 | B[2] | H | H | H | H | H | H | H | H |
| B-18 | B[2] | F | F | H | H | H | H | H | H |
| B-19 | B[2] | H | H | H | F | H | H | H | H |
| B-20 | B[2] | F | F | F | F | H | H | H | H |
| B-21 | B[2] | F | F | H | H | F | H | H | H |
| B-22 | B[2] | H | H | CF3 | H | H | H | H | H |
| B-23 | B[2] | H | H | CF3 | H | CF3 | H | H | H |
| B-24 | B[2] | CF3 | CF3 | H | H | H | H | H | H |
| B-25 | B[2] | H | H | CH3 | H | CH3 | H | H | H |
| B-26 | B[2] | H | H | H | CH3 | H | H | H | H |
| B-27 | B[2] | H | H | Ph | H | H | H | H | H |
| B-28 | B[2] | H | H | OMe | H | H | H | H | H |
| B-29 | B[2] | CH3 | CH3 | CH3 | H | H | H | H | H |
| B-30 | B[2] | CH3 | CH3 | H | CH3 | H | H | H | H |
| B-31 | B[2] | H | H | Ph | H | H | H/Ph[1] | Ph/H[1] | H |
| B-32 | B[2] | H | H | t-Bu | H | H | H | H | H |
| B-33 | C[2] | H | H | H | H | H | H | H | H |
| B-34 | C[2] | F | H | H | H | H | H | H | H |
| B-35 | C[2] | H | H | F | H | H | H | H | H |
| B-36 | C[2] | F | F | H | H | H | H | H | H |
| B-37 | C[2] | H | F | F | H | H | H | H | H |
| B-38 | C[2] | H | H | CF3 | H | H | H | H | H |
| B-39 | C[2] | H | CF3 | H | CF3 | H | H | H | H |
| B-40 | C[2] | CF3 | H | H | H | H | H | H | H |
| B-41 | C[2] | H | CH3 | H | CH3 | H | H | H | H |
| B-42 | C[2] | H | H | CH3 | H | H | H | H | H |
| B-43 | C[2] | H | H | Ph | H | H | H | H | H |
| B-44 | C[2] | H | H | OMe | H | H | H | H | H |
| B-45 | C[2] | CH3 | CH3 | H | H | H | H | H | H |
| B-46 | C[2] | CH3 | H | CH3 | H | H | H | H | H |
| B-47 | C[2] | H | H | Ph | H | H | H/Ph[1] | Ph/H[1] | H |
| B-48 | C[2] | H | H | t-Bu | H | H | H | H | H |
| B-49 | D[2] | H | H | H | H | H | H | H | H |
| B-50 | D[2] | F | H | H | H | H | H | H | H |
| B-51 | D[2] | H | H | F | H | H | H | H | H |
| B-52 | D[2] | H | F | F | H | H | H | H | H |
| B-53 | D[2] | F | H | H | F | H | H | H | H |
| B-54 | D[2] | H | H | CF3 | H | H | H | H | H |
| B-55 | D[2] | H | CF3 | H | CF3 | H | H | H | H |
| B-56 | D[2] | CF3 | H | H | H | H | H | H | H |
| B-57 | D[2] | H | CH3 | H | CH3 | H | H | H | H |
| B-58 | D[2] | H | H | CH3 | H | H | H | H | H |
| B-59 | D[2] | H | H | Ph | H | H | H | H | H |
| B-60 | D[2] | H | H | OMe | H | H | H | H | H |
| B-61 | D[2] | CH3 | CH3 | H | H | H | H | H | H |
| B-62 | D[2] | CH3 | H | CH3 | H | H | H | H | H |
| B-63 | D[2] | H | H | Ph | H | H | H/Ph[1] | Ph/H[1] | H |
| B-64 | D[2] | H | H | t-Bu | H | H | H | H | H |
| B-65 | A | H | [3] | H | H | H | H | H | H |
| B-66 | B | H | [3] | H | H | H | H | H | H |
| B-67 | C | H | [3] | H | H | H | H | H | H |
| B-68 | D | H | [3] | H | H | H | H | H | H |

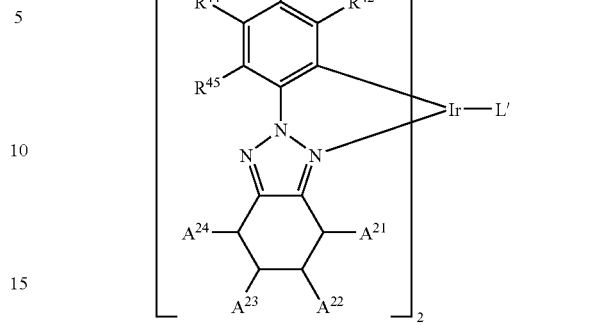

-continued

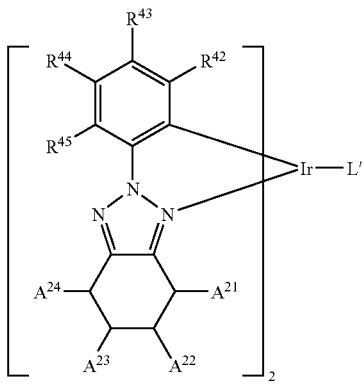

| Cpd. | L' | R45 | R44 | R43 | R42 | A24 | A23 | A22 | A21 |
|---|---|---|---|---|---|---|---|---|---|

1) mixture of isomers.
2) A = 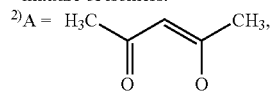

B = 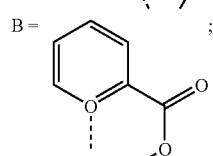

C = 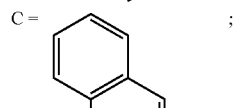

D = 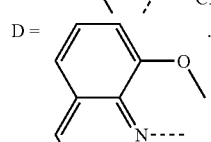

3) 2,4,4-trimethylpent-2-yl.

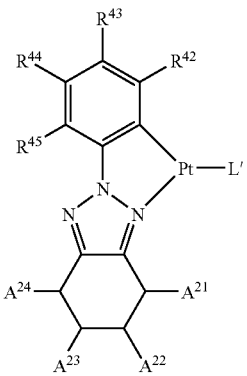

| Cpd. | L' | R45 | R44 | R43 | R42 | A24 | A23 | A22 | A21 |
|---|---|---|---|---|---|---|---|---|---|
| H-1 | A[2] | H | H | H | H | H | H | H | H |
| H-2 | A[2] | F | H | H | H | H | H | H | H |
| H-3 | A[2] | H | H | F | H | H | H | H | H |
| H-4 | A[2] | F | H | F | H | H | H | H | H |

-continued

| Cpd. | L' | R45 | R44 | R43 | R42 | A24 | A23 | A22 | A21 |
|---|---|---|---|---|---|---|---|---|---|
| H-5 | A[2] | F | H | H | F | H | H | H | H |
| H-6 | A[2] | H | H | CF3 | H | H | H | H | H |
| H-7 | A[2] | H | CF3 | H | CF3 | H | H | H | H |
| H-8 | A[2] | CF3 | H | H | H | H | H | H | H |
| H-9 | A[2] | H | CH3 | H | CH3 | H | H | H | H |
| H-10 | A[2] | H | H | CH3 | H | H | H | H | H |
| H-11 | A[2] | H | H | Ph | H | H | H | H | H |
| H-12 | A[2] | H | H | OMe | H | H | H | H | H |
| H-13 | A[2] | CH3 | CH3 | H | H | H | H | H | H |
| H-14 | A[2] | CH3 | H | CH3 | H | H | H | H | H |
| H-15 | A[2] | H | H | Ph | H | H | H/Ph[1] | Ph/H[1] | H |
| H-16 | A[2] | H | t-Bu | H | H | H | H | H | H |
| H-17 | B[2] | H | H | H | H | H | H | H | H |
| H-18 | B[2] | F | F | H | H | H | H | H | H |
| H-19 | B[2] | H | H | F | H | H | H | H | H |
| H-20 | B[2] | F | H | F | H | H | H | H | H |
| H-21 | B[2] | F | F | H | H | F | H | H | H |
| H-22 | B[2] | H | H | H | CF3 | H | H | H | H |
| H-23 | B[2] | H | H | CF3 | H | CF3 | H | H | H |
| H-24 | B[2] | CF3 | H | H | H | H | H | H | H |
| H-25 | B[2] | H | H | CH3 | H | CH3 | H | H | H |
| H-26 | B[2] | H | H | H | CH3 | H | H | H | H |
| H-27 | B[2] | H | H | H | Ph | H | H | H | H |
| H-28 | B[2] | H | H | H | OMe | H | H | H | H |
| H-29 | B[2] | CH3 | CH3 | CH3 | H | H | H | H | H |
| H-30 | B[2] | CH3 | CH3 | H | CH3 | H | H | H | H |
| H-31 | B[2] | H | H | H | Ph | H | H | H/Ph[1] | Ph/H[1] |
| H-32 | B[2] | H | H | t-Bu | H | H | H | H | H |
| H-33 | C[2] | H | H | H | H | H | H | H | H |
| H-34 | C[2] | F | H | H | H | H | H | H | H |
| H-35 | C[2] | H | H | F | H | H | H | H | H |
| H-36 | C[2] | F | F | H | H | H | H | H | H |
| H-37 | C[2] | F | H | F | H | H | H | H | H |
| H-38 | C[2] | H | H | CF3 | H | H | H | H | H |
| H-39 | C[2] | H | CF3 | H | CF3 | H | H | H | H |
| H-40 | C[2] | CF3 | H | H | H | H | H | H | H |
| H-41 | C[2] | H | CH3 | H | CH3 | H | H | H | H |
| H-42 | C[2] | H | H | CH3 | H | H | H | H | H |
| H-43 | C[2] | H | H | Ph | H | H | H | H | H |
| H-44 | C[2] | H | H | OMe | H | H | H | H | H |
| H-45 | C[2] | CH3 | CH3 | H | H | H | H | H | H |
| H-46 | C[2] | CH3 | H | CH3 | H | H | H | H | H |
| H-47 | C[2] | H | H | Ph | H | H | H/Ph[1] | Ph/H[1] | H |
| H-48 | C[2] | H | t-Bu | H | H | H | H | H | H |
| H-49 | D[2] | H | H | H | H | H | H | H | H |
| H-50 | D[2] | F | H | H | H | H | H | H | H |
| H-51 | D[2] | H | H | F | H | H | H | H | H |
| H-52 | D[2] | F | F | H | H | H | H | H | H |
| H-53 | D[2] | F | H | F | H | H | H | H | H |
| H-54 | D[2] | H | H | CF3 | H | H | H | H | H |
| H-55 | D[2] | H | CF3 | H | CF3 | H | H | H | H |
| H-56 | D[2] | CF3 | H | H | H | H | H | H | H |
| H-57 | D[2] | H | CH3 | H | CH3 | H | H | H | H |
| H-58 | D[2] | H | H | CH3 | H | H | H | H | H |
| H-59 | D[2] | H | H | Ph | H | H | H | H | H |
| H-60 | D[2] | H | H | OMe | H | H | H | H | H |
| H-61 | D[2] | CH3 | CH3 | H | H | H | H | H | H |

-continued

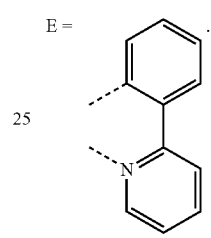

| Cpd. | L' | R45 | R44 | R43 | R42 | A24 | A23 | A22 | A21 |
|---|---|---|---|---|---|---|---|---|---|
| H-62 | D[2)] | CH₃ | H | CH₃ | H | H | H | H | H |
| H-63 | D[2)] | H | H | Ph | H | H | H/Ph[1)] | Ph/H[1)] | H |
| H-64 | D[2)] | H | t-Bu | H | H | H | H | H | H |
| H-65 | A | H | [3)] | H | H | H | H | H | H |
| H-66 | B | H | [3)] | H | H | H | H | H | H |
| H-67 | C | H | [3)] | H | H | H | H | H | H |
| H-68 | D | H | [3)] | H | H | H | H | H | H |
| H-69 | E[2)] | H | H | H | H | H | H | H | H |
| H-70 | E[2)] | F | H | H | H | H | H | H | H |
| H-71 | E[2)] | H | H | F | H | H | H | H | H |
| H-72 | E[2)] | F | H | F | H | H | H | H | H |
| H-73 | E[2)] | F | H | H | F | H | H | H | H |
| H-74 | E[2)] | H | H | CF₃ | H | H | H | H | H |
| H-75 | E[2)] | H | CF₃ | H | CF₃ | H | H | H | H |
| H-76 | E[2)] | CF₃ | H | H | H | H | H | H | H |
| H-77 | E[2)] | H | CH₃ | H | CH₃ | H | H | H | H |
| H-78 | E[2)] | H | H | CH₃ | H | H | H | H | H |
| H-79 | E[2)] | H | H | Ph | H | H | H | H | H |
| H-80 | E[2)] | H | H | OMe | H | H | H | H | H |
| H-81 | E[2)] | CH₃ | CH₃ | H | H | H | H | H | H |
| H-82 | E[2)] | CH₃ | H | CH₃ | H | H | H | H | H |
| H-83 | E[2)] | H | H | Ph | H | H | H/Ph[1)] | Ph/H[1)] | H |
| H-84 | E[2)] | H | t-Bu | H | H | H | H | H | H |
| H-85 | E[2)] | H | [3)] | H | H | H | H | H | H |

[1)] mixture of isomers.

[2)] A = 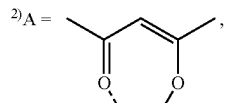,

B = 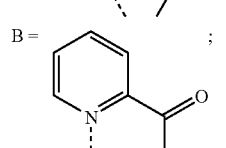;

C = 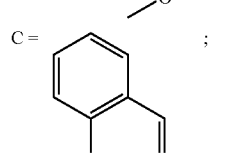;

D = 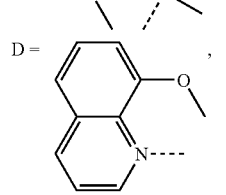,

E = 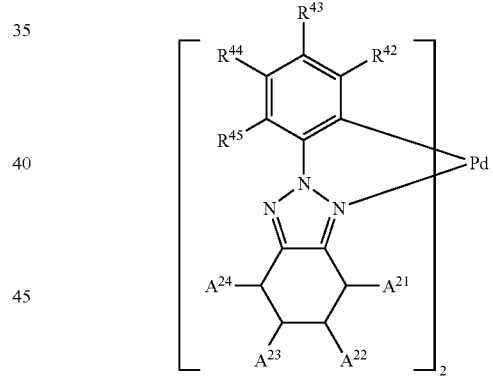.

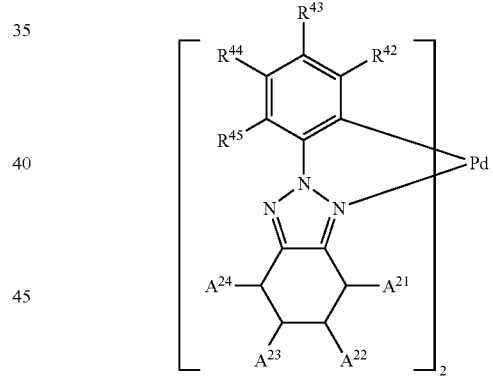

| Cpd. | R45 | R44 | R43 | R42 | A24 | A23 | A22 | A21 |
|---|---|---|---|---|---|---|---|---|
| M-1 | H | H | H | H | H | H | H | H |
| M-2 | F | H | H | H | H | H | H | H |
| M-3 | H | H | F | H | H | H | H | H |
| M-4 | F | H | F | H | H | H | H | H |
| M-5 | F | H | H | F | H | H | H | H |
| M-6 | H | H | CF₃ | H | H | H | H | H |
| M-7 | H | CF₃ | H | CF₃ | H | H | H | H |
| M-8 | CF₃ | H | H | H | H | H | H | H |
| M-9 | H | CH₃ | H | CH₃ | H | H | H | H |
| M-10 | H | H | CH₃ | H | H | H | H | H |
| M-11 | H | H | Ph | H | H | H | H | H |
| M-12 | H | H | OMe | H | H | H | H | H |
| M-13 | CH₃ | CH₃ | H | H | H | H | H | H |
| M-14 | CH₃ | H | CH₃ | H | H | H | H | H |
| M-15 | H | H | Ph | H | H | H/Ph[1)] | Ph/H[1)] | H |
| M-16 | H | H | t-Bu | H | H | H | H | H |

[1)] mixture of isomers.

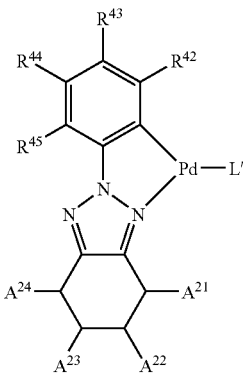

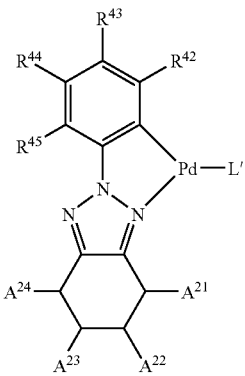

| Cpd. | L' | R45 | R44 | R43 | R42 | A24 | A23 | A22 | A21 |
|---|---|---|---|---|---|---|---|---|---|
| N-1 | A[2)] | H | H | H | H | H | H | H | H |
| N-2 | A[2)] | F | H | H | H | H | H | H | H |
| N-3 | A[2)] | H | H | F | H | H | H | H | H |
| N-4 | A[2)] | F | H | F | H | H | H | H | H |
| N-5 | A[2)] | F | H | H | F | H | H | H | H |
| N-6 | A[2)] | H | H | CF3 | H | H | H | H | H |
| N-7 | A[2)] | H | CF3 | H | CF3 | H | H | H | H |
| N-8 | A[2)] | CF3 | H | H | H | H | H | H | H |
| N-9 | A[2)] | H | CH3 | H | CH3 | H | H | H | H |
| N-10 | A[2)] | H | H | CH3 | H | H | H | H | H |
| N-11 | A[2)] | H | H | Ph | H | H | H | H | H |
| N-12 | A[2)] | H | H | OMe | H | H | H | H | H |
| N-13 | A[2)] | CH3 | CH3 | H | H | H | H | H | H |
| N-14 | A[2)] | CH3 | H | CH3 | H | H | H | H | H |
| N-15 | A[2)] | H | H | Ph | H | H | H/Ph[1)] | Ph/H[1)] | H |
| N-16 | A[2)] | H | t-Bu | H | H | H | H | H | H |
| N-17 | B[2)] | H | H | H | H | H | H | H | H |
| N-18 | B[2)] | F | F | H | H | H | H | H | H |
| N-19 | B[2)] | H | H | H | F | H | H | H | H |
| N-20 | B[2)] | F | H | F | H | H | H | H | H |
| N-21 | B[2)] | F | F | H | F | H | H | H | H |
| N-22 | B[2)] | H | H | CF3 | H | H | H | H | H |
| N-23 | B[2)] | H | CF3 | H | CF3 | H | H | H | H |
| N-24 | B[2)] | CF3 | CF3 | H | H | H | H | H | H |
| N-25 | B[2)] | H | CH3 | H | CH3 | H | H | H | H |
| N-26 | B[2)] | H | H | CH3 | H | H | H | H | H |
| N-27 | B[2)] | H | H | H | Ph | H | H | H | H |
| N-28 | B[2)] | H | H | H | OMe | H | H | H | H |
| N-29 | B[2)] | CH3 | CH3 | CH3 | H | H | H | H | H |
| N-30 | B[2)] | CH3 | CH3 | H | CH3 | H | H | H | H |
| N-31 | B[2)] | H | H | H | Ph | H | H | H/Ph[1)] | Ph/H[1)] |
| N-32 | B[2)] | H | H | t-Bu | H | H | H | H | H |
| N-33 | C[2)] | H | H | H | H | H | H | H | H |
| N-34 | C[2)] | F | H | H | H | H | H | H | H |
| N-35 | C[2)] | H | H | F | H | H | H | H | H |
| N-36 | C[2)] | F | F | H | H | H | H | H | H |
| N-37 | C[2)] | F | H | H | F | H | H | H | H |
| N-38 | C[2)] | H | H | CF3 | H | H | H | H | H |
| N-39 | C[2)] | H | CF3 | H | CF3 | H | H | H | H |
| N-40 | C[2)] | CF3 | H | H | H | H | H | H | H |
| N-41 | C[2)] | H | CH3 | H | CH3 | H | H | H | H |
| N-42 | C[2)] | H | H | CH3 | H | H | H | H | H |
| N-43 | C[2)] | H | H | Ph | H | H | H | H | H |
| N-44 | C[2)] | H | H | OMe | H | H | H | H | H |
| N-45 | C[2)] | CH3 | CH3 | H | H | H | H | H | H |
| N-46 | C[2)] | CH3 | H | CH3 | H | H | H | H | H |
| N-47 | C[2)] | H | H | Ph | H | H | H/Ph[1)] | Ph/H[1)] | H |
| N-48 | C[2)] | H | t-Bu | H | H | H | H | H | H |
| N-49 | D[2)] | H | H | H | H | H | H | H | H |
| N-50 | D[2)] | F | H | H | H | H | H | H | H |
| N-51 | D[2)] | H | H | F | H | H | H | H | H |
| N-52 | D[2)] | F | H | H | F | H | H | H | H |
| N-53 | D[2)] | F | H | F | H | H | H | H | H |
| N-54 | D[2)] | H | H | CF3 | H | H | H | H | H |
| N-55 | D[2)] | H | CF3 | H | CF3 | H | H | H | H |
| N-56 | D[2)] | CF3 | H | H | H | H | H | H | H |
| N-57 | D[2)] | H | CH3 | H | CH3 | H | H | H | H |
| N-58 | D[2)] | H | H | CH3 | H | H | H | H | H |
| N-59 | D[2)] | H | H | Ph | H | H | H | H | H |
| N-60 | D[2)] | H | H | OMe | H | H | H | H | H |
| N-61 | D[2)] | CH3 | CH3 | H | H | H | H | H | H |
| N-62 | D[2)] | CH3 | H | CH3 | H | H | H | H | H |
| N-63 | D[2)] | H | H | Ph | H | H | H/Ph[1)] | Ph/H[1)] | H |
| N-64 | D[2)] | H | t-Bu | H | H | H | H | H | H |
| N-65 | A | H | [3)] | H | H | H | H | H | H |
| N-66 | B | H | [3)] | H | H | H | H | H | H |
| N-67 | C | H | [3)] | H | H | H | H | H | H |
| N-68 | D | H | [3)] | H | H | H | H | H | H |
| N-69 | E[2)] | H | H | H | H | H | H | H | H |
| N-70 | E[2)] | F | H | H | H | H | H | H | H |
| N-71 | E[2)] | H | H | F | H | H | H | H | H |
| N-72 | E[2)] | F | F | H | H | H | H | H | H |
| N-73 | E[2)] | F | H | H | F | H | H | H | H |
| N-74 | E[2)] | H | H | CF3 | H | H | H | H | H |
| N-75 | E[2)] | H | CF3 | H | CF3 | H | H | H | H |
| N-76 | E[2)] | CF3 | H | H | H | H | H | H | H |
| N-77 | E[2)] | H | CH3 | H | CH3 | H | H | H | H |
| N-78 | E[2)] | H | H | CH3 | H | H | H | H | H |
| N-79 | E[2)] | H | H | Ph | H | H | H | H | H |
| N-80 | E[2)] | H | H | OMe | H | H | H | H | H |
| N-81 | E[2)] | CH3 | CH3 | H | H | H | H | H | H |
| N-82 | E[2)] | CH3 | H | CH3 | H | H | H | H | H |
| N-83 | E[2)] | H | H | Ph | H | H | H/Ph[1)] | Ph/H[1)] | H |
| N-84 | E[2)] | H | t-Bu | H | H | H | H | H | H |
| N-85 | E[2)] | H | [3)] | H | H | H | H | H | H |

[1)] mixture of isomers.

[2)] A = 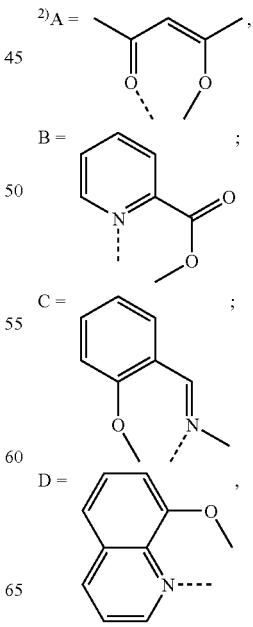, B = , C = , D = ,

-continued

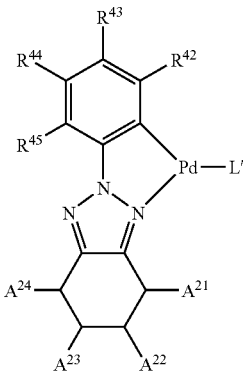

| Cpd. | L' | R45 | R44 | R43 | R42 | A24 | A23 | A22 | A21 |
|------|-----|-----|-----|-----|-----|-----|-----|-----|-----|

E =

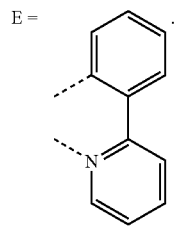

3) 2,4,4-trimethylpent-2-yl.

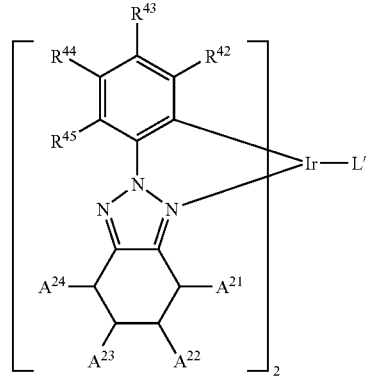

| Cpd. | L' | R45 | R44 | R43 | R42 | A24 | A23 | A22 | A21 |
|------|-----|-----|-----|-----|-----|-----|-----|-----|-----|
| S-1 | A2) | H | H | H | H | H | H | H | H |
| S-2 | A2) | F | H | H | H | H | H | H | H |
| S-3 | A2) | H | H | F | H | H | H | H | H |
| S-4 | A2) | F | H | F | H | H | H | H | H |
| S-5 | A2) | F | H | H | F | H | H | H | H |
| S-6 | A2) | H | H | CF3 | H | H | H | H | H |
| S-7 | A2) | H | CF3 | H | CF3 | H | H | H | H |
| S-8 | A2) | CF3 | H | H | H | H | H | H | H |
| S-9 | A2) | H | CH3 | H | CH3 | H | H | H | H |
| S-10 | A2) | H | H | CH3 | H | H | H | H | H |
| S-11 | A2) | H | H | Ph | H | H | H | H | H |
| S-12 | A2) | H | H | OMe | H | H | H | H | H |
| S-13 | A2) | CH3 | CH3 | H | H | H | H | H | H |
| S-14 | A2) | CH3 | H | CH3 | H | H | H | H | H |
| S-15 | A2) | H | H | Ph | H | H | H/Ph1) | Ph/H1) | H |
| S-16 | A2) | H | t-Bu | H | H | H | H | H | H |
| S-17 | B2) | H | H | H | H | H | H | H | H |
| S-18 | B2) | F | F | H | H | H | H | H | H |
| S-19 | B2) | H | H | F | H | H | H | H | H |
| S-20 | B2) | F | F | F | F | H | H | H | H |
| S-21 | B2) | F | F | H | F | H | H | H | H |
| S-22 | B2) | H | H | H | CF3 | H | H | H | H |

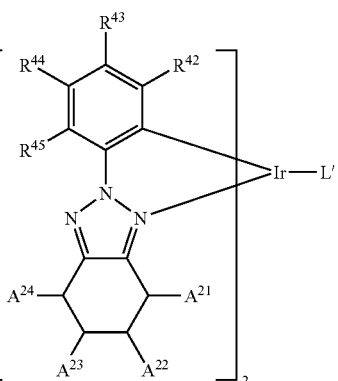

| Cpd. | L' | R45 | R44 | R43 | R42 | A24 | A23 | A22 | A21 |
|------|-----|-----|-----|-----|-----|-----|-----|-----|-----|
| S-23 | B2) | H | H | CF3 | H | CF3 | H | H | H |
| S-24 | B2) | CF3 | CF3 | H | H | H | H | H | H |
| S-25 | B2) | H | H | CH3 | H | CH3 | H | H | H |
| S-26 | B2) | H | H | H | CH3 | H | H | H | H |
| S-27 | B2) | H | H | H | Ph | H | H | H | H |
| S-28 | B2) | H | H | H | OMe | H | H | H | H |
| S-29 | B2) | CH3 | CH3 | CH3 | H | H | H | H | H |
| S-30 | B2) | CH3 | CH3 | H | CH3 | H | H | H | H |
| S-31 | B2) | H | H | H | Ph | H | H | H/Ph1) | Ph/H1) |
| S-32 | B2) | H | H | t-Bu | H | H | H | H | H |
| S-33 | C2) | H | H | H | H | H | H | H | H |
| S-34 | C2) | F | H | H | H | H | H | H | H |
| S-35 | C2) | H | H | F | H | H | H | H | H |
| S-36 | C2) | F | H | F | H | H | H | H | H |
| S-37 | C2) | F | H | H | F | H | H | H | H |
| S-38 | C2) | H | H | CF3 | H | H | H | H | H |
| S-39 | C2) | H | CF3 | H | CF3 | H | H | H | H |
| S-40 | C2) | CF3 | H | H | H | H | H | H | H |
| S-41 | C2) | H | CH3 | H | CH3 | H | H | H | H |
| S-42 | C2) | H | H | CH3 | H | H | H | H | H |
| S-43 | C2) | H | H | Ph | H | H | H | H | H |
| S-44 | C2) | H | H | OMe | H | H | H | H | H |
| S-45 | C2) | CH3 | CH3 | H | H | H | H | H | H |
| S-46 | C2) | CH3 | H | CH3 | H | H | H | H | H |
| S-47 | C2) | H | H | Ph | H | H | H/Ph1) | Ph/H1) | H |
| S-48 | C2) | H | t-Bu | H | H | H | H | H | H |
| S-49 | D2) | H | H | H | H | H | H | H | H |
| S-50 | D2) | F | H | H | H | H | H | H | H |
| S-51 | D2) | H | H | F | H | H | H | H | H |
| S-52 | D2) | F | H | F | H | H | H | H | H |
| S-53 | D2) | F | H | H | F | H | H | H | H |
| S-54 | D2) | H | H | CF3 | H | H | H | H | H |
| S-55 | D2) | H | CF3 | H | CF3 | H | H | H | H |
| S-56 | D2) | CF3 | H | H | H | H | H | H | H |
| S-57 | D2) | H | CH3 | H | CH3 | H | H | H | H |
| S-58 | D2) | H | H | CH3 | H | H | H | H | H |
| S-59 | D2) | H | H | Ph | H | H | H | H | H |
| S-60 | D2) | H | H | OMe | H | H | H | H | H |
| S-61 | D2) | CH3 | CH3 | H | H | H | H | H | H |
| S-62 | D2) | CH3 | H | CH3 | H | H | H | H | H |
| S-63 | D2) | H | H | Ph | H | H | H/Ph1) | Ph/H1) | H |
| S-64 | D2) | H | t-Bu | H | H | H | H | H | H |
| S-65 | A | H | 3) | H | H | H | H | H | H |
| S-66 | B | H | 3) | H | H | H | H | H | H |
| S-67 | C | H | 3) | H | H | H | H | H | H |
| S-68 | D | H | 3) | H | H | H | H | H | H |

-continued

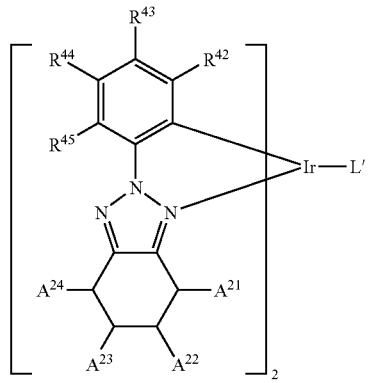

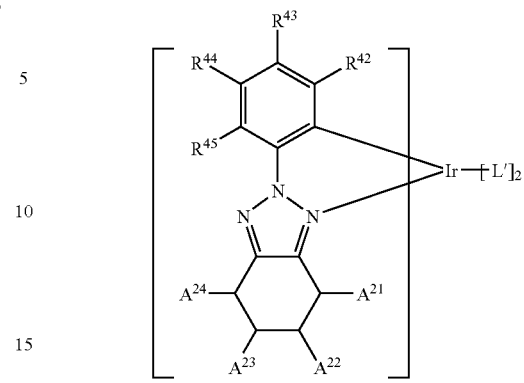

| Cpd. | L' | R45 | R44 | R43 | R42 | A24 | A23 | A22 | A21 |
|---|---|---|---|---|---|---|---|---|---|

[1] mixture of isomers.

[2] A =

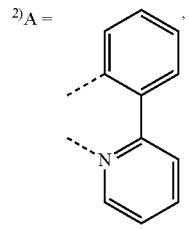

B = 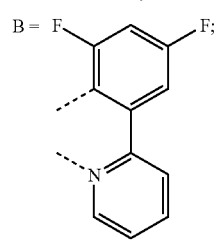 ;

C = 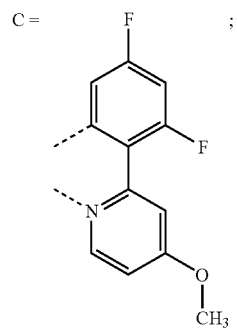 ;

D = 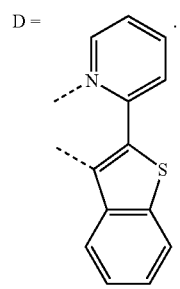 .

[3] 2,4,4-trimethylpent-2-yl.

| Cpd. | L' | R45 | R44 | R43 | R42 | A24 | A23 | A22 | A21 |
|---|---|---|---|---|---|---|---|---|---|
| T-1 | A[2] | H | H | H | H | H | H | H | H |
| T-2 | A[2] | F | H | H | H | H | H | H | H |
| T-3 | A[2] | H | H | F | H | H | H | H | H |
| T-4 | A[2] | F | H | F | H | H | H | H | H |
| T-5 | A[2] | F | H | H | F | H | H | H | H |
| T-6 | A[2] | H | H | CF3 | H | H | H | H | H |
| T-7 | A[2] | H | CF3 | H | CF3 | H | H | H | H |
| T-8 | A[2] | CF3 | H | H | H | H | H | H | H |
| T-9 | A[2] | H | CH3 | H | CH3 | H | H | H | H |
| T-10 | A[2] | H | H | CH3 | H | H | H | H | H |
| T-11 | A[2] | H | H | Ph | H | H | H | H | H |
| T-12 | A[2] | H | H | OMe | H | H | H | H | H |
| T-13 | A[2] | CH3 | CH3 | H | H | H | H | H | H |
| T-14 | A[2] | CH3 | H | CH3 | H | H | H | H | H |
| T-15 | A[2] | H | H | Ph | H | H | H/Ph[1] | Ph/H[1] | H |
| T-16 | A[2] | H | t-Bu | H | H | H | H | H | H |
| T-17 | B[2] | H | H | H | H | H | H | H | H |
| T-18 | B[2] | F | F | H | H | H | H | H | H |
| T-19 | B[2] | H | H | H | F | H | H | H | H |
| T-20 | B[2] | F | F | F | F | H | H | H | H |
| T-21 | B[2] | F | F | H | H | F | H | H | H |
| T-22 | B[2] | H | H | H | CF3 | H | H | H | H |
| T-23 | B[2] | H | H | CF3 | H | CF3 | H | H | H |
| T-24 | B[2] | CF3 | CF3 | H | H | H | H | H | H |
| T-25 | B[2] | H | H | CH3 | H | CH3 | H | H | H |
| T-26 | B[2] | H | H | H | CH3 | H | H | H | H |
| T-27 | B[2] | H | H | Ph | H | H | H | H | H |
| T-28 | B[2] | H | H | H | OMe | H | H | H | H |
| T-29 | B[2] | CH3 | CH3 | CH3 | H | H | H | H | H |
| T-30 | B[2] | CH3 | CH3 | H | CH3 | H | H | H | H |
| T-31 | B[2] | H | H | H | Ph | H | H | H/Ph[1] | Ph/H[1] |
| T-32 | B[2] | H | H | t-Bu | H | H | H | H | H |
| T-33 | C[2] | H | H | H | H | H | H | H | H |
| T-34 | C[2] | F | H | H | H | H | H | H | H |
| T-35 | C[2] | H | H | F | H | H | H | H | H |
| T-36 | C[2] | F | H | F | H | H | H | H | H |
| T-37 | C[2] | F | H | H | F | H | H | H | H |
| T-38 | C[2] | H | H | CF3 | H | H | H | H | H |
| T-39 | C[2] | H | CF3 | H | CF3 | H | H | H | H |
| T-40 | C[2] | CF3 | H | H | H | H | H | H | H |
| T-41 | C[2] | H | CH3 | H | CH3 | H | H | H | H |
| T-42 | C[2] | H | H | CH3 | H | H | H | H | H |
| T-43 | C[2] | H | H | Ph | H | H | H | H | H |
| T-44 | C[2] | H | H | OMe | H | H | H | H | H |
| T-45 | C[2] | CH3 | CH3 | H | H | H | H | H | H |
| T-46 | C[2] | CH3 | H | CH3 | H | H | H | H | H |
| T-47 | C[2] | H | H | Ph | H | H | H/Ph[1] | Ph/H[1] | H |
| T-48 | C[2] | H | t-Bu | H | H | H | H | H | H |
| T-49 | D[2] | H | H | H | H | H | H | H | H |
| T-50 | D[2] | F | H | H | H | H | H | H | H |
| T-51 | D[2] | H | H | F | H | H | H | H | H |
| T-52 | D[2] | F | H | F | H | H | H | H | H |
| T-53 | D[2] | F | H | H | F | H | H | H | H |
| T-54 | D[2] | H | H | CF3 | H | H | H | H | H |
| T-55 | D[2] | H | CF3 | H | CF3 | H | H | H | H |
| T-56 | D[2] | CF3 | H | H | H | H | H | H | H |
| T-57 | D[2] | H | CH3 | H | CH3 | H | H | H | H |

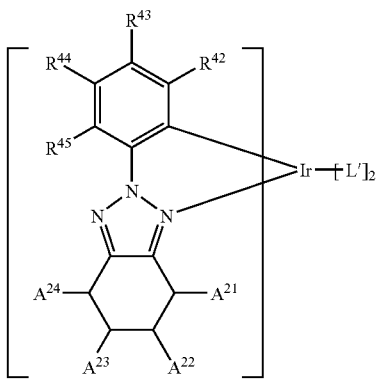

| Cpd. | L' | $R^{45}$ | $R^{44}$ | $R^{43}$ | $R^{42}$ | $A^{24}$ | $A^{23}$ | $A^{22}$ | $A^{21}$ |
|---|---|---|---|---|---|---|---|---|---|
| T-58 | D[2] | H | H | $CH_3$ | H | H | H | H | H |
| T-59 | D[2] | H | H | Ph | H | H | H | H | H |
| T-60 | D[2] | H | H | OMe | H | H | H | H | H |
| T-61 | D[2] | $CH_3$ | $CH_3$ | H | H | H | H | H | H |
| T-62 | D[2] | $CH_3$ | H | $CH_3$ | H | H | H | H | H |
| T-63 | D[2] | H | H | Ph | H | H | H/Ph[1] | Ph/H[1] | H |
| T-64 | D[2] | H | t-Bu | H | H | H | H | H | H |
| T-65 | A | H | [3] | H | H | H | H | H | H |
| T-66 | B | H | [3] | H | H | H | H | H | H |
| T-67 | C | H | [3] | H | H | H | H | H | H |
| T-68 | D | H | [3] | H | H | H | H | H | H |

[1] mixture of isomers.

[2] A = 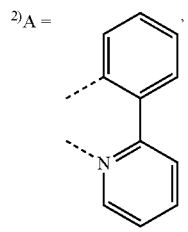,

B = 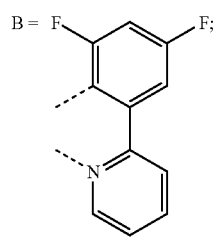

C = 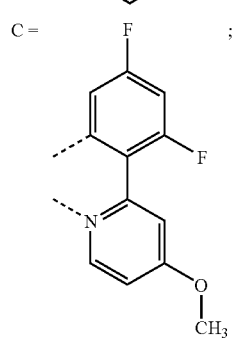

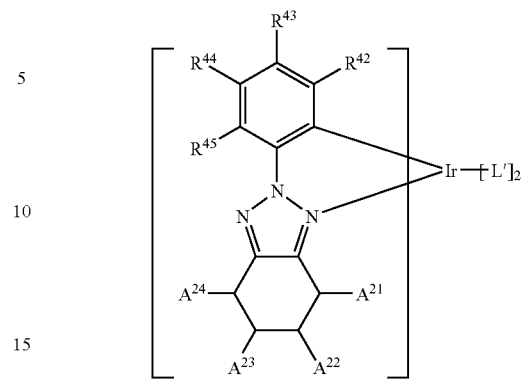

| Cpd. | L' | $R^{45}$ | $R^{44}$ | $R^{43}$ | $R^{42}$ | $A^{24}$ | $A^{23}$ | $A^{22}$ | $A^{21}$ |
|---|---|---|---|---|---|---|---|---|---|

D = 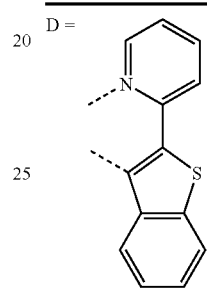.

The metal complexes of the present invention can be prepared according to usual methods known in the prior art. A convenient one-step method for preparing iridium metal complexes of formula $Ir(L^a)_3$ comprises reacting commercially available iridium trichloride hydrate with an excess of $L^aH$ in the presence of 3 equivalents silver trifluoroacetate and optionally in the presence of a solvent (such as halogen based solvents, alcohol based solvents, ether based solvents, ester based solvents, ketone based solvents, nitrile based solvents, and water). The tris-cyclometalated iridium complexes are isolated and purified by conventional methods. In some cases mixtures of isomers are obtained. Often the mixture can be used without isolating the individual isomers.

The iridium metal complexes of formula $Ir(La)_2L'$ can, for example be prepared by first preparing an intermediate iridium dimer of formula

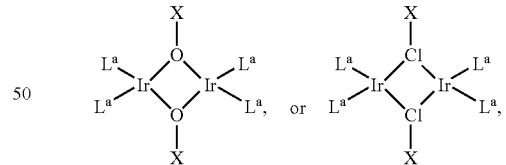

wherein X is H or lower alkyl such as methyl or ethyl, and $L^a$ is as defined above, and then addition of HL'. The iridium dimers can generally be prepared by first reacting iridium trichloride hydrate with $HL^a$ and adding NaX and by reacting iridium trichloride hydrate with $HL^a$ in a suitable solvent, such as 2-ethoxyethanol.

Of specific technical importance is thus a complex containing 2 triazole ligands of the invention bonding to the same Ir central atom (e.g. a complex of the above formula I wherein n1 is 2; triazole ligands being, for example, of one of the above formulae IIIa-IIIc), and, as a further bidentate ligand, 2 halogen atoms or alcoholate residues coordinated to a further central atom, thus forming a dimeric complex e.g. of the formula

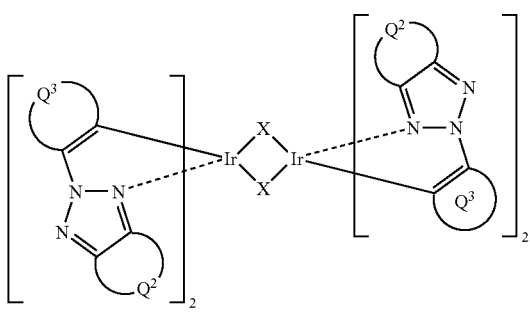

wherein X stands for halogen such as Cl or OR# such as OH, OCH$_3$, OC$_2$H$_5$ etc., and all other symbols are as defined above.

Halogen (or halo) is fluorine, chlorine, bromine and iodine.

C$_1$-C$_{24}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

C$_1$-C$_{24}$ perfluoroalkyl is a branched or unbranched radical such as for example —CF$_3$, —CF$_2$CF$_3$, —CF$_2$CF$_2$CF$_3$, —CF(CF$_3$)$_2$, —(CF$_2$)$_3$CF$_3$, and —C(CF$_3$)$_3$.

C$_1$-C$_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

C$_2$-C$_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

C$_{2-24}$alkynyl is straight-chain or branched and preferably C$_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

C$_4$-C$_{18}$cycloalkyl, especially C$_5$-C$_{12}$cycloalkyl, is preferably C$_5$-C$_{12}$cycloalkyl or said cycloalkyl substituted by one to three C$_1$-C$_4$alkyl groups, such as, for example, cyclopentyl, methyl-cyclopentyl, dimethylcyclopentyl, cyclohexyl, methylcyclohexyl, dimethylcyclohexyl, trimethyl-cyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred.

Examples of C$_4$-C$_{18}$cycloalkyl, which is interrupted by S, O, or NR$^{25}$, are piperidyl, piperazinyl and morpholinyl.

C$_2$-C$_{24}$alkenyl is for example vinyl, allyl, butenyl, pentenyl, hexenyl, heptenyl, or octenyl.

Aryl is usually C$_6$-C$_{30}$aryl, preferably C$_6$-C$_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three C$_1$-C$_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

C$_7$-C$_{24}$aralkyl radicals are preferably C$_7$-C$_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyl-dodecyl; or phenyl-C$_1$-C$_4$alkyl substituted on the phenyl ring by one to three C$_1$-C$_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl, or 3-methyl-5-(1',1',3',3'-tetramethyl-butyl)-benzyl.

Heteroaryl is typically C$_2$-C$_{26}$heteroaryl, i.e. a ring with five to seven ring atoms or a condensed rig system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

C$_6$-C$_{18}$cycloalkoxy is, for example, cyclopentyloxy, cyclohexyloxy, cycloheptyloxy or cyclooctyloxy, or said cycloalkoxy substituted by one to three C$_1$-C$_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

C$_6$-C$_{24}$aryloxy is typically phenoxy or phenoxy substituted by one to three C$_1$-C$_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

C$_6$-C$_{24}$aralkoxy is typically phenyl-C$_1$-C$_9$alkoxy, such as, for example, benzyloxy, α-methylbenzyloxy, α,α-dimethylbenzyloxy or 2-phenylethoxy.

C$_1$-C$_{24}$alkylthio radicals are straight-chain or branched alkylthio radicals, such as e.g. methylthio, ethylthio, propylthio, isopropylthio, n-butylthio, isobutylthio, pentylthio, isopentyl-thio, hexylthio, heptylthio, octylthio, decylthio, tetradecylthio, hexadecylthio or octadecylthio. C$_1$-C$_{24}$alkylselenium and C$_1$-C$_{24}$alkyltellurium are C$_1$-C$_{24}$alkylSe— and C$_1$-C$_{24}$alkylTe—, respectively.

Possible substituents of the above-mentioned groups include C$_1$-C$_8$alkyl, a hydroxyl group, a mercapto group, C$_1$-C$_8$alkoxy, C$_1$-C$_8$alkylthio, C$_5$-C$_{12}$cycloalkyl, C$_5$-C$_{12}$cycloalkoxy, C$_5$-C$_{12}$cycloalkylthio, halogen, halo-C$_1$-C$_8$alkyl, a cyano group, an aldehyde group, a ketone group, a carboxyl group, an ester group, a carbamoyl group, an amino group, a nitro group or a silyl group.

The term "haloalkyl" means groups given by partially or wholly substituting the above-mentioned alkyl group with halogen, such as trifluoromethyl etc. The "aldehyde group, ketone group, ester group, carbamoyl group and amino group" include those substituted by an C$_1$-C$_{24}$alkyl group, a C$_4$-C$_{18}$cycloalkyl group, an C$_6$-C$_{30}$aryl group, an C$_7$-C$_{24}$aralkyl group or a heterocyclic group, wherein the alkyl group, the cycloalkyl group, the aryl group, the aralkyl group and the heterocyclic group may be unsubstituted or substituted. The term "silyl group" means a group of formula —SiR$^{105}$R$^{106}$R$^{107}$, wherein R$^{105}$, R$^{106}$ and R$^{107}$ are independently of each other a $C_1$-$C_8$ alkyl group, in particular a $C_1$-$C_4$ alkyl group, a $C_6$-$C_{24}$ aryl group or a $C_7$-$C_{12}$ aralkyl group, such as a trimethylsilyl group.

If a substituent occurs more than one time in a group, it can be different in each occurrence.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex previously described.

In some embodiments, the active layer (c) may be substantially 100% of the metal complex because a host charge transporting material, such as $Alq_3$ is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material.

The device may include a support or substrate (not shown) adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e.g., ion beam sputtering), e-beam evaporation, and resistance evaporation.

Specific forms of physical vapor deposition include rf magnetron sputtering or inductively-coupled plasma physical vapor deposition ("ICP-PVD"). These deposition techniques are well-known within the semiconductor fabrication arts.

A hole-transport layer (b) may be adjacent the anode. Both hole transporting small molecule compounds and polymers can be used.

Commonly used hole transporting molecules, in addition to N,N'-diphenyl-N,N'-bis(3-methylphenyl)-[1,1'-biphenyl]-4,4'-diamine (TPD) and bis[4-(N,N-diethylamino)-2-methylphenyl] (4-methylphenyl)methane (MPMP), include: polyvinyl-carbazol, 1,1-bis[(di-4-tolylamino)phenyl] cyclohexane (TAPC); N,N'-bis(4-methylphenyl)-N,N'-bis(4-ethylphenyl)-[1,1'-(3,3'-dimethyl)biphenyl]-4,4'-diamine (ETPD); tetrakis-(3-methylphenyl)-N,N,N',N'-2,5-phenylenediamine (PDA); a-phenyl-4-N,N-diphenylaminostyrene (TPS); p-(diethylamino)benzaldehyde diphenylhydrazone (DEH); triphenylamine (TPA); 1-phenyl-3-[p-(diethylamino)styryl]-5-[p-(diethylamino)phenyl] pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); and porphyrinic compounds, such as copper phthalocyanine.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, and printing. The active organic materials can be applied directly by vapor deposition processes, depending upon the nature of the materials.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metal-cheated oxinoid compounds (e.g., $Alq_3$ or the like); phenanthroline-based compounds (e.g., 2,9-dimethyl-4,7-diphenyl-1,10-phenanthroline ("DDPA"), 4,7-diphenyl-1,10-phenanthroline ("DPA"), or the like; azole compounds (e.g., 2-(4-biphenylyl)-5-(4-t-butylphenyl)-1,3,4-oxadiazole ("PBD") or the like, 3-(4-biphenylyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e.g., Li, Na, K, Rb, Cs), the Group 2 (alkaline earth) metals, the Group 12 metals, the rare earths, the lanthanides (e.g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer (s) may be present within organic electronic devices. For example, a layer (not shown) between the hole injecting layer (b) and the active layer (c) may facilitate positive charge transport, band-gap matching of the layers, function as a protective layer, or the like. Similarly, additional layers (not shown) between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group 1 metal and a layer of aluminum. The Group 1 metal may lie closer to the active layer (c), and the aluminum may help to protect the Group 1 metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer (d), the electron-hole recombination zone can lie within the $Alq_3$ layer.

The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material (s) that for their particular applications.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source (s) may be electrically connected to the electronic device as part of a circuit.

In other embodiments, the phosphorus-containing metal complex compound can be used as a charge transport material in layer (b) or (d).

The compound does not need to be in a solid matrix diluent (e.g., host charge transport material) when used in layer (b)

(c), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e.g., oxygen-sensitive indicators, phosphorescent indicators in bioassays, or the like).

The following examples illustrate certain features and advantages of the present invention. They are intended to be illustrative of the invention, but not limiting. Unless otherwise indicated, all percentages are by weight, "over night" stands for a time period of 14 to 16 hours, and room temperature denotes a temperature from the range 20-25° C.

EXAMPLES

Example 1

Intermediate

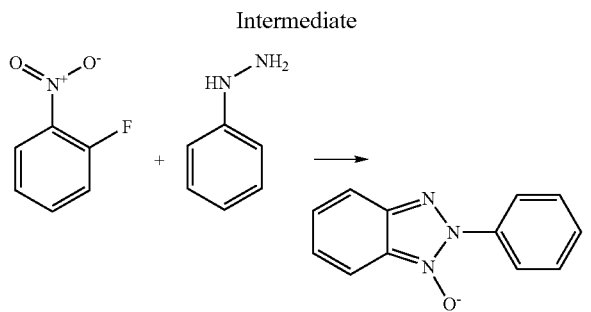

Procedure: Under a nitrogen stream, 35 g (0.426 mole) sodium acetate are added at room temperature to a solution of 30.7 g (0.284 mole) phenylhydrazine in 200 ml ethanol. 15 ml (0.142 mole) 1-fluoro-2-nitrobenzene are added at room temperature. The reaction mixture is heated to reflux and kept at this temperature for two hours, diluted with additional 60 ml ethanol, stirred over night at reflux and evaporated. To the residue 200 ml TBME and 150 ml water are added, the organic phase is separated, washed with water twice, dried over sodium sulfate, filtered and evaporated. Yield: 37.0 g of orange oil Example 2

Reduction to Obtain the Benzotriazole Intermediate

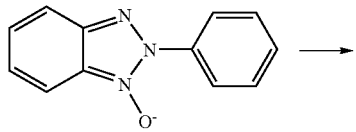

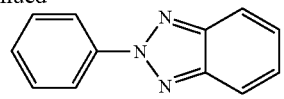

Procedure: 80 g (2 mole) sodium hydroxide are added in five portions to a solution of 37 g (0.142 mole) of the product of example 1 in 800 ml ethanol. The temperature is raised to reflux. The mixture is cooled to 60° C., 29 g (0.312 mol) sodium thiosulfate are added and the reaction mixture is heated to reflux, kept at this temperature over night and evaporated. To the residue 300 ml TBME and 300 ml water are added, the aqueous phase is separated and extracted with 150 ml TBME. The combined organic phases are washed with water twice, dried over sodium sulfate, filtered and evaporated. The solid residue is purified by column on silica gel (hexane/4% TBME). Yield: 10.2 g (37%) brown solid.

Example 3

Ligand 1

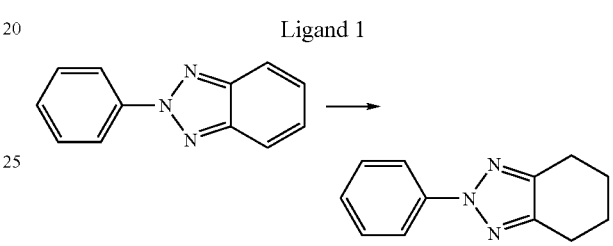

Procedure: 1.0 g (5 mmole) 2-phenyl-2-H-benzotriazole and 53 mg (0.025 mmole) Pd/5% on $Ba_2SO_4$ are added to 15 ml acetic acid and hydrogenated at 30° C./3 bar for 5 hours. The reaction mixture is filtered over celite. The filtrate is evaporated; the residue is stirred with 10 ml toluene and evaporated. Yield: 1.0 g (100%) off-white solid.

Example 4

Intermediate

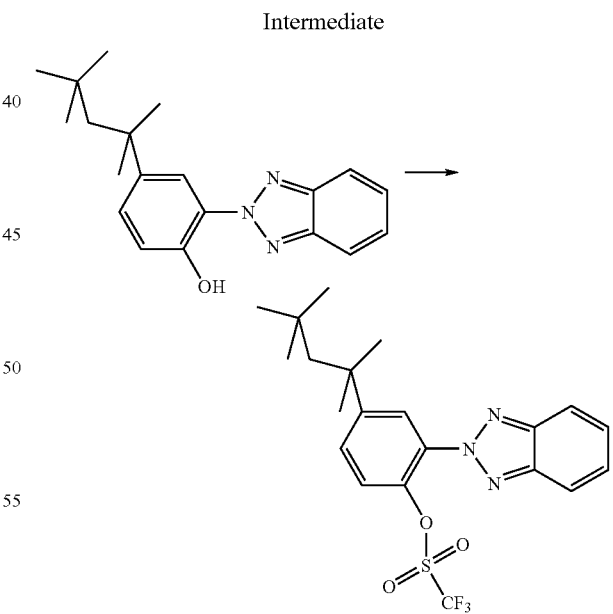

Procedure: Under a nitrogen stream 16.6 g (0.0513 mole) of 2-benzotriazol-2-yl-4-(1,1,3,3-tetramethyl-butyl)-phenol and 10 ml (0.29 mole) pyridine are added at room temperature to 500 ml dichloromethane. 10 ml (0.062 mole) trifluoromethansulfonic anhydride are added dropwise during 10 min at max. 30° C. The yellow solution is stirred at room temperature over night, washed with water twice, dried over sodium sulfate, filtered and evaporated. The oily residue is

Example 5

Intermediate

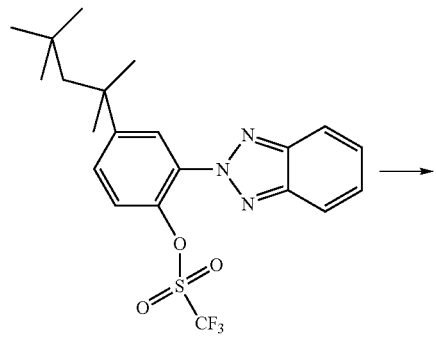

Procedure: Under a nitrogen stream 18 g (0.04 mole) trifluoro-methanesulfonic acid 2-benzotriazol-2-yl-4-(1,1,3,3-tetramethyl-butyl)-phenyl ester, 16.5 ml (0.12 mole) triethylamine, 3.0 ml (0.08 mole) formic acid, 0.18 g (0.0008 mole) palladium(II) acetate and 0.42 g (0.0016 mole) triphenyl phosphine are added to 80 ml dichloromethane at room temperature. The reaction mixture is stirred at 80° C. for 2.5 hours, cooled to room temperature. 200 ml TBME and 200 ml water are added, the aqueous phase is separated and extracted with 150 ml TBME. The combined organic phases are washed with water twice, dried over sodium sulfate, evaporated. The oily residue is purified by column on silica gel (hexane/10% ethyl acetate). Yield: 11 g (91%) of the product as a white solid.

Example 6

Ligand 2

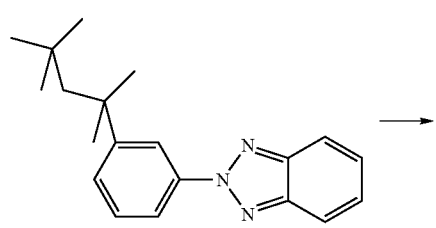

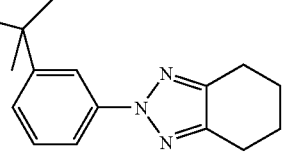

Procedure: 1.23 g (0.004 mole) of 2-[3-(1,1,3,3-tetramethyl-butyl)-phenyl]-2H-benzotriazole and 42 mg (0.02 mMole) Pd/5% on $Ba_2SO_4$ are added to 30 ml acetic acid and hydrogenated at 30° C./3 bar for 5 hours. The reaction mixture is filtered over celite and the filtrate is evaporated. The residue is stirred with 10 ml toluene and evaporated. Yield: 1.27 (100%) off-white solid.

Example 7

Intermediate

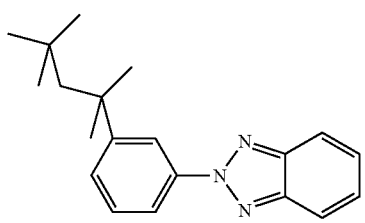 + 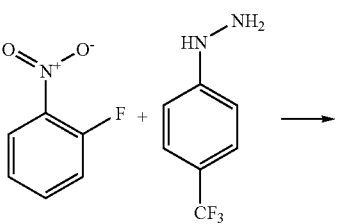 →

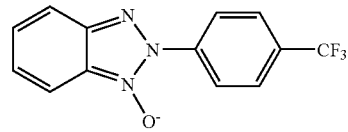

Procedure: Under a nitrogen stream 3.5 g (0.043 mole) sodium acetate are added at room temperature to a solution of 5 g (0.028 mole) 4-(trifluoromethyl)phenylhydrazine in 26 ml ethanol. 1.5 ml (0.014 mole) 1-fluoro-2-nitrobenzene are added at room temperature. The reaction mixture is heated to reflux and kept at this temperature for five days and evaporated. To the residue 100 ml ethyl acetate and 50 ml water are added. The aqueous phase is separated and extracted with 50 ml ethyl acetate. The combined organic phases are washed with water twice, dried over sodium sulfate, filtered and evaporated. The solid residue is purified by column on silica gel (hexane/25% TBME). Yield: 1.7 g (40%) orange solid

Example 8

Intermediate

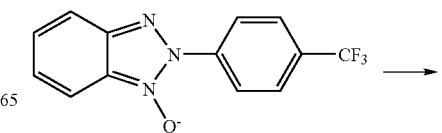 →

-continued

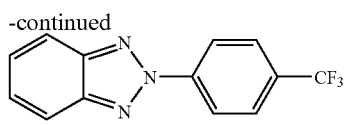

Procedure: 2.8 g (0.07 mole) sodium hydroxide are added to a solution of 1.7 g (0.0.005 mole) of the product of example 7 in 30 ml ethanol. 1.95 g (0.011 mol) sodium thiosulfate is added. The reaction mixture is heated to reflux, kept at this temperature for four hours and evaporated. To the residue 50 ml TBME and 30 ml water are added, the aqueous phase is separated and extracted with 15 ml TBME. The combined organic phases are washed with water twice, dried over sodium sulfate, filtered and evaporated. The solid residue is purified by column on silica gel (hexane/5% ethyl acetate). Yield: 1.2 (81%) of yellow solid.

Example 9

Ligand 3

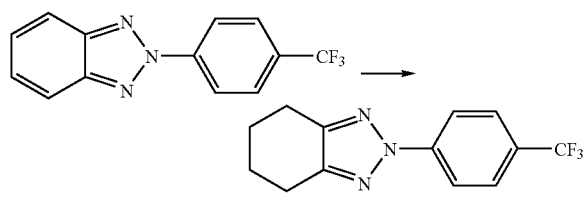

Procedure: 0.525 g (2.0 mmole) of 2-(4-trifluoromethyl-phenyl)-2H-benzotriazole and 21 mg (0.01 mmol) Pd/5% on $Ba_2SO_4$ are added to 10 ml acetic acid and hydrogenated at 30° C./3 bar for 9 hours. The reaction mixture is filtered over celite and the filtrate is evaporated. The residue is stirred with 10 ml toluene and evaporated. Yield: 0.48 g (90%) off-white solid.

Example 10

Intermediate

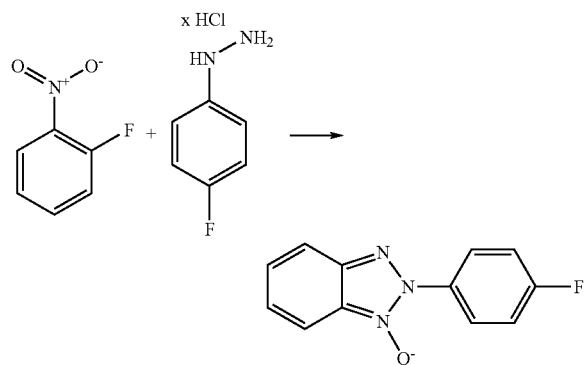

Procedure: Under a nitrogen stream 1.06 g (0.01 mol) sodium carbonate are added at room temperature to a suspension of 3.3 g (0.02 mole) 4-fluorophenylhydrazine hydrochloride in 20 ml ethanol. The mixture is heated to 50° C., 3.2 g (0.03 mol) sodium acetate and 1.04 ml (0.01 mol) 1-fluoro-2-nitrobenzene are added. The mixture is heated to reflux, stirred at this temperature for 18 hours and evaporated. To the residue 140 ml ethyl acetate and 100 ml water are added. The aqueous phase is separated and extracted with 140 ml ethyl acetate. The combined organic phases are washed with water twice, dried over sodium sulfate, filtered and evaporated. The solid residue is purified by column on silica gel (hexane/25% ethyl acetate). Yield: 1.3 (53%) off-white solid Example 11

Intermediate

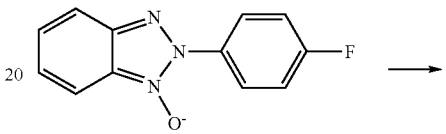

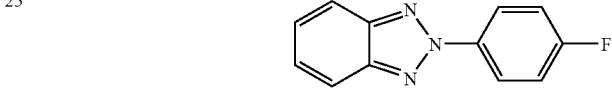

Procedure: 2.97 g (74 mmol) sodium hydroxide is added to a solution of 1.3 g (5.3 mmol) of the product of example 10 in 32 ml ethanol. 2.0 g (11.7 mmol) sodium thiosulfate is added. The reaction mixture is heated to reflux, kept at this temperature for four hours and evaporated. To the residue 50 ml TBME and 30 ml water are added, the aqueous phase is separated and extracted with 15 ml TBME. The combined organic phases are washed with water twice, dried over sodium sulfate, filtered and evaporated. The solid residue is purified by column on silica gel (hexane/5% ethyl acetate). Yield: 0.87 (77%) yellow solid.

Example 12

Ligand 4

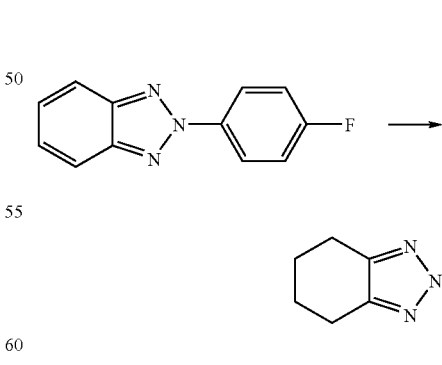

Procedure: 0.425 g (2 mmole) of 2-(4-fluoro-phenyl)-2H-benzotriazole and 20 mg (0.01 mmol) Pd/5% on $Ba_2SO_4$ are added to 10 ml acetic acid and hydrogenated at 30° C./3 bar for 5 hours. The reaction mixture is filtered over celite and the filtrate is evaporated. The residue is stirred with 10 ml toluene and evaporated. Yield: 0.43 g (99%) off-white solid.

Example 13

Complex 1

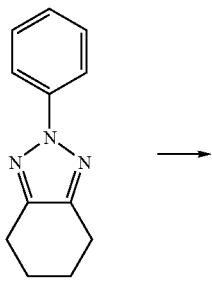

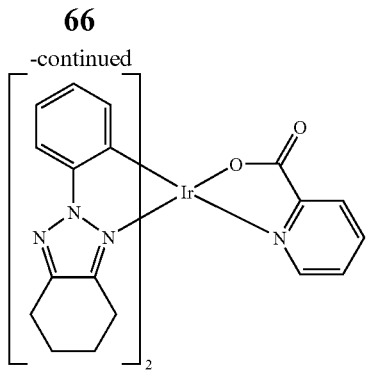

Procedure: 0.125 g (0.1 mmol) of the dimer obtained according to example 13 and 0.025 g (0.2 mmol) 2-picolinic acid are added to 8 ml 1,2-dichloroethane. The mixture is heated to reflux for 4 hours and then evaporated. The solid residue is purified by column chromatography on silica gel (ethyl acetate/5% methanol). Yield: 0.12 g (68%) yellow solid.

Example 15

Complex 3

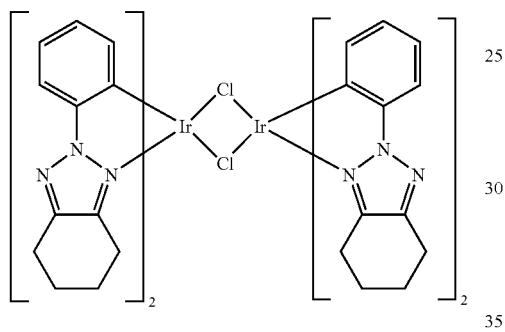

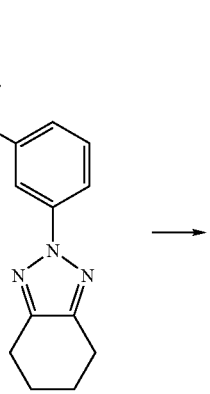

Procedure: 1 g (5 mmol) 2-phenyl-4,5,6,7-tetrahydro-2H-benzotriazole and 0.75 g (2.5 mmol) iridium trichloride hydrate are added to a mixture of 12 ml 2-ethoxyethanol and 4 ml water. The mixture is heated to reflux for 16 hours. After cooling to room temperature 12 ml water are added to the green suspension. The precipitate is filtered, washed with ethanol and hexane and dried at room temperature under reduced pressure. Yield: 1.16 (74%) greenish solid (mp.: 439° C.)

Example 14

Complex 2

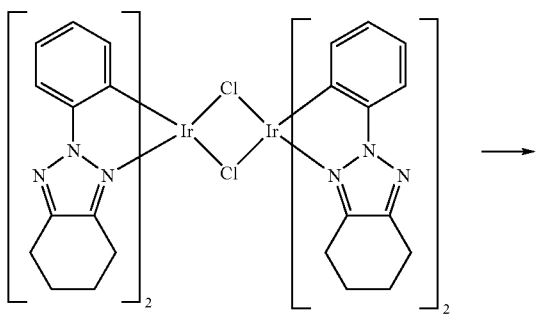

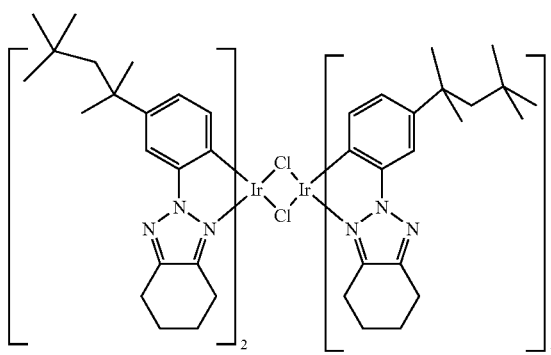

Procedure: 0.31 g (0.43 mmol) 2-[3-(1,1,3,3-tetramethyl-butyl)-phenyl]-4,5,6,7-tetrahydro-2H-benzotriazole and 0.15 g (0.5 mmol) iridium trichloride hydrate are added to a mixture of 12 ml 2-ethoxyethanol and 4 ml water. The mixture is heated to reflux for 16 hours. After cooling to room temperature 1 ml water is added to the yellow suspension. The precipitate is filtered, washed with ethanol and hexane and dried at room temperature under reduced pressure. Yield: 0.30 g (71%) yellow solid (mp.: 384° C.)

Example 16

Complex 4

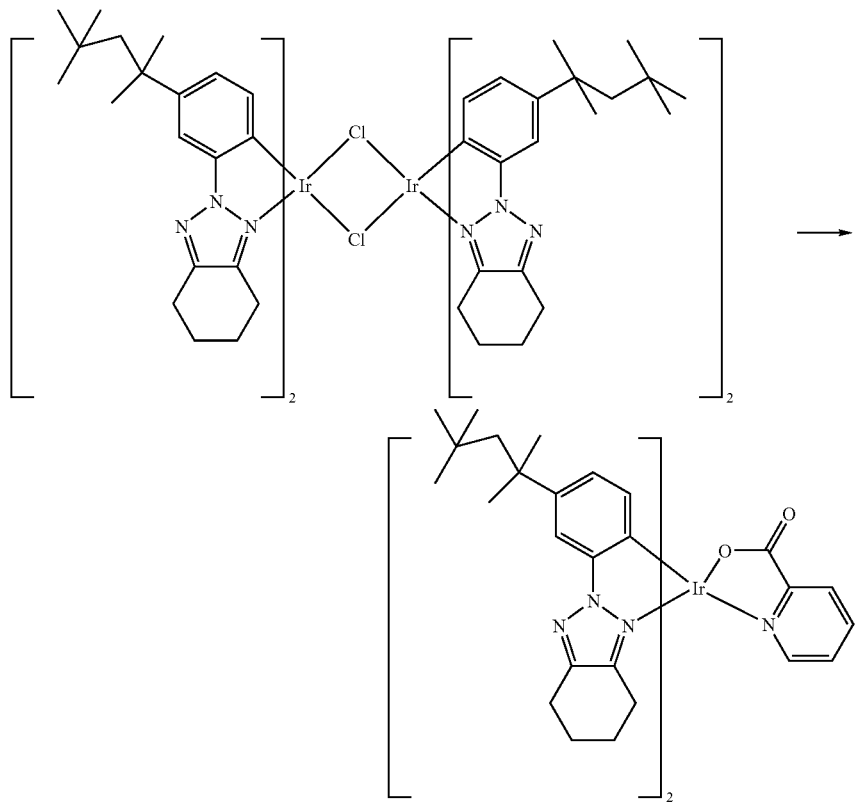

Procedure: 0.085 g (0.05 mmol) of the dimer obtained according to example 15 and 0.013 g (0.1 mmol) of 2-picolinic acid are added to 48 ml 1,2-dichloroethane. The mixture is heated to reflux for 3 hours and evaporated. The residue is purified by column on silica gel (ethyl acetate/5% methanol). Yield: 0.08 g (85%) greenish-yellow solid (mp.: 276° C.).

Following the procedures shown above, the following complexes are prepared:

Example 17

Complex 5

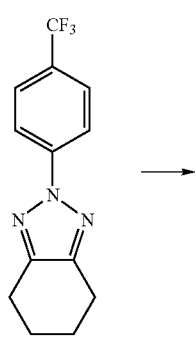

-continued

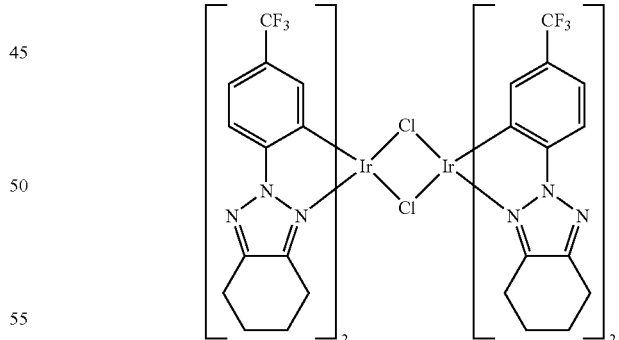

Procedure: 0.47 g (1.76 mmol) 2-(4-trifluoromethyl-phenyl)-4,5,6,7-tetrahydro-2H-benzotriazole and 0.263 g (0.88 mmole) iridium trichloride hydrate are added to a mixture of 4.2 ml 2-ethoxyethanol and 1.4 ml water. The mixture was heated to reflux for 16 hours. After cooling to room temperature 3 ml water is added to the greenish suspension. The precipitate was filtered, washed with ethanol and hexane and dried at room temperature under reduced pressure. Yield: 0.37 g (55%) greenish solid.

Example 18

Complex 6

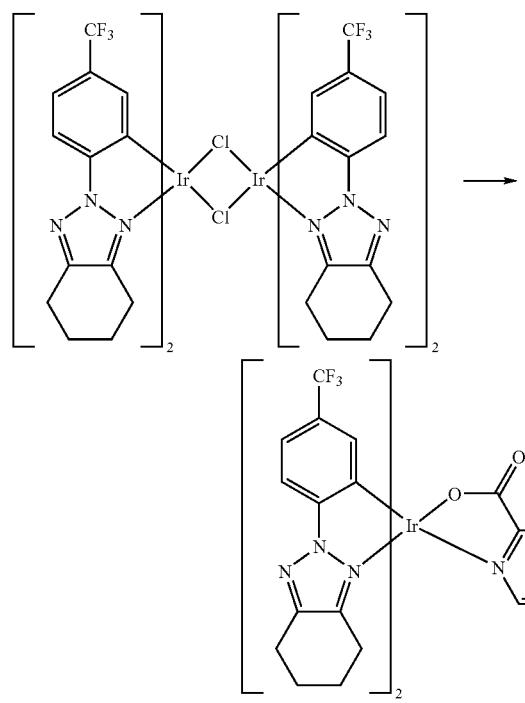

Procedure: 0.152 g (0.1 mmole) of the dimer obtained according to example 17 and 0.025 g (0.2 mmole) 2-picolinic acid are added to 8 ml 1,2-dichloroethane. The mixture is heated to reflux for 16 hours and evaporated. The solid residue is purified by column on silica gel (ethyl acetate/5% methanol). Yield: 0.12 g (70%) yellow solid (mp: 334° C.).

Example 19

Complex 7

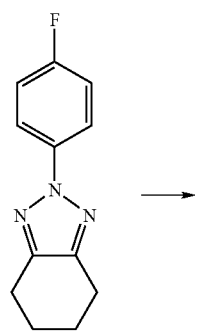

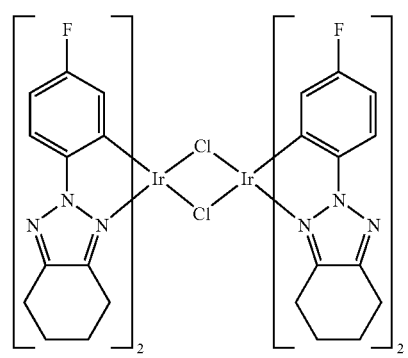

Procedure: 0.42 g (1.93 mmol) 2-(4-fluoro-phenyl)-4,5,6,7-tetrahydro-2H-benzotriazole and 0.29 (0.97 mmole) iridium trichloride hydrate are added to a mixture of 4.6 ml 2-ethoxyethanol and 1.2 ml water. The mixture is heated to reflux for 16 hours. After cooling to room temperature 4 ml water were added to the yellow suspension. The precipitate was filtered, washed with ethanol and hexane and dried at room temperature under reduced pressure. Yield: 0.512 (80%) yellow solid (mp: 433° C.).

Example 20

Complex 8

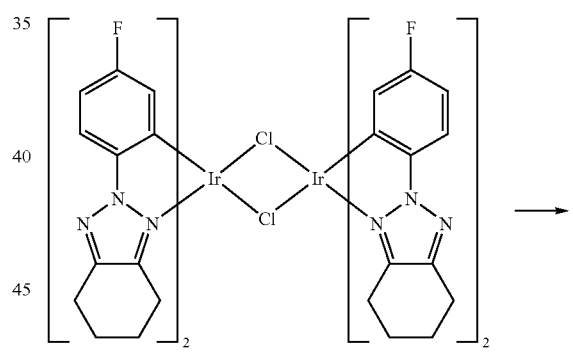

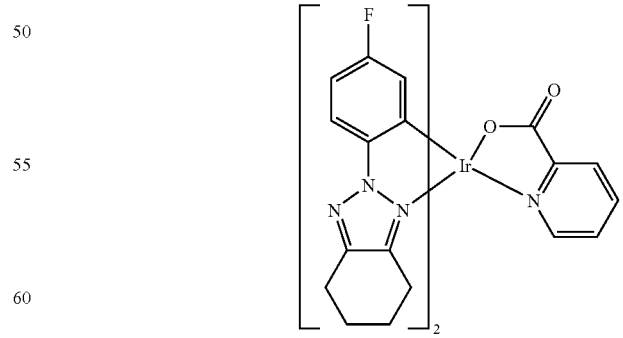

Procedure: 0.132 g (0.1 mmol) of the dimer obtained according to example 19 and 0.025 g (0.2 mmole) 2-picolinic acid are added to 8 ml 1,2-dichloroethane. The mixture is heated to reflux for 2 hours and evaporated. The residue is purified by column on silica gel (ethyl acetate/5% methanol). Yield: 0.11 g (74%) yellow solid (mp: 315° C.).

Example 21

Complex 9

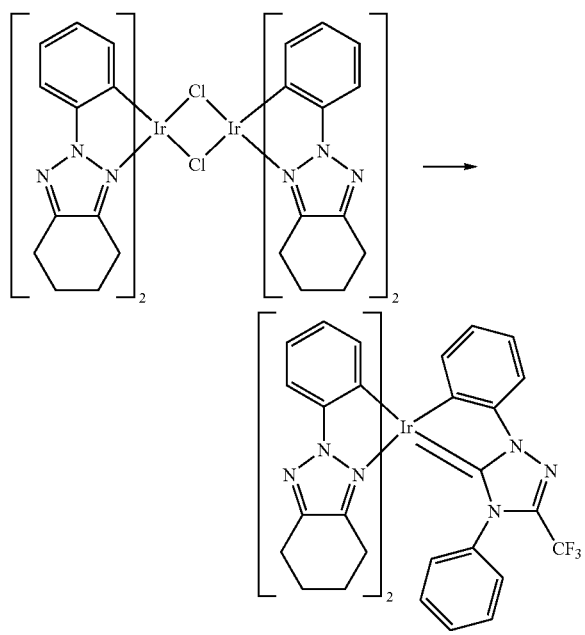

Procedure: 0.093 g (0.4 mmol) of 1,4-diphenyl-3-(trifluoromethyl)-4H-1,2,4-triazol-1-ium perchlorate is placed in a Schlenk tube together with 0.045 g (0.4 mmol) potassium tert. butoxide in 5 ml of ortho-xylene and stirred for 3 h at 130° under nitrogen. Finally, 0.062 g (0.05 mmol) of the dimer obtained according to example 13 is added and stirred at the same temperature over night. After cooling the solvent is removed by evaporation. The crude product is purified by column chromatography using hexane/dichloromethane/methanol as eluent mixture giving 0.05 g (46%) of the product.

Application Example 1

An organic luminescence device having a single organic layer is prepared in the following manner: On a glass substrate, a 100 nm thick ITO film is formed by sputtering and subsequently patterned. Onto the oxygen-plasma treated ITO film, a hole-injection layer of 80 nm thickness is formed by spin-coating using PEDOT:PSS (Baytron P), followed by heating at 200° C. (5 minutes). A solution of 5 mg of complex 2 (Example 14) and 95 mg of polyfluorene (average molecular weight 140 000) in 10 g of toluene are applied by spin coating (2000 rpm.; 10 seconds) to obtain a thickness of 80 nm. The substrate thus treated is placed in a vacuum deposition chamber, and a cathode having a two-layer electrode structure is formed by depositing a 50 nm layer of barium followed by a 100 nm layer of aluminum. When driving the device at a current density of 1 mA/cm² (at 8V), a clear bright white emission (CIE 0.30, 0.33) is observed.

The invention claimed is:

1. A compound of the formula

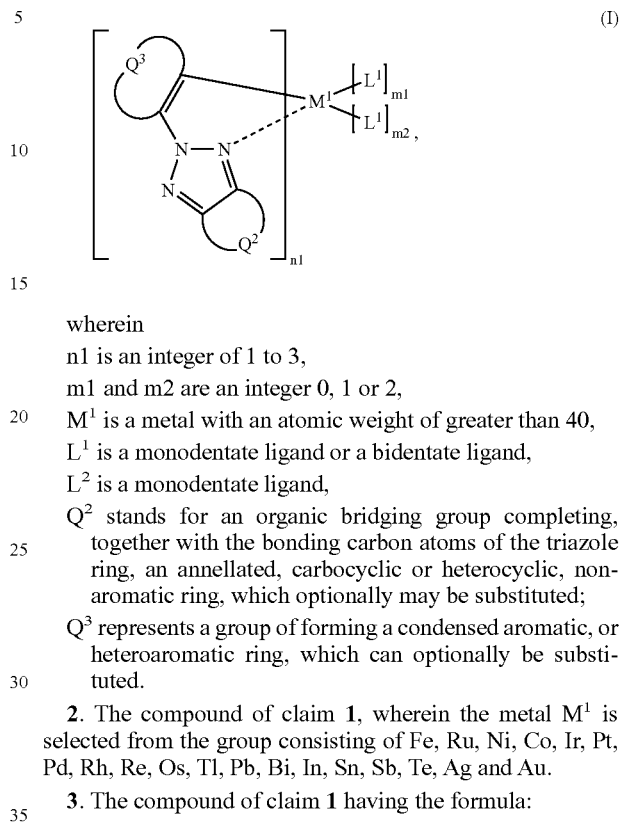

wherein n1 is an integer of 1 to 3, m1 and m2 are an integer 0, 1 or 2, $M^1$ is a metal with an atomic weight of greater than 40, $L^1$ is a monodentate ligand or a bidentate ligand, $L^2$ is a monodentate ligand, $Q^2$ stands for an organic bridging group completing, together with the bonding carbon atoms of the triazole ring, an annellated, carbocyclic or heterocyclic, non-aromatic ring, which optionally may be substituted;

$Q^3$ represents a group of forming a condensed aromatic, or heteroaromatic ring, which can optionally be substituted.

2. The compound of claim 1, wherein the metal $M^1$ is selected from the group consisting of Fe, Ru, Ni, Co, Ir, Pt, Pd, Rh, Re, Os, Tl, Pb, Bi, In, Sn, Sb, Te, Ag and Au.

3. The compound of claim 1 having the formula:

$$M^2L^a(L^b)_w(L^c)_x(L')_y(L'')_z \qquad (II),$$

wherein w=0 or 1, x=0 or 1, y=0, 1 or 2, and z=0 or 1, $M^2$ is Pt, Pd, Rh, Re, or Ir, L' is a bidentate ligand or a monodentate ligand; with the proviso that: when L' is a monodentate ligand, y+z=2, and when L' is a bidentate ligand, z=0;

L" is a monodentate ligand; and $L^a, L^b$ and $L^c$ are alike or different from each other and each of $L^a, L^b$ and $L^c$ has the structure (IIIa), (IIIb), or (IV) below:

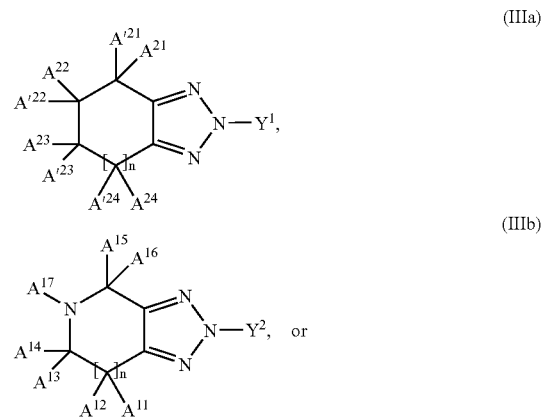

-continued (IV)

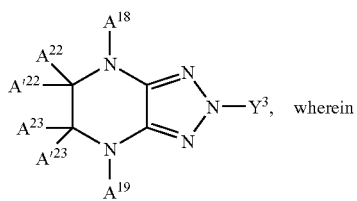

n is 0, 1 or 2;

$A^{12}, A^{14}, A^{16}, A^{21}, A^{22}, A^{23}$ and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$ perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G; or 2 adjacent radicals $A^{12}$, $A^{14}$; or $A^{14}$, $A^{17}$; or $A^{17}$, $A^{16}$; or $A^{21}$, $A^{22}$; or $A^{22}$, $A^{23}$; or $A^{23}$, $A^{24}$; or $A^{18}$, $A^{22}$; or $A^{23}$, $A^{19}$, bonding to vicinal atoms, together are a group of formula

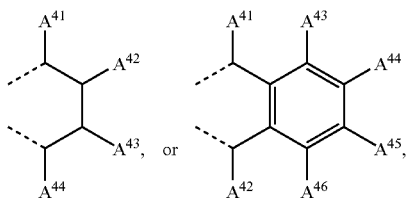

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}{}_9$ or —$COOR^{27}$, or $C_2$-$C_{10}$heteroaryl;

while each of $A^{11}$, $A^{13}$, $A^{15}$, $A'^{21}$, $A'^{22}$, $A'^{23}$ and $A'^{24}$ independently is hydrogen or $C_1$-$C_{24}$alkyl;

or 2 adjacent radicals $A^{11}$, $A^{21}$; $A^{13}$, $A^{14}$; $A^{15}$, $A^{16}$; $A'^{21}$, $A^{21}$; $A'^{22}$, $A^{22}$; $A'^{23}$, $A^{23}$; $A'^{24}$, $A^{24}$, bonding to the same carbon atom, together are =O or =$NR^{25}$ or =N—$OR^{25}$ or =N—OH;

$E^1$ is O, S, or $NR^{25}$, $R^{25}$ and $R^{26}$ are independently of each other $C_6$-$C_{18}$aryl, $C_7$-$C_{18}$aralkyl, or $C_1$-$C_{24}$alkyl, $R^{27}$ is $C_1$-$C_{24}$alkyl, $C_6$-$C_{18}$aryl, or $C_7$-$C_{18}$aralkyl; and $Y^1$, $Y^2$ and $Y^3$ are independently of each other a group of formula

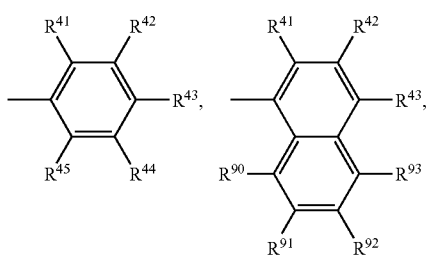

-continued

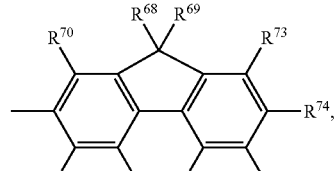

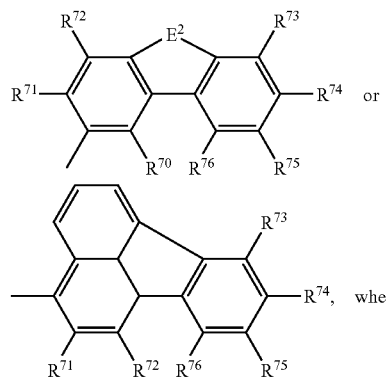

$R^{41}$ is the bond to $M^2$,
$R^{71}$ is the bond to $M^2$,
$R^{42}$ is hydrogen, or $C_1$-$C_{24}$alkyl, CN, $C_1$-$C_{24}$alkyl, which is substituted by halogen, $C_6$-$C_{18}$-aryl, $C_6$-$C_{18}$-aryl which is substituted by $C_1$-$C_{12}$alkyl, or $C_1$-$C_8$alkoxy,
$R^{43}$ is hydrogen, CN, halogen, $C_1$-$C_{24}$alkyl, which is substituted by F, $C_6$-$C_{18}$aryl, $C_6$-$C_{18}$aryl which is substituted by $C_1$-$C_{12}$alkyl, or $C_1$-$C_8$alkoxy, —$CONR^{25}R^{26}$, —$COOR^{27}$,

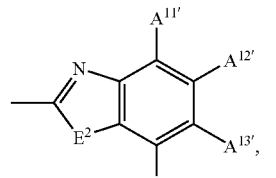

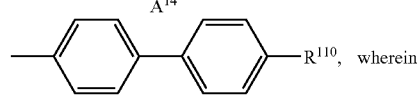

$E^2$ is —S—, —O—, or —$NR^{25'}$—, wherein $R^{25'}$ is $C_1$-$C_{24}$alkyl, or $C_6$-$C_{10}$aryl,
$R^{110}$ is H, CN, $C_1$-$C_{24}$alkyl, $C_1$-$C_{24}$alkoxy, $C_1$-$C_{24}$alkylthio, —$NR^{25}R^{26}$, —$CONR^{25}R^{26}$, or —$COOR^{27}$, or
$R^{42}$ and $R^{43}$ are a group of formula

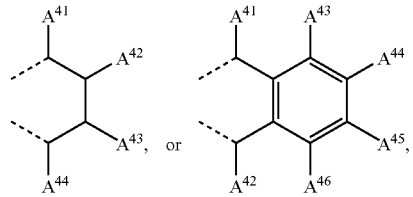

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —NR$^{25}$R$^{26}$, —CONR$^{25}$R$^{26}$$_9$ or —COOR$^{27}$, or C$_2$-C$_{10}$heteroaryl;

R$^{44}$ is hydrogen, CN or C$_1$-C$_{24}$alkyl, C$_1$-C$_{24}$alkyl, which is substituted by halogen, C$_6$-C$_{18}$-aryl, C$_6$-C$_{18}$-aryl which is substituted by C$_1$-C$_{12}$ alkyl, or C$_1$-C$_8$alkoxy, R$^{45}$ is hydrogen, CN or C$_1$-C$_{24}$alkyl, C$_1$-C$_{24}$alkyl, which is substituted by halogen, C$_6$-C$_{18}$-aryl, C$_6$-C$_{18}$-aryl which is substituted by C$_1$-C$_{12}$ alkyl, or C$_1$-C$_8$alkoxy, A$^{11'}$, A$^{12'}$, A$^{13'}$, and A$^{14'}$ are independently of each other H, halogen, CN, C$_1$-C$_{24}$alkyl, C$_1$-C$_{24}$alkoxy, C$_1$-C$_{24}$alkylthio, —NR$^{25}$R$^{26}$, —CONR$^{25}$R$^{26}$, or —COOR$^{27}$, R$^{68}$ and R$^{69}$ are independently of each other C$_1$-C$_{24}$alkyl, which can be interrupted by one or two oxygen atoms, R$^{70}$, R$^{72}$, R$^{73}$, R$^{74}$, R$^{75}$, R$^{76}$, R$^{90}$, R$^{91}$, R$^{92}$ and R$^{93}$ are independently of each other H, halogen, CN, C$_1$-C$_{24}$alkyl, C$_6$-C$_{10}$aryl, C$_1$-C$_{24}$alkoxy, C$_1$-C$_{24}$alkylthio, —NR$^{25}$R$^{26}$, —CONR$^{25}$R$^{26}$, or —COOR$^{27}$, wherein R$^{25}$, R$^{26}$ and R$^{27}$ are as defined above and G is C$_1$-C$_{18}$alkyl, —OR$^{305}$, —SR$^{305}$, —NR$^{305}$R$^{306}$, —CONR$^{305}$R$^{306}$, or —CN, wherein R$^{305}$ and R$^{306}$ are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl, or C$_1$-C$_{18}$alkyl which is interrupted by —O—; or R$^{305}$ and R$^{306}$ together form a five or six membered ring.

4. The compound of claim 3, wherein w is 1, x is 0 or 1, y is 0 or 1, and z=0, with x+y=1, and M$^2$ is Rh, Re, or Ir.

5. The compound of claim 1, wherein the bidentate ligand L$^1$ is a compound of formula

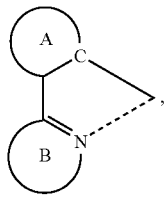

wherein the ring A,

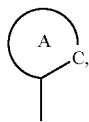

represents an optionally substituted aryl group which can optionally contain heteroatoms,
the ring B,

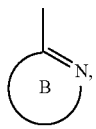

represents an optionally substituted nitrogen containing aryl group, which can optionally contain further heteroatoms, or the ring A may be taken with the ring B binding to the ring A to form a ring.

6. The compound of claim 5 having a structure (Va), (Vb), (Vc), (Vd), (Ve), (Vf) or (Vg):

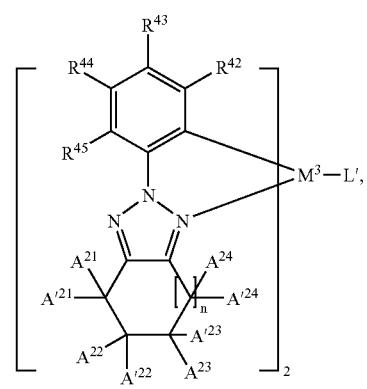
(Va)

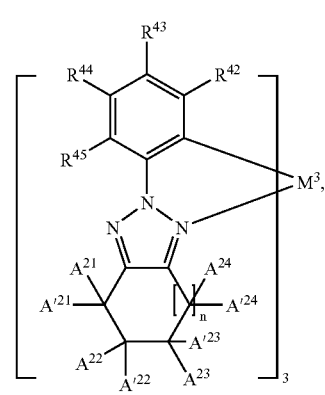
(Vb)

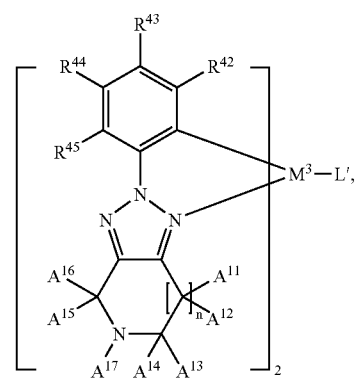
(Vc)

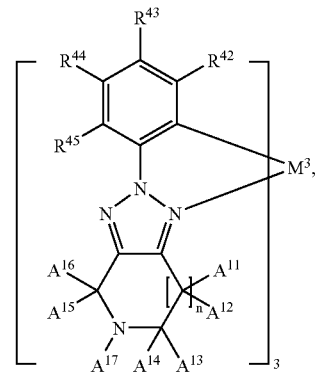
(Vd)

-continued

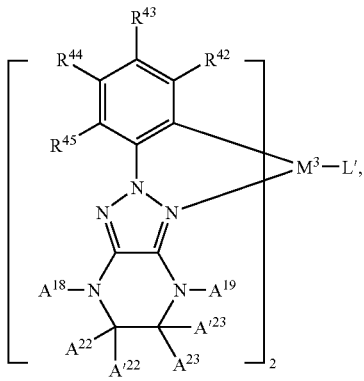

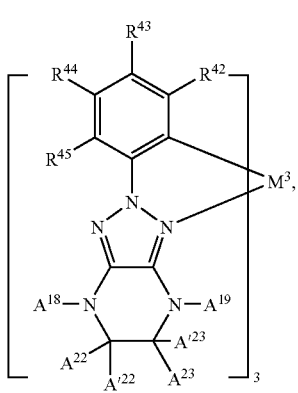

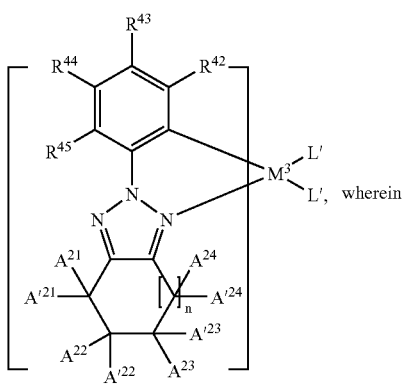

M³ is Rh, or Re, n is 0, 1 or 2, $A^{12}$; $A^{14}$; $A^{16}$, $A^{21}$; $A^{22}$, $A^{23}$ and $A^{24}$ are independently of each other hydrogen, CN, halogen, $C_1$-$C_{24}$alkyl, $C_1$-$C_{24}$alkoxy, $C_1$-$C_{24}$alkylthio, $C_1$-$C_{24}$ perfluoroalkyl, $C_6$-$C_{18}$aryl, which is optionally substituted by G; —$NR^{25}R^{26}$, —$CONR^{25}R^{26}$, or —$COOR^{27}$, or $C_2$-$C_{10}$heteroaryl, which is optionally substituted by G; or $C_5$-$C_{12}$cycloalkyl, $C_5$-$C_{12}$cycloalkoxy, $C_5$-$C_{12}$cycloalkylthio, each of which is optionally substituted by G; or 2 adjacent radicals $A^{12}$, $A^{14}$; or $A^{14}$, $A^{17}$; or $A^{17}$, $A^{16}$; or $A^{21}$, $A^{22}$; or $A^{22}$, $A^{23}$; or $A^{23}$, $A^{24}$; or $A^{18}$, $A^{22}$; or $A^{23}$, $A^{19}$, bonding to vicinal atoms, together are a group of formula

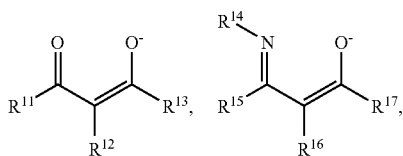

wherein $A^{41}$, $A^{42}$, $A^{43}$, $A^{44}$, $A^{45}$, $A^{46}$ and $A^{47}$ are independently of each other H, halogen, CN, $C_1$-$C_{24}$alkyl, $C_1$-$C_{24}$perfluoroalkyl, $C_1$-$C_{24}$alkoxy, $C_1$-$C_{24}$alkylthio, $C_6$-$C_{18}$aryl, which may optionally be substituted by G, —$NR^{25}R^{26}$, —$CONR^{25}R^{26}$; or —$COOR^{27}$, or $C_2$-$C_{10}$heteroaryl;

while each of $A^{11}$, $A^{13}$, $A^{15}$, $A^{21}$, $A^{22}$, $A^{23}$ and $A^{24}$ independently is hydrogen or $C_1$-$C_{24}$alkyl;

or 2 adjacent radicals $A^{11}$; $A^{12}$; $A^{13}$; $A^{14}$; $A^{15}$; $A^{16}$; $A^{21}$, $A^{21}$; $A^{22}$, $A^{22}$; $A^{23}$, $A^{23}$; $A^{24}$, $A^{24}$, bonding to the same carbon atom, together are =O or =$NR^{25}$.

7. The compound of claim 6 having a structure (Va), (Vb), (Vc), (Vd), (Ve), (Vf) or (Vg):

wherein L' is a bidentate ligand selected from

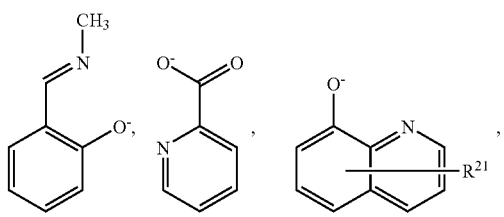

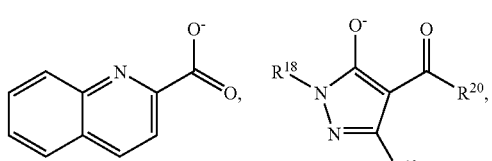

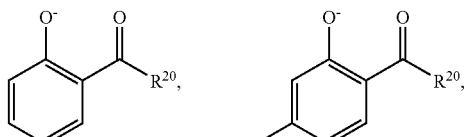

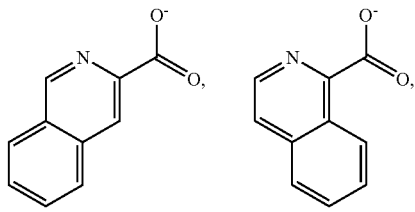

-continued

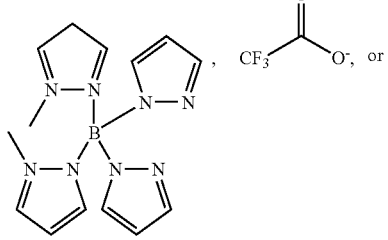,

,

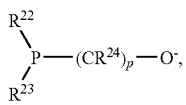,

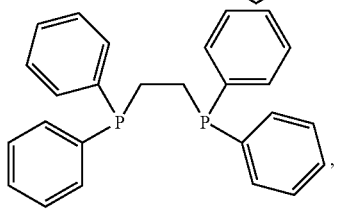,

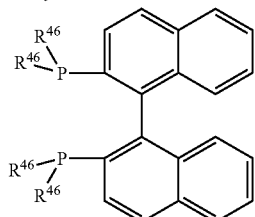,

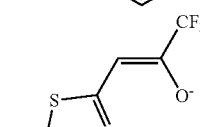;

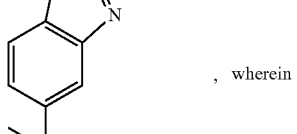, wherein $R^{11}$ and $R^{15}$ are independently of each other hydrogen, $C_1$-$C_8$alkyl, $C_6$-$C_{18}$aryl, $C_2$-$C_{10}$ heteroaryl, or $C_1$-$C_8$ perfluoroalkyl, $R^{12}$ and $R^{16}$ are independently of each other hydrogen, or $C_1$-$C_8$alkyl, and $R^{13}$ and $R^{17}$ are independently of each other hydrogen, $C_1$-$C_8$alkyl, $C_6$-$C_{18}$aryl, $C_2$-$C_{10}$ heteroaryl, $C_1$-$C_8$ perfluoroalkyl, or $C_1$-$C_8$alkoxy, and $R^{14}$ is $C_1$-$C_8$alkyl, $C_6$-$C_{10}$ aryl, or $C_7$-$C_{11}$aralkyl, $R^{18}$ is $C_6$-$C_{10}$ aryl, $R^{19}$ is $C_1$-$C_8$alkyl, $R^{20}$ is $C_1$-$C_8$alkyl, or $C_6$-$C_{10}$aryl, $R^{21}$ is hydrogen, $C_1$-$C_8$alkyl, or $C_1$-$C_8$alkoxy, which may be partially or fully fluorinated, $R^{22}$ and $R^{23}$ are independently of each other $C_n(H+F)_{2n+1}$, or $C_6(H+F)_5$, $R^{24}$ can be the same or different at each occurrence and is selected from H, or $C_n(H+F)_{2n+1}$, p is 2, or 3

$R^{42}$ is H, F, $C_1$-$C_4$alkyl, $C_1$-$C_8$alkoxy, or $C_1$-$C_4$ perfluoroalkyl, $R^{43}$ is H, F, $C_1$-$C_4$alkyl, $C_1$-$C_4$ perfluoroalkyl, $C_1$-$C_8$alkoxy, or $C_6$-$C_{10}$aryl, $R^{44}$ is H, F, $C_1$-$C_{12}$alkyl, $C_7$-$C_{15}$phenylalkyl, $C_1$-$C_8$alkoxy, or $C_1$-$C_4$perfluoroalkyl, $R^{45}$ is H, F, $C_1$-$C_4$alkyl, $C_1$-$C_8$alkoxy, or $C_1$-$C_4$perfluoroalkyl, and $R^{46}$ is $C_1$-$C_8$alkyl, $C_6$-$C_{18}$aryl, $C_1$-$C_8$alkoxy, or $C_6$-$C_{18}$aryl, which is substituted by $C_1$-$C_8$alkyl, or the bidentate ligand L' is selected from (X-1)

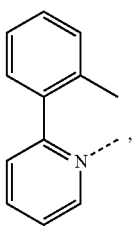

(X-2)

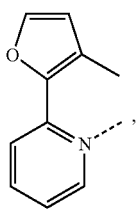

(X-3)

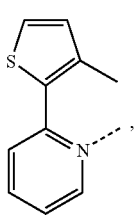

(X-4)

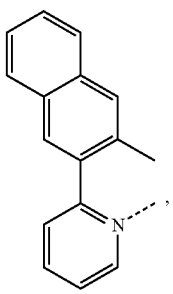

(X-5)

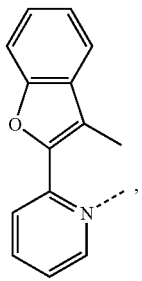

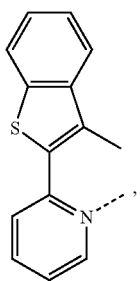
(X-6)
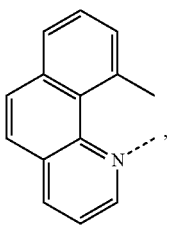
(X-7)
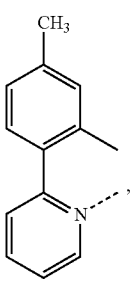
(X-8)
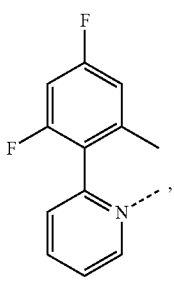
(X-9)
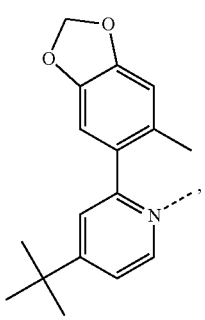
(X-10)
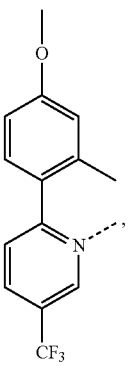
(X-11)
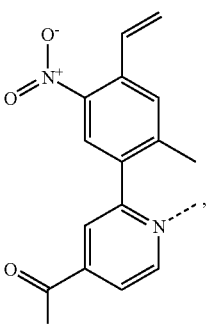
(X-12)
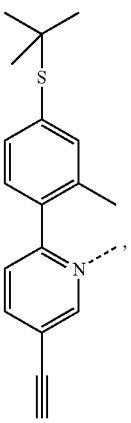
(X-13)
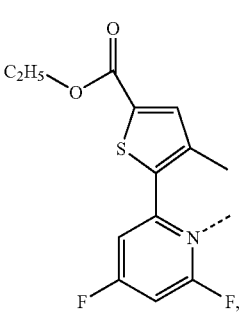
(X-14)

(X-15)
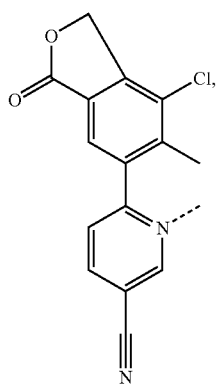
(X-16)
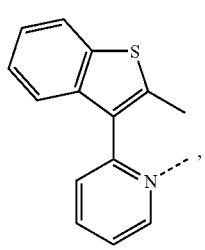
(X-17)
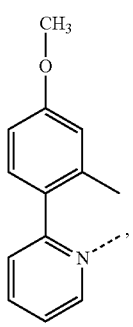
(X-18)
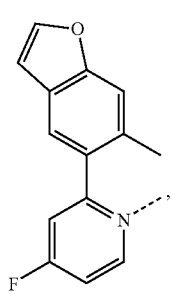
(X-19)
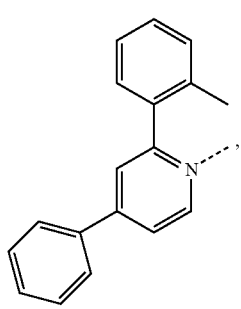
(X-20)
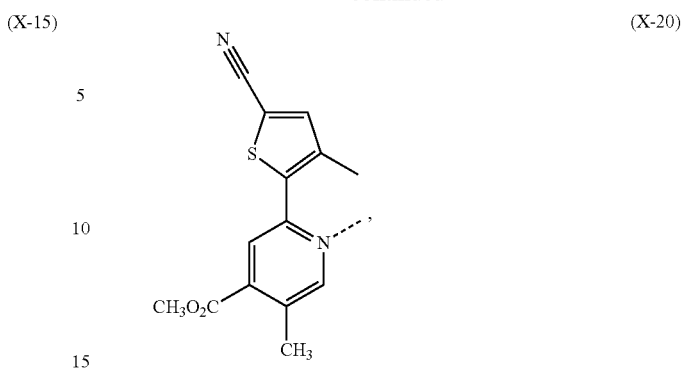
(X-21)
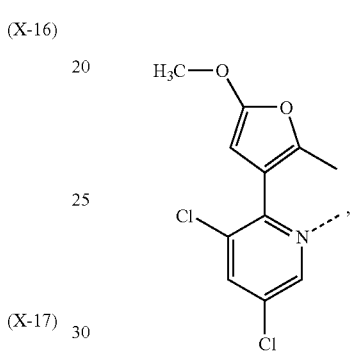
(X-22)
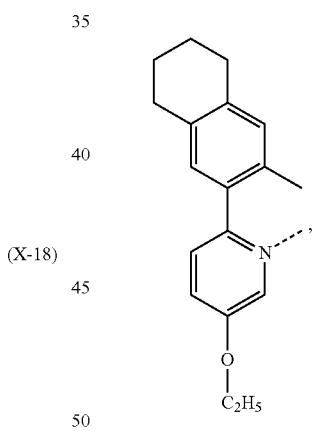
(X-23)
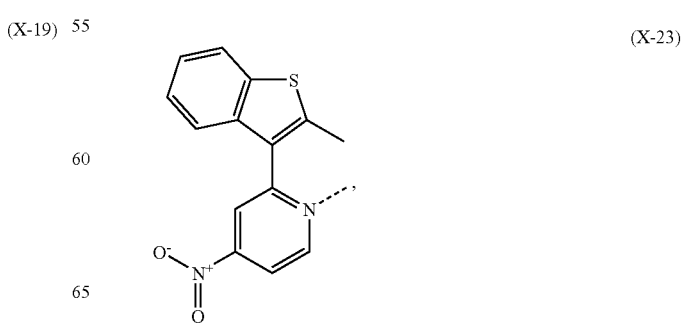

(X-24) 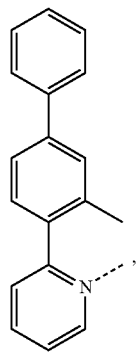
(X-25) 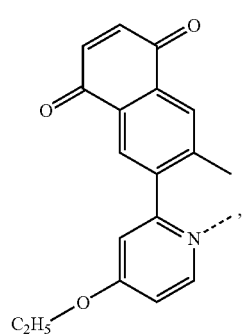
(X-26) 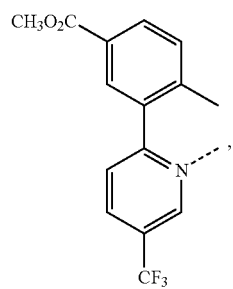
(X-27) 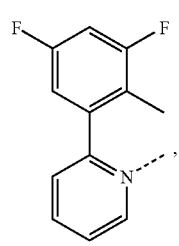
(X-28) 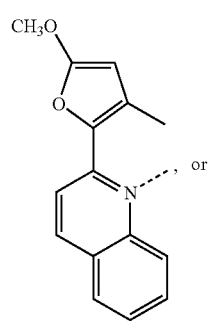 or
(X-29) 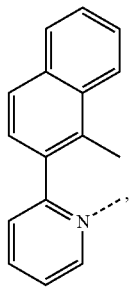
(X-30) 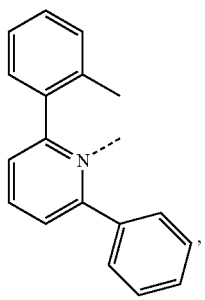
(X-31) 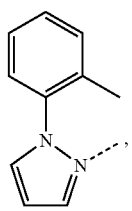
(X-32) 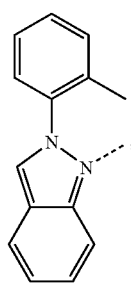
(X-33) 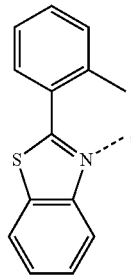
(X-34) 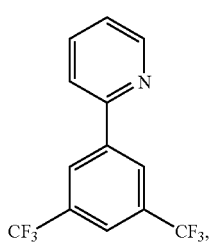

(X-35)
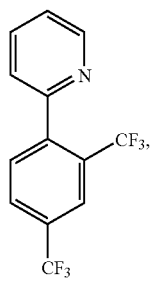
(X-36)
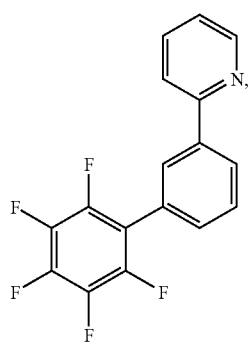
(X-37)
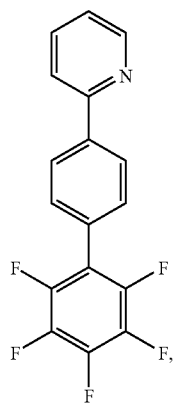
(X-37)
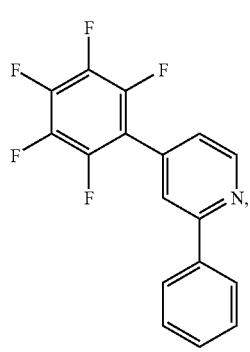
(X-38)
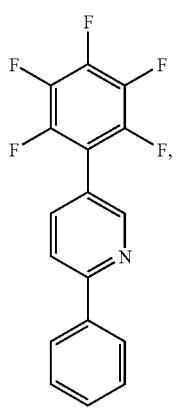
(X-39)
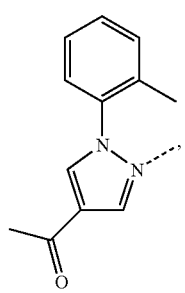
(X-40)
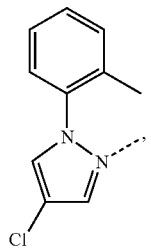
(X-41)
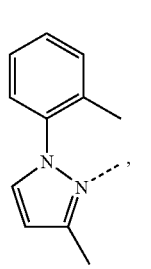
(X-42)
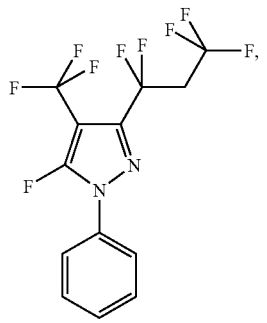

-continued (X-43)
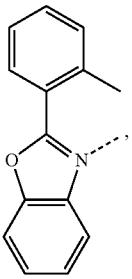

(X-44)
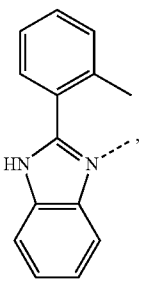

(X-45)
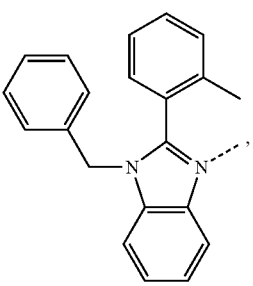

(X-46)
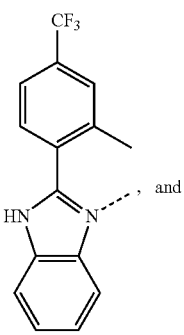

, and (X-47)
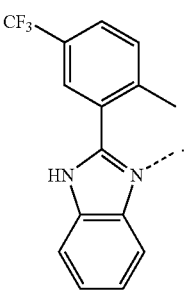

8. A compound of the formula

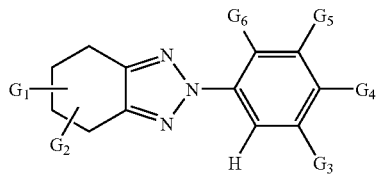

wherein
G$_1$ and G$_2$, independently, are hydrogen, CN, halogen, C$_1$-C$_{12}$alkyl, C$_1$-C$_{12}$haloalkyl, C$_1$-C$_{12}$alkoxy, C$_1$-C$_{12}$alkylthio, C$_5$-C$_{12}$cycloalkyl, C$_5$-C$_{12}$cycloalkoxy, C$_5$-C$_{12}$cycloalkylthio, C$_6$-C$_{12}$aryl, C$_2$-C$_{10}$heteroaryl, C$_7$-C$_{15}$arylalkyl, C$_6$-C$_{12}$aryloxy, C$_6$-C$_{12}$arylamino;
or G$_1$ and G$_2$, bonding to vicinal atoms, together are a group of formula

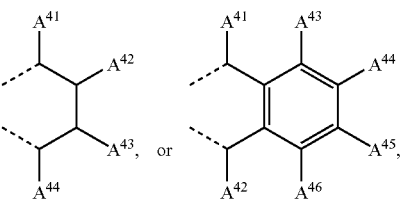

wherein A$^{41}$, A$^{42}$, A$^{43}$, A$^{44}$, A$^{45}$, A$^{46}$ and A$^{47}$ are independently of each other H, halogen, CN, C$_1$-C$_{12}$alkyl, C$_1$-C$_{12}$haloalkyl, C$_1$-C$_{12}$alkoxy, C$_1$-C$_{12}$alkylthio, C$_6$-C$_{12}$aryl; especially

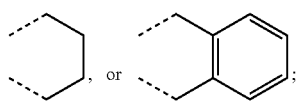

or G$_1$ and G$_2$, bonding to the same carbon atom, together are =O or =NR$^{25}$ or =N—OR$^{25}$ or =N—OH; where R$^{25}$ is C$_1$-C$_{12}$alkyl or cyclohexyl;
G$_3$, G$_4$, G$_5$ and G$_6$ independently are selected from hydrogen, C$_4$-C$_{18}$alkyl, C$_1$-C$_8$ perfluoroalkyl, fluoro; and at least one of G$_3$, G$_4$, G$_5$ and G$_6$ is different from hydrogen.

9. An organic electronic device, comprising an emitting layer wherein the emitting layer comprises a compound according to claim 1.

10. The device of claim 9, further comprising a hole transport layer selected from polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis (4-methylphenyl)-(1,1'-biphenyl)-4,4'-diamine (TTB), porphyrinic compounds, and combinations thereof.

11. An organic light emitting diode (OLED) comprising a compound according to claim 1.

12. The compound of claim 3 wherein
when $A^{12}$, $A^{14}$, $A^{16}$, $A^{21}$, $A^{22}$, $A^{23}$ or $A^{24}$ are $C_2$-$C_{10}$heteroaryl, the heteroaryl is a group of formula

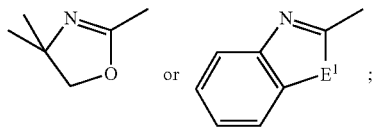

when 2 adjacent radicals $A^{12}$, $A^{14}$; or $A^{14}$, $A^{17}$; or $A^{17}$, $A^{16}$; or $A^{21}$, $A^{22}$; or $A^{22}$, $A^{23}$; or $A^{23}$, $A^{24}$; or $A^{18}$, $A^{22}$; or $A^{23}$, $A^{19}$, bonding to vicinal atoms, together are a group of formula

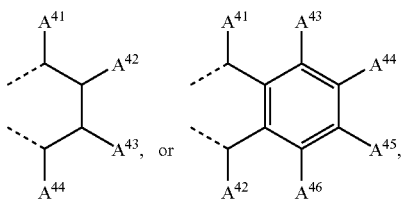

said group is

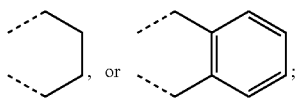

$R^{43}$ is hydrogen, CN, F, $C_1$-$C_{24}$alkyl, which is substituted by F, $C_6$-$C_{18}$aryl, $C_6$-$C_{18}$aryl which is substituted by $C_1$-$C_{12}$alkyl, or $C_1$-$C_8$alkoxy, —CONR$^{25}$R$^{26}$, —COOR$^{27}$,

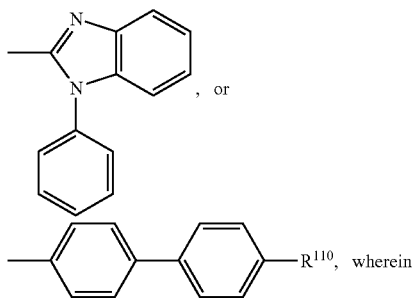

And when $R^{305}$ and $R^{306}$ together form a five or six membered ring, the five or six membered ring, is

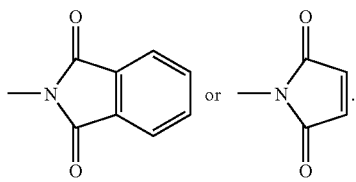

13. The compound of claim 12, wherein w is 1, x is 0 or 1, y is 0 or 1, and z=0, with x+y=1, and $M^2$ is Rh, Re, or Ir.

14. The compound of claim 3, wherein the bidentate ligand L' is a group of formula

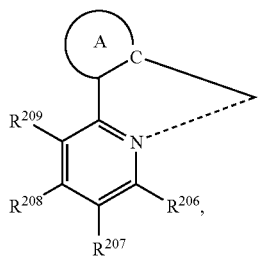

wherein $R^{206}$, $R^{207}$, $R^{208}$, and $R^{209}$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^{206}$, $R^{207}$, $R^{208}$, and $R^{209}$ may be substituted;

or is a group of the formula

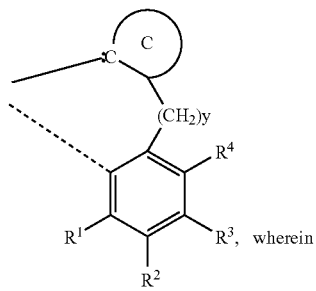

$R^1$ to $R^4$ are independently of each other hydrogen, halogen, nitro, cyano, $C_1$-$C_4$alkyl, $C_1$-$C_4$perfluoroalkyl, or $C_1$-$C_4$alkoxy, —S—$C_1$-$C_4$alkyl, —O—$C_1$-$C_4$ perfluoroalkyl, —SO$_2$X$^{22}$, —CO$_2$H, —CO$_2$X$^{22}$, wherein X$^{22}$ is $C_1$-$C_4$alkyl; $C_6$H$_4$CF$_3$, cyclohexyl, optionally substituted $C_6$-$C_{10}$aryl, optionally substituted —O—CH$_2$—$C_6$-$C_{10}$aryl, or optionally substituted —O—$C_6$-$C_{10}$aryl, y is 0, or 1, the group C,

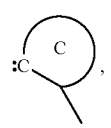

is a group of the following formula

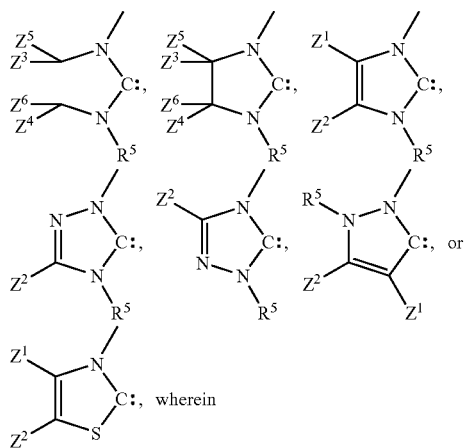

wherein

R[5] is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$-carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy; and $Z^1$, $Z^2$, $Z^3$, $Z^4$, $Z^5$ and $Z^6$ are independently of each other selected from the group consisting of hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

15. The compound of claim 5, wherein the bidentate ligand L[1] is a group of formula

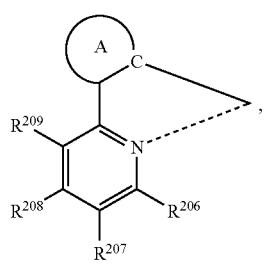

wherein R[206], R[207], R[208], and R[209] are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by R[206], R[207], R[208], and R[209] may be substituted; or is a group of the formula

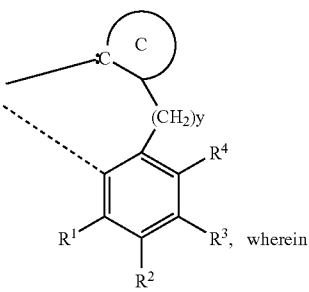

R[1] to R[4] are independently of each other hydrogen, halogen, nitro, cyano, $C_1$-$C_4$alkyl, $C_1$-$C_4$ perfluoroalkyl, or $C_1$-$C_4$alkoxy, —S—$C_1$-$C_4$alkyl, —O—$C_1$-$C_4$ perfluoroalkyl, —$SO_2X^{22}$, —$CO_2H$, —$CO_2X^{22}$, wherein $X^{22}$ is $C_1$-$C_4$alkyl; $C_6H_4CF_3$, cyclohexyl, optionally substituted $C_6$-$C_{10}$aryl, optionally substituted —O—$CH_2$—$C_6$-$C_{10}$aryl, or optionally substituted —O—$C_6$-$C_{10}$aryl, y is 0, or 1, the group C,

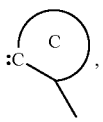

is a group of the following formula

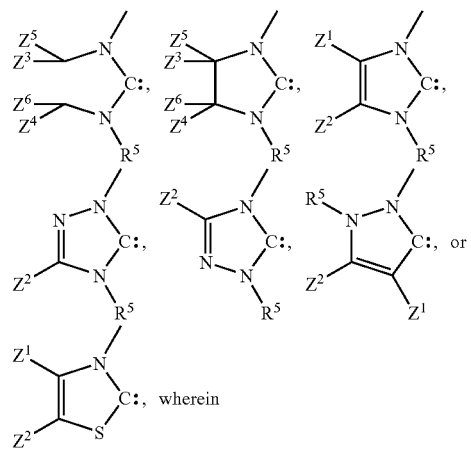

wherein

R[5] is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy; and $Z^1$, $Z^2$, $Z^3$, $Z^4$, $Z^5$ and $Z^6$ are independently of each other selected from the group consisting of hydrogen, $C_1$-$C_{24}$alkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

16. An oxygen sensitive indicator comprising a compound according to claim 1.

17. A phosphorescent indicator in a bioassay comprising a compound according to claim 1.

\* \* \* \* \*